United States Patent
Agnew et al.

(10) Patent No.: US 12,216,122 B2
(45) Date of Patent: Feb. 4, 2025

(54) COMPOSITIONS AND METHODS RELATING TO DETECTION, INHIBITION, AND IMAGING OF INDOLEAMINE 2,3-DIOXYGENASE 1 (IDO1)

(71) Applicant: Regeneron Pharmaceuticals, Inc., Tarrytown, NY (US)

(72) Inventors: Heather Dawn Agnew, Culver City, CA (US); Bert Tsunyin Lai, Culver City, CA (US); Anders Eliasen, Culver City, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 684 days.

(21) Appl. No.: 16/879,611

(22) Filed: May 20, 2020

(65) Prior Publication Data
US 2020/0371101 A1    Nov. 26, 2020

Related U.S. Application Data

(60) Provisional application No. 62/850,533, filed on May 20, 2019.

(51) Int. Cl.
*G01N 33/573*    (2006.01)
*C07K 1/06*    (2006.01)
(Continued)

(52) U.S. Cl.
CPC ............ *G01N 33/573* (2013.01); *C07K 5/10* (2013.01); *C07K 7/06* (2013.01); *C12N 9/0069* (2013.01); *G01N 33/68* (2013.01); *C07K 2319/70* (2013.01); *C12Q 2521/501* (2013.01); *C12Y 113/11052* (2013.01); *G01N 33/534* (2013.01); *G01N 2333/90241* (2013.01)

(58) Field of Classification Search
CPC .... G01N 33/573; G01N 33/68; G01N 33/534; G01N 2333/90241; C07K 5/10; C07K 7/06; C07K 2319/70; C12N 9/0069; C12Q 2521/501; C12Y 113/11052
USPC .......................................................... 435/7.4
See application file for complete search history.

(56) References Cited

U.S. PATENT DOCUMENTS

| | | |
|---|---|---|
| 4,899,755 A | 2/1990 | Lauffer |
| 5,021,556 A | 6/1991 | Srinivasan |
| (Continued) | | |

FOREIGN PATENT DOCUMENTS

| | | |
|---|---|---|
| EP | 2719706 | 4/2014 |
| WO | 1986006605 | 11/1986 |
| (Continued) | | |

OTHER PUBLICATIONS

BPS Bioscience: INCB024360 Analog Data Sheet (Year: 2012).*
(Continued)

*Primary Examiner* — Shafiqul Haq
(74) *Attorney, Agent, or Firm* — Fenwick & West LLP; Cara A. Mosley; Carl A. Morales

(57) ABSTRACT

The present application provides stable heterobiligands made up of peptide-based IDO1 ligands and small molecule inhibitors of IDO1 and methods of use of the heterobiligands as detection, imaging, diagnostic, and therapeutic agents. The application further provides methods of manufacturing IDO1 heterobiligands, capture agents, and imaging agents.

17 Claims, 15 Drawing Sheets
Specification includes a Sequence Listing.

(51) Int. Cl.

| | | |
|---|---|---|
| C07K 5/08 | (2006.01) | |
| C07K 5/10 | (2006.01) | |
| C07K 7/06 | (2006.01) | |
| C12N 9/02 | (2006.01) | |
| G01N 33/68 | (2006.01) | |
| G01N 33/534 | (2006.01) | |

(56) References Cited

U.S. PATENT DOCUMENTS

| | | | |
|---|---|---|---|
| 5,075,099 | A | 12/1991 | Srinivasan |
| 5,118,797 | A | 6/1992 | Jurisson |
| 5,183,653 | A | 2/1993 | Linder |
| 5,364,613 | A | 11/1994 | Sieving |
| 5,367,080 | A | 11/1994 | Toner |
| 5,387,409 | A | 2/1995 | Nunn |
| 5,474,756 | A | 12/1995 | Tweedle |
| 5,547,668 | A | 8/1996 | Kranz |
| 5,608,110 | A | 3/1997 | Ramalingam |
| 5,656,254 | A | 8/1997 | Ramalingam |
| 5,662,885 | A | 9/1997 | Pollak |
| 5,665,329 | A | 9/1997 | Ramalingam |
| 5,688,487 | A | 11/1997 | Linder |
| 5,720,934 | A | 2/1998 | Dean |
| 5,780,006 | A | 7/1998 | Pollak |
| 5,846,519 | A | 12/1998 | Tweedle |
| 5,849,261 | A | 12/1998 | Dean |
| 5,879,658 | A | 3/1999 | Dean |
| 5,886,142 | A | 3/1999 | Thakur |
| 5,976,495 | A | 11/1999 | Pollak |
| 6,093,382 | A | 7/2000 | Wedeking |
| 6,143,274 | A | 11/2000 | Tweedle |
| 6,566,088 | B1 | 5/2003 | McKnight |
| 8,710,180 | B2 | 4/2014 | Pitram |
| 8,841,083 | B2 | 9/2014 | Heath |
| 8,906,830 | B2 | 12/2014 | Agnew |
| 9,188,584 | B2 | 11/2015 | Agnew |
| 9,221,889 | B2 | 12/2015 | Pitram |
| 9,239,332 | B2 | 1/2016 | Heath |
| 9,913,875 | B2 | 3/2018 | Farrow |
| 10,598,671 | B2 | 3/2020 | Heath |
| 11,007,245 | B2 | 5/2021 | Farrow |
| 2006/0153839 | A1 | 7/2006 | Mohamed |
| 2010/0009896 | A1 | 1/2010 | Agnew |
| 2011/0177109 | A1 | 7/2011 | Smith, III |
| 2011/0263515 | A1 | 10/2011 | Agnew |
| 2012/0202219 | A1 | 8/2012 | Agnew |
| 2012/0252071 | A1 | 10/2012 | Greif |
| 2013/0156692 | A1 | 6/2013 | Pitram |
| 2014/0302998 | A1 | 10/2014 | Heath |
| 2015/0099658 | A1 | 4/2015 | Pfeilsticker |
| 2015/0132314 | A1 | 5/2015 | Farrow |
| 2015/0344523 | A1 | 12/2015 | Deyle |
| 2016/0331800 | A1 | 11/2016 | Farrow |
| 2018/0364253 | A1 | 12/2018 | Agnew |
| 2020/0407712 | A1 | 12/2020 | Boyd |
| 2022/0211648 | A1 | 7/2022 | Agnew |

FOREIGN PATENT DOCUMENTS

| | | | | |
|---|---|---|---|---|
| WO | 1991003200 | | 3/1991 | |
| WO | 1995003280 | | 2/1995 | |
| WO | 1995006633 | | 3/1995 | |
| WO | 1995028179 | | 10/1995 | |
| WO | 1995028967 | | 11/1995 | |
| WO | 1996003427 | | 2/1996 | |
| WO | 1996023526 | | 8/1996 | |
| WO | 1997036619 | | 10/1997 | |
| WO | 1998018496 | | 5/1998 | |
| WO | 1998018497 | | 5/1998 | |
| WO | 1998046612 | | 10/1998 | |
| WO | 9852618 | | 11/1998 | |
| WO | 1999017809 | | 4/1999 | |
| WO | 9921576 | | 5/1999 | |
| WO | 02/083064 | | 10/2002 | |
| WO | 03/006620 | | 1/2003 | |
| WO | 2003006620 | | 1/2003 | |
| WO | 2005/113762 | | 12/2005 | |
| WO | 2007/050963 | | 5/2007 | |
| WO | 2009/051555 | | 4/2009 | |
| WO | 2009/105746 | | 8/2009 | |
| WO | 2009/155420 | | 12/2009 | |
| WO | 2009155420 | A1 | 12/2009 | |
| WO | 2010/135431 | | 11/2010 | |
| WO | 2011/057347 | | 5/2011 | |
| WO | 2012/106651 | | 8/2012 | |
| WO | 2012106671 | | 8/2012 | |
| WO | 2013009869 | | 1/2013 | |
| WO | 2013/034982 | | 3/2013 | |
| WO | 2013033561 | | 3/2013 | |
| WO | 2014/056813 | | 4/2014 | |
| WO | 2014074907 | | 5/2014 | |
| WO | 2014/205317 | | 12/2014 | |
| WO | 2016038565 | | 3/2016 | |
| WO | 2017/011769 | | 1/2017 | |
| WO | 2018064597 | A1 * | 9/2017 | ............... C07K 7/06 |
| WO | 2017/176769 | | 10/2017 | |
| WO | 2018/064597 | | 4/2018 | |
| WO | 2018/111580 | | 6/2018 | |
| WO | 2018/170096 | | 9/2018 | |
| WO | 2018/200551 | | 11/2018 | |
| WO | 2020/127227 | | 6/2020 | |

OTHER PUBLICATIONS

Agnew, et al., Iterative in situ click chemistry creates antibody-like protein-Capture agents angew. Chemie int. Ed. , 48(27):4944-8 (2009).

Alexander, et al., "Intracranial black-blood MR angiography with high-resolution 3D fast spin echo", Magn. Reson. Med., 40:298-310 (1998).

Altschul, et al., "Gapped BLAST and PSI-BLAST: a new generation of protein database search programs", Nucleic Acids Res., 25:3389-402 (1997).

Claverie, "Information enhancement methods for large scale sequence analysis", Comput. Chem., 17:191-201 (1993).

Corson, et al., "Design and applications of bifunctional small molecules: Why two heads are better than one", ACS Chem. Biol., 3(11):677-692 (2008).

Das, et al., "A General Synthetic Approach for Designing Epitope Targeted Macrocyclic Peptide Ligands", Angew. Chemie Int. Ed., 54(45):13219-24 (2015).

Edelman, et al., "Extracranial carotid arteries: evaluation with "black blood" MR angiography", Radiology, 177:45-50 (1990).

Farrow, et al., "Epitope-Targeting of Tertiary Protein Structure Enables Target-Guided Synthesis of a Potent in Cell Inhibitor of Botulinum Neurotoxin", Angew. Chemie Int. Ed. , 54(24):7114-9 (2015).

Goodrich, et al., "A quantitative study of ramped radio frequency, magnetization transfer, and slab thickness in three-dimensional time-of-flight magnetic resonance angiography in a patient population", Invest. Radia, 31:323-32 (1996).

Iwata, et al., "A New, Convenient Method for the Preparation of 4-[18F] fluorobenzyl Halides", Applied Radiation and Isotopes, 5:87-92 (2000).

Lee, et al., "Rapid Microwave-Assisted CNBr Cleavage of Bead-Bond Peptides", J. Comb. Chem., (2008).

Liu, e al., "99mTc-Labeled Small Peptides as Diagnostic Radiopharmaceuticals", Chem. Rev., 99:2235-2268 (1999).

Meyers and Miller, "Optimal alignments in linear space", Comp Applic. Biol. Sci., 4(1):11-17 (1988).

Poethko, et al., "Two-Step Methodology for High-Yield Routine Radiohalogenation of Peptides: 18F-Labeled RGD and Octreotide Analogs", The Journal of Nuclear Medicine, 45:892-902 (2004).

Röhrig, et al., "Challenges in the Discovery of Indoleamine 2,3-Dioxygenase 1 (IDO1) Inhibitors", J. Med. Chem., (2015).

Schottelius, et al., "First 18F-Labeled Tracer Suitable for Routine Clinical Imaging of sst Receptor-Expressing Tumors Using Positron Emission Tomography", Clinical Cancer Research, 10:3593-3606 (2004).

(56) References Cited

OTHER PUBLICATIONS

Wootton, and Federhen, "Statistics of local complexity in amino acid sequences and sequences databases", Comput. Chem., 17(2):149-63 (1993).
Lee, et al., "Rapid Microwave-Assisted CNBr Cleavage of Bead-Bond Peptides", J. Comb. Chem., 10:807-809 (2008).
Agnew, et al., "Protein-Catalyzed Capture Agents", Chemical Reviews, 119(17): 9950-9970 (2019).
Artali, et al., "A molecular dynamics study of human serum albumin binding sites", Il Farmaco, 60:485-495 (2005).
Bianchi et al., "Vaccination with peptide mimetics of the gp41 prehairpin fusion intermediate yields neutralizing antisera against HIV-1 isolates", PNAS, 107(23): 10655-10660 (2010).
Boersma, "Gaining knowledge of single carbon chains", Theory of condensed matter, Radboud Univ. Nijmegen, 18 pages (2011).
Chan, et al., "Dual-targeting anti-angiogenic cyclic peptides as potential drug leads for cancer therapy", Scientific Reports, 6:35247, 13 pages (2016).
Chattopadhyay, et al., "Techniques to improve the direct ex vivo detection of low frequency antigen-specific CD8+ T cells with peptide-major histocompatibility complex class I tetramers", Cytometry Part A, 73(11): 1001-1009 (2008).
Chauhan, et al. "The Taming of the Cell Penetrating Domain of the HIV Tat: Myths and Realities", J. Control Release, 117(2): 148-162 (2007).
Chen, et al., "Fusion protein linkers: property, design and functionality", Adv. Drug Deliv. Rev., 65(10): 1357-1369 (2013).
Cheong, et al., "A patent review of IDO1 inhibitors for cancer", Expert Opinion on Therapeutic Patents, 28(4):317-330 (2018).
Choksi, et al., "A CD8 DE loop peptide analog prevents graft-versus-host disease in a multiple minor histocompatibility antigen-mismatched bone marrow transplantation model", Biology of Blood and Marrow Transplantation, 10(10):669-680 (2004).
Coppock, et al., "Peptide-based protein capture agents with high affinity, selectivity, and stability as antibody replacements in bio detection assays", Proc. of SPIE, 9107:910711-1 (2014).
Dieck, et al., "Development of bispecific molecules for the in situ detection of protein-protein interactions and protein phosphorylation", Cell & Biology, 21:357-368 (2014).
Eiber, et al., "Prostate-Specific Membrane Antigen Ligands for Imaging and Therapy", The Journal of Nuclear Medicine, 58(Supplement 2):67S-76S (2017).
Fisher, et al., "Trivalent Gd-DOTA reagents for modification of proteins", RSC Adv., 5: 96194-96200 (2015).
Fitzer-Attas, et al., "Harnessing Syk family tyrosine kinases as signaling domains for chimeric single chain of the Variable Domain recept", J. Immunol., 160(1):145-154 (1998).
Gao, et al., "Crystal structure of the complex between human CD8alpha(alpha) and HLA-A2", Nature, 387:630-4 (1997).
Gen Bank: AAH25715.1 , "CD8a molecule [Homo sapiens]" retrived from the internet Jun. 17, 2022.
Handl, et al., "Hitting multiple targets with multimeric ligands", Expert Opin. Ther. Targets, 8(6):565-586 (2004).
Hill, et al., "Constraining Cyclic Peptides to Mimic Protein Structure Motifs", Angewandte Chemie, 53(48):13020-13041 (2014).
Hirai, et al., "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, 9(7): 1956-1967 (2010).
Hudson, et al., "Multiplex epitope mapping using bacterial surface display reveals both linear and conformational epitopes", Scientific Reports, 2(706):1-9 (2012).
Josan, et al., "Cell-specific targeting by heterobivalent ligands", Bioconjug Chem., 22(7): 1270-1278 (2011).
Lai, et al., "Epitope-Targeted Macrocyclic Peptide Ligand with Picomolar Cooperative Binding to Interleukin-17F", Chemistry, 24(15):3760-3767 (2018).
Li, et al., "Identification of the CD8 DE loop as a surface functional epitope. Implications for major histocompatibility complex class I binding and CD8 inhibitor design", Journal of Biological Chemistry, 273(26): 16442-16445 (1998).
Lin, et al., "Inhibition of HIV-1 Tat-mediated transcription by a coumarin derivative, BPRHIV001, through the Akt pathway", Journal of Virology, 85(17): 9114-9126 (2011).
Lindlsey, et al., "The P13K/Akt Pathway: Recent Progress in the Development of ATP-Competitive and Allosteric Akt Kinase Inhibitors", Current Cancer Drug Targets, 8: 7-18 (2008).
Ma, et al., "A cyclic peptide-polymer probe for the detection of Clostridium botulinum neurotoxin serotype A", Toxicon, 47(8):901-908 (2006).
Mabry, et al., "Engineering of stable bispecific antibodies targeting IL-17 A and IL-23", Protein Engineering, Design & Selection, 23(3):115-127 (2010).
Macraild et al., "Antibody Recognition of Disordered Antigens", Structure 24:148-157, (2016).
Macraild et al., "Conformational Dynamics and Antigenicity in the Disordered Malaria Antigen Merozoite Surface Protein 2", PLOS ONE, 13 pages (2015).
Mamidyala et al., In situ click chemistry: probing the binding landscapes of biological molecules, Chemical Society Reviews, 39(4):1252-1261 (2010).
Manea, et al., "Antibody Recognition and Conformational Flexibility of a Plaque-Specific-Amyloid Epitope Modulated by Non-native Peptide Flanking Regions", J. Med. Chem., 51(5):1150-1161 (2008).
Matsuura, "Identification of conformational neutralizing epitopes on the capsid protein of canine calicivirus", Journal of General Virology, 82:1695-1702 (2001).
Melenhorst el., "Detection of low avidity CD8(+) T cell populations with coreceptor-enhanced peptide-major histocompatibility complex class I tetramers", J Immunol Methods, 338(1-2): 31-39 (2008).
Millward, et al., "In situ click chemistry: from small molecule discovery to synthetic antibodies", Integr. Biol (Camb)., 5(1): 87-95 (2013).
Millward, et al., "Iterative in situ click chemistry assembles a branched capture agent and allosteric inhibitor for Akt1", JACS, 133(45):18280-18288 (2011).
Miossec, "Update on interleukin-17: a role in the pathogenesis of inflammatory arthritis and implication for clinical practice", RMD Open, 3(1):e000284 (2017).
Mor, et al., Mimicking the Structure of the V3 Epitope Bound to HIV-1 Neutralizing Antibodies, Biochemistry, 48(15):3288-3303 (2009).
Muller, et al., "DOTA Conjugate with an Albumin-Binding Entity Enables the First Folic Acid-Targeted 177Lu-Radionuclide Tumor Therapy in Mice", The Journal of Nuclear Medicine, 54(1):124-131 (2013).
Nag et al., "A chemical epitope-targeting strategy for protein capture agents: the serine 474 epitope of the kinase Akt2", Angewandte Chemie International Edition, 52:13975-13979 (2013).
Pansca, et al., "Structural disorder in eukaryotes", PLoS ONE, www.plosone.org Apr. 1, 2012, 7(4): e34687, 10 pages (2012).
Pfeilsticker, et al., "A cocktail of thermally stable, chemically synthesized capture agents for the efficient detection of anti-gp41 antibodies from human sera", PloS One, 8(10):Article No. e76224, 5 pages (2013).
Saito, et al., "Identification of anti-CD98 antibody mimotopes for inducing antibodies with antitumor activity by mimotope immunization", Cancer Science, 105(4): 396-401 (2014).
Sarbassov, et al., "Phosphorylation and regulation of Akt/PKB by the rictor-mTOR complex", Science, American Association for the Advancement of Science, 307(5712): 1098-1101 (2005).
Schweinsberg, et al., "Novel glycated [99mTc(CO)3]-labeled bombesin analogues for improved targeting of gastrin-releasing peptide receptor-positive tumors", Bioconjugate Chem., 19(12):2432-2439 (2008).
Son, et al., "New Cyclic Lipopeptides of the Iturin Class Produced by Saltern-Derived Bacillus sp. KCB14S006", Marine Drugs, 14(4): 72 (2016).
Subramanyam, et al., "Inhibition of Protein Kinase Akt1 by Apoptosis Signal-regulating Kinase-1 (ASK1) Is Involved in Apoptotic Inhibition of Regulatory Volume Increase", Journal of Biological Chemistry, 285(9): 6109-6117(2010).

(56) References Cited

OTHER PUBLICATIONS

Tang et al., "Chimeric molecules facilitate the degradation of androgen receptors and repress the growth of LNCaP cells", *Asian Journal of Andrology*, 11(1): 119-126 (2009).
Tao, et al., "Expression, purification and identification of an immunogenic fragment in the ectodomain of prostate-specific membrane antigen", *Experimental and Therapeutic Medicine*, 11(3): 747-752 (2016).
Todorova, et al., "Biochemical nature and mapping of PSMA epitopes recognized by human antibodies induces after immunization with gene-based vaccines", *Anticancer Research*, 25: 4727-4732 (2005).
Torres, et al., "A revolutionary therapeutic approach for psoriasis: bi specific biological agents", *Expert Opinion on Investigational Drugs*, 25(7): 751-754 (2016).
Wang, et al., "Epitope Mapping Using Phage-Display Random Fragment Libraries", *Epitope Mapping Protocols, Methods in Molecular Biology*, 524: 315-332 (2009). Abstract Only.
Wang, et al., "Radioligand Therapy of Prostate Cancer with a Long-Lasting Prostate-Specific Membrane Antigen Targeting Agent 90Y-DOTA-EB-MCG", *Bioconjugate Chemistry*, 29(7): 2309-2315 (2018).
Wooldridge, et al., "Tricks with tetramers: how to get the most from multimeric peptide-MHC", *Immunology*, 126:147-164 2009 (2009).
Zhang, et al., "Structure and function of interleukin-17 family cytokines", *Protein & Cell*, 2(1): 26-40 (2011).
Lindsley, et al., "The P13K/Akt Pathway: Recent Progress in the Development of ATP-Competitive and Allosteric Akt Kinase Inhibitors", Current Cancer Drug Targets, 8: 7-18 (2008).
Muller, et al., "DOTA Conjugate with an Albumin-Binding Entity Enables the First Folic Acid-Targeted 177Lu-Radionuclide Tumor Therapy in Mice", The Jour. of Nucl. Med., 54(11): 124-131.
Agalave, et al., "Click chemistry: 1,2,3-triazoles as pharmacophores", Chem. Asian J., 6:(10)2696-27018 (2011).
Glaven, "Linking Single Domain Antibodies that Recognize Different Epitopes on the Same Target", Biosensors, 2:43-56 (2012).
Kirszbaum, et al., "The alpha-chain of murine CD8 lacks an invariant Ig-like disulfide bond but contains a unique intrachain loop instead", J. Immunol., 142(11):3931-6 (1989).
Koonin, et al., "Sequence—Evolution—Function: Computational Approaches in Comparative Genomics", Boston: Kluwer Academic; 2003, Chapter 2 Evolutionary Concept in Genetics and Genomics (2003).
Muller, et al., "Folic acid conjugates for nuclear imaging of folate receptor-positive cancer", J. Nucl. Med., 52(1): 1-4 (2011).
O'Shannessy, et al., "Characterization of the human folate receptor alpha via novel antibody-based probes", Oncotarget, 2(12):1227-1243 (2011).
Reeck, et al., "'Homolgy' in Proteins and Nucleic Acids: A Terminology Muddle and a Way out of it", Cell, 50:667 (1987).
Smith, et al., "Zinc mediated azide-alkyne ligation to 1,5- and 1,4,5-substituted 1,2,3-triazoles", Org. Lett., 15(18):4826-4829 (2013).
Sormanni, et al., "Rational design of antibodies targeting specific epitopes within intrinsically disordered proteins", PNAS, 112(32):9902-9907 (2015).
Sormanni, etal., PNAS, 112(32):1-10 (2015). Supplemental Materials.
Testa, et al., "CD 123 is a membrane biomarker and a therapeutic target in hematologic malignancies", Biomarker Research, 2:4 (2014).
Wang, et al., "Structural basis of the CD8 alpha beta/MHC class I interaction: focused recognition orients CD8 beta to a T cell proximal position", J. Immunol., 183(4):2554-64 (2009).

\* cited by examiner

FIG. 12A

EC50 (wyray) / EC50 (mutant)

[Bar chart with y-axis 0 to 1.2, bars labeled: wyray (~1.0), w1a (~0.25), y2a (~0.25), r3a (~0.4), y5a (~0)]

FIG. 12B

EC50 (wyray) / EC50 (4-mer)

[Bar chart with y-axis 0 to 1.5, bars labeled: wyray (~1.0), yray (~0.2), wray (~0.3), wyry (~1.4)]

COMPOSITIONS AND METHODS RELATING TO DETECTION, INHIBITION, AND IMAGING OF INDOLEAMINE 2,3-DIOXYGENASE 1 (IDO1)

CROSS-REFERENCE TO RELATED APPLICATIONS

This application claims benefit of U.S. Provisional Application No. 62/850,533, filed May 20, 2019. Application No. 62/850,533, filed May 20, 2019, is hereby incorporated herein by reference in its entirety.

REFERENCE TO SEQUENCE LISTING

The Sequence Listing submitted May 20, 2020, as a text file named "INDI_104_ST25.txt," created on May 20, 2020, and having a size of 28,880 bytes is hereby incorporated by reference pursuant to 37 C.F.R. § 1.52(e)(5).

FIELD OF THE INVENTION

The disclosed invention is generally in the field of Indoleamine 2,3-dioxygenase 1 (IDO1) and specifically in the area of compositions and methods relating to detection, inhibition, and imaging of IDO1.

BACKGROUND OF THE INVENTION

Anticancer therapies using immune checkpoint inhibitors result in remarkably durable clinical remissions in some patients, while other patients experience a short-term benefit or no benefit at all. The enzyme indoleamine 2,3-dioxygenase 1 (IDO1) is a resistance mechanism in the context of immunotherapies targeting immune checkpoints. IDO1 is a cytosolic protein that causes immunosuppression by breakdown of tryptophan in the tumor microenvironment and tumor-draining lymph nodes. The depletion of tryptophan and accumulation of toxic catabolites renders effector T cells inactive and dendritic cells immunosuppressive. There is a need in the art for IDO1 inhibitors for detecting IDO1 and for preventing IDO1-mediated immunotherapy resistance.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

Disclosed are compounds, compositions, and methods relating to ligands having affinity for an epitope on indoleamine 2,3-dioxygenase 1 (IDO1). In particular, disclosed are heterobiligands comprising a first ligand having affinity for an epitope on indoleamine 2,3-dioxygenase 1 (IDO1), a linker, and a second ligand, wherein the second ligand comprises a small molecule inhibitor of IDO1, wherein the linker links the first ligand and the second ligand, wherein the heterobiligand specifically binds and inhibits IDO1, wherein IDO1 comprises an active site, wherein the first ligand comprises a 3-10 amino acid sequence of D-amino acids, artificial amino acids, or combinations thereof, and wherein the small molecule inhibitor of IDO1 binds the IDO1 active site.

In some forms, the small molecule inhibitor of IDO1 binds the heme at the IDO1 active site. In some forms, the small molecule inhibitor of IDO1 is

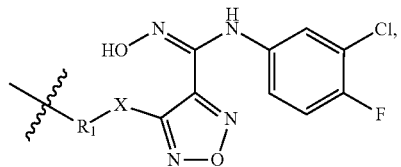

wherein X is S, O, or NH, wherein $R_1$ is —$CH_2$—$R_2$—, —($CH_2$)—$R_2$—, absent, —($CH_2$—$CH_2$—O)$_m$—$CH_2$—$CH_2$—$R_2$—, or —$CH_2$—$CH_2$—NH—$SO_2$—$R_2$—, wherein $R_2$ is —CO— or —NH—, wherein n is an integer from 2 to 10, wherein m is an integer from 1 to 6.

In some forms, the small molecule inhibitor of IDO1 is

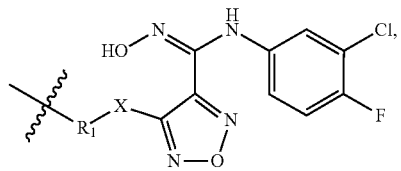

wherein X is S, wherein $R_1$ is —$CH_2$—$R_2$—, and wherein $R_2$ is —CO—.

In some forms, the small molecule inhibitor of IDO1 is

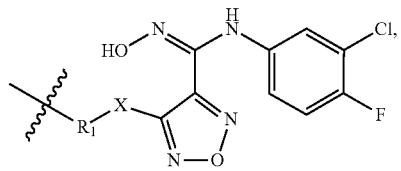

wherein X is NH, and wherein $R_1$ is absent.

In some forms, the small molecule inhibitor of IDO1 is

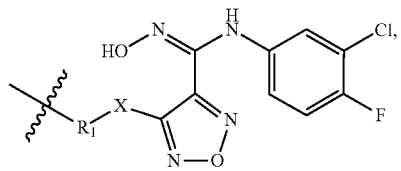

wherein X is NH, wherein $R_1$ is —$CH_2$—$CH_2$—NH—$SO_2$—$R_2$—, and wherein $R_2$ is —NH—.

In some forms, the first ligand comprises 5 to 9 amino acids.

In some forms, the epitope comprises the amino acid sequence GFWEDPKEFAGGSAGQSSVFQ (SEQ ID NO:1).

In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t (Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), yfn(Me-Trp)(Me-Trp) (SEQ ID NO:19), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t (Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), and yfn(Me-Trp)(Me-Trp) (SEQ ID NO:19)

In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), and frf(Me-Trp)s (SEQ ID NO:7). In some forms, the first ligand comprises an amino acid sequence wyvay (SEQ ID NO:2) or wyray (SEQ ID NO:3). In some forms, the first ligand comprises an amino acid sequence wyvay (SEQ ID NO:2).

In some forms, the first ligand does not comprise an amino acid sequence selected from the group consisting of wyray (SEQ ID NO:3), wyry (SEQ ID NO:4), nsfr(Me-Trp) (SEQ ID NO:6), frf(Me-Trp)s (SEQ ID NO:7), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the length of the linker is from about 11 Å to about 38 Å.

In some forms, the heterobiligand further comprises a detectable moiety. In some forms, the detectable moiety is selected from the group consisting of biotin, copper-DOTA, biotin-PEG$_3$, aminooxyacetate, $^{19}$FB $^{18}$FB, and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br. In some forms, the detectable moiety is $^{18}$F.

Also disclosed are compositions comprising a first ligand having affinity for an epitope on indoleamine 2,3-dioxygenase 1 (IDO1), a linker, and an E3 ligase ligand, wherein the linker links the first ligand and the E3 ligase ligand, wherein the composition specifically binds IDO1. In some forms, the first ligand comprises a 3-10 amino acid sequence of D-amino acids, artificial amino acids, or combinations thereof. In some forms, the first ligand comprises 5 to 9 amino acids.

In some forms, the epitope comprises the amino acid sequence LPPILVYADCVLANWKKKDPNK (SEQ ID NO:24). In some forms, the first ligand comprises an amino acid sequence selected from the group consisting of rys(Me-Trp)r (SEQ ID NO:25), X41f(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:26 and 27), nlw(Me-Trp)r (SEQ ID NO:28), and sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:29 and 30). In some forms, the first ligand comprises an amino acid sequence of nlf(Me-Trp)(F-Phe) (SEQ ID NO:31), alf(Me-Trp)(F-Phe) (SEQ ID NO:32), or lf(Me-Trp)(F-Phe) (SEQ ID NO:27) (SEQ ID NO:27). In some forms, the first ligand comprises an amino acid sequence of spww(F-Phe) (SEQ ID NO:33), saww(F-Phe) (SEQ ID NO:34), or sww(F-Phe) (SEQ ID NO:35).

In some forms, the epitope comprises the amino acid sequence NKPLTYENMDVLFSFR (SEQ ID NO:36). In some forms, the first ligand comprises an amino acid sequence selected from the group consisting of rffyl (SEQ ID NO:37) and nsh(F-Phe)r (SEQ ID NO:38).

In some forms, the epitope comprises the amino acid sequence GFWEDPKEFAGGSAGQSSVFQ (SEQ ID NO:1). In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t(Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), yfn(Me-Trp)(Me-Trp) (SEQ ID NO:19), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp). In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t(Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), and yfn(Me-Trp)(Me-Trp) (SEQ ID NO:19).

In some forms, the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), and frf(Me-Trp)s (SEQ ID NO:7). In some forms, the first ligand comprises an amino acid sequence wyvay (SEQ ID NO:2) or wyray (SEQ ID NO:3). In some forms, the first ligand comprises an amino acid sequence wyvay (SEQ ID NO:2).

In some forms, the first ligand does not comprise an amino acid sequence selected from the group consisting of wyray (SEQ ID NO:3), wyry (SEQ ID NO:4), nsfr(Me-Trp) (SEQ ID NO:6), frf(Me-Trp)s (SEQ ID NO:7), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the length of the linker is sufficient to allow the E3 ligase ligand to recruit E3 ligase to IDO1 in proximity to a lysine residue on IDO1 when the composition is bound to IDO1. In some forms, the length of the linker is from about 11 Å to about 38 Å.

In some forms, the composition further comprises a detectable moiety. In some forms, the detectable moiety is selected from the group consisting of biotin, copper-DOTA, biotin-PEG$_3$, aminooxyacetate, $^{19}$FB, $^{18}$FB, and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br. In some forms, the detectable moiety is $^{18}$F.

Also disclosed are methods of detecting IDO1 in a biological sample, comprising contacting the biological sample with any of the disclosed the heterobiligands or any of the disclosed compositions. In some forms, the method further comprises binding IDO1 to the heterobiligand or composition, and detecting the detectable moiety linked to the heterobiligand or composition.

Also disclosed are methods of reducing IDO1 enzymatic activity comprising contacting IDO1 with an effective amount of any of the disclosed the heterobiligands or any of the disclosed compositions, thereby reducing IDO1 enzymatic activity. In some forms, the IDO1 is contacted with an effective amount of any of the disclosed the heterobiligands.

Also disclosed are methods of detecting IDO1 comprising contacting IDO1 with an effective amount of the heterobiligand of any of the disclosed the heterobiligands or any of the disclosed compositions.

In some forms, the IDO1 is located in the cytosol of an intact cell.

Also provided herein are compositions that specifically bind indoleamine 2,3-dioxygenase 1 (IDO1).

In one aspect, provided herein is a composition that specifically binds indoleamine 2,3-dioxygenase 1 (IDO1) comprising a first ligand having affinity for an epitope on IDO1, wherein the ligand comprises a 5-10 amino acid sequence of D-amino acids and artificial amino acids and wherein IDO1 comprises an active site.

In some forms, the epitope comprises 8 to 30 amino acids.

In some forms, the epitope is located within 38 Å of the IDO1 active site.

In some forms, the ligand comprises 5 to 9 amino acids.

In some forms, the ligand comprises a small molecule inhibitor. In some forms, the small molecule inhibitor is an inhibitor of IDO1 enzymatic activity.

In some forms, the ligand comprises a 1-methyl-tryptophan (Me-Trp) moiety.

In some forms, the epitope comprises the amino acid sequence GFWEDPKEFAGGSAGQSSVFQ (SEQ ID NO:1. In some forms, the ligand comprises an amino acid sequence selected from the group consisting of X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nsfr(Me-Trp) (SEQ ID NO:6), and wyrX3y, wherein X3 is D-Ala or is not present (SEQ ID NOs:3 and 4). In some forms, the ligand comprises an amino acid sequence selected from the group consisting of frf(Me-Trp)s (SEQ ID NO:7), arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp). In some forms, the ligand comprises an amino acid sequence of wyray (SEQ ID NO:3) or wyry (SEQ ID NO:4).

In some forms, the epitope comprises the amino acid sequence LPPILVYADCVLANWKKKDPNK (SEQ ID NO:24). In some forms, the ligand comprises an amino acid sequence selected from the group consisting of rys(Me-Trp)r (SEQ ID NO:25) (SEQ ID NO:25), X41f(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:26 and 27), nlw(Me-Trp)r (SEQ ID NO:28), and sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:29 and 30). In some forms, the ligand comprises an amino acid sequence of nlf(Me-Trp)(F-Phe) (SEQ ID NO:31), alf(Me-Trp)(F-Phe) (SEQ ID NO:32), or lf(Me-Trp)(F-Phe) (SEQ ID NO:27). In some forms, the ligand comprises an amino acid sequence of spww(F-Phe) (SEQ ID NO:33), saww(F-Phe) (SEQ ID NO:34), or sww(F-Phe) (SEQ ID NO:35).

In some forms, the epitope comprises the amino acid sequence NKPLTYENMDVLFSFR (SEQ ID NO:36). In some forms, the ligand comprises an amino acid sequence selected from the group consisting of rffyl (SEQ ID NO:37) and nsh(F-Phe)r (SEQ ID NO:38).

In some forms, the composition further comprises a small molecule that inhibits the activity of IDO1. In some forms, the small molecule that inhibits the activity of IDO1 is covalently attached to the ligand.

In an aspect, provided herein is a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids and wherein IDO1 comprises an active site.

In some forms, the first and second epitopes independently comprise 8 to 30 amino acids.

In some forms, the first and second epitopes are located within 38 Å of the IDO1 active site.

In some forms, the first and second ligands independently comprise 5 to 9 amino acids.

In some forms, at least one of the first and second ligands comprises a Me-Trp moiety.

In some forms, the first epitope and the second epitope are distinct from each other and comprise an amino acid sequence selected from the group consisting of GFWEDPKEFAGGSAGQSSVFQ (SEQ ID NO:1), LPPILVYADCVLANWKKKDPNK (SEQ ID NO:24), and NKPLTYENMDVLFSFR (SEQ ID NO:36). In some forms, the first ligand and the second ligand each bind the first or the second epitope and comprise an amino acid sequence selected from the group consisting of X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nsfr(Me-Trp) (SEQ ID NO:6), wyrX3y, wherein X3 is D-Ala or is not present (SEQ ID NOs:3 and 4), rys(Me-Trp)r (SEQ ID NO:25), X41f(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:26 and 27), nlw(Me-Trp)r (SEQ ID NO:28), sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:29 and 30), rffyl (SEQ ID NO:37), and nsh(F-Phe)r (SEQ ID NO:38). In some forms, the ligand comprises an amino acid sequence selected from the group consisting of frf(Me-Trp)s (SEQ ID NO:7), arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp). In some forms, the ligand comprises an amino acid sequence of wyray (SEQ ID NO:3) or wyry (SEQ ID NO:4). In some forms, the ligand comprises an amino acid sequence of nlf(Me-Trp)(F-Phe) (SEQ ID NO:31), alf(Me-Trp)(F-Phe) (SEQ ID NO:32), or lf(Me-Trp)(F-Phe) (SEQ ID NO:27). In some forms, the ligand comprises an amino acid sequence of spww(F-Phe) (SEQ ID NO:33), saww(F-Phe) (SEQ ID NO:34), or sww(F-Phe) (SEQ ID NO:35).

In some forms, either the first ligand or the second ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the length of the linker corresponds to the distance between the first epitope and the second epitope. In some forms, the length of the linker is from about 11 Å to about 38 Å.

In some forms, the composition further comprises a detectable moiety. In some forms, the detectable moiety is selected from the group consisting of biotin, copper-DOTA, biotin-PEG$_3$, aminooxyacetate, $^{19}$FB, $^{18}$FB, and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br. In some forms, the detectable moiety is $^{18}$F.

In another aspect, provided herein is a method of detecting IDO1 in a biological sample, comprising contacting the biological sample with one or more compositions of any one of the previous claims.

In some forms, the method further comprises binding IDO1 to said one or more composition, and detecting the detectable moiety linked to said one or more imaging agents.

In another aspect, provided herein is a method of identifying a composition that specifically binds to a target protein, wherein the composition comprises a 5-10 amino acid sequence of D-amino acids and artificial amino acids, comprising contacting an epitope of the target protein to a library of molecules wherein the members of the library comprise distinct peptides of 5-10 amino acids, wherein the amino acids are D-amino acids or artificial amino acids, and wherein the epitope of the target protein comprises 8-30 amino acids and comprises an azide click handle; covalently binding members of the library that specifically bind to the epitope to the azide click handle; and identifying the amino acid sequence of the library members that covalently bind to the epitope.

In some forms, the target protein is IDO1.

In some forms, the epitope of IDO1 comprises an amino acid sequence with one substitution from a sequence selected from the group consisting of GFWEDPKEF-AGGSAGQSSVFQ (SEQ ID NO:1), LPPILVYADCV-LANWKKKDPNK (SEQ ID NO:24), and NKPLTY-ENMDVLFSFR (SEQ ID NO:36).

In some forms, the epitope of IDO1 comprises an amino acid sequence selected from the group consisting of GFWEDPKEAz4AGGSAGQSSVFQ (SEQ ID NO:39), LPPILVYADCVAz4ANWKKKDPNK (SEQ ID NO:40), and NKPLTYENMAz4VLFSFR (SEQ ID NO:41).

In another aspect, provided herein is a method of treating a cancer in a subject in need thereof comprising administering a therapeutically effective amount of a composition that specifically binds IDO1 comprising a first ligand having affinity for an epitope on IDO1, wherein the ligand comprises a 5-10 amino acid sequence of D-amino acids and artificial amino acids and wherein IDO1 comprises an active site, thereby treating the cancer.

In another aspect, provided herein is a method of reducing IDO1 enzymatic activity comprising contacting IDO1 with an effective amount of a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids, thereby reducing IDO1 enzymatic activity.

In another aspect, provided herein is a method of detecting IDO1 comprising contacting IDO1 with an effective amount of a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids. In some forms, the IDO1 to be detected is located in the cytosol of an intact cell.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A. Crystal structure of human IDO1 with Epitopes 1 and 2, the heme group and active site shown. FIG. 1B. Crystal structure of human IDO1 with Epitopes 1N and 3 shown.

FIG. 2A. Binding affinities for frf(Me-Trp)s (SEQ ID NO:7). FIG. 2B. Binding affinities for rys(Me-Trp)r (SEQ ID NO:25). FIG. 2C. Binding affinities for nlf(Me-Trp)(F-Phe) (SEQ ID NO:31). FIG. 2D. Binding affinities for nlw(Me-Trp)r (SEQ ID NO:28). FIG. 2E. Binding affinities for spww(F-Phe) (SEQ ID NO:33). FIG. 2F. Binding affinities for wyray (SEQ ID NO:3). FIG. 2G. Binding affinities for rffyl (SEQ ID NO:37). FIG. 2H. Binding affinities for nsh(F-Phe)r (SEQ ID NO:38).

FIG. 4A. Point ELISA for the 6×His-tagged IDO1 epitopes against frf(Me-Trp)s (SEQ ID NO:7). FIG. 4B. Point ELISA for the 6×His-tagged IDO1 epitopes against nlw(Me-Trp)r (SEQ ID NO:28). FIG. 4C. Point ELISA for the 6×His-tagged IDO1 epitopes against spww (F-Phe) (SEQ ID NO:33).

FIG. 5A. Alanine scan of macrocycle to determine amino acids critical to IDO1 binding (SEQ ID NOs:44, 34, 45, 46, and 47 from top to bottom). FIG. 5B. Smaller macrocycles (3-mer and 4-mer) to compare ring size and IDO1 binding (SEQ ID NOs:58, 59, -, and 35 from top to bottom).

FIG. 6A. Alanine scan of macrocycle to determine amino acids critical to IDO1 binding (SEQ ID NOs:3, 55, 56, 8, and 57 from top to bottom). FIG. 6B. Smaller macrocycles (4-mer) to compare ring size and IDO1 binding (SEQ ID NOs:63, 64, 65, and 4 from top to bottom).

FIG. 7A. Alanine scan of macrocycle to determine amino acids critical to IDO1 binding (SEQ ID NOs:32, 48, 49, 50, and 51 from top to bottom). FIG. 7B. Smaller macrocycles (3-mer and 4-mer) to compare ring size and IDO1 binding (SEQ ID NOs:61, 27, 60, and—from top to bottom).

FIG. 8A. Alanine scan of macrocycle to determine amino acids critical to IDO1 binding (SEQ ID NOs:20, 52, 53, 54, and 22 from top to bottom). FIG. 8B. Smaller macrocycles (4-mer) to compare ring size and IDO1 binding (SEQ ID NOs:23, 21, and 62 from top to bottom).

FIG. 11A. SEQ ID NOs:18, 7, 13, 14, 17, 6, and 15 from left to right. FIG. 11B. SEQ ID NOs:3, 19, 5, 9, 10, 12, and 16 from left to right.

FIGS. 12A-12B: EC50 of wyray and variants of wyray (SEQ ID NO:3). FIG. 12A. Bar graph of EC50 of macrocycle variants of wyray (SEQ ID NO:3) made by substituting any of the five positions with alanine. Variants: w1a (SEQ ID NO:55), y2a (SEQ ID NO:56), r3a (SEQ ID NO:8), y5a (SEQ ID NO:57). FIG. 12B. Bar graph of EC50 of macrocycle variants of wyray (SEQ ID NO:3) made by ring-reduction to produce 4-mer variants. Variants: yray (SEQ ID NO:63), wray (SEQ ID NO:64), wyry (SEQ ID NO:4).

DETAILED DESCRIPTION OF THE INVENTION

Figure 1A:
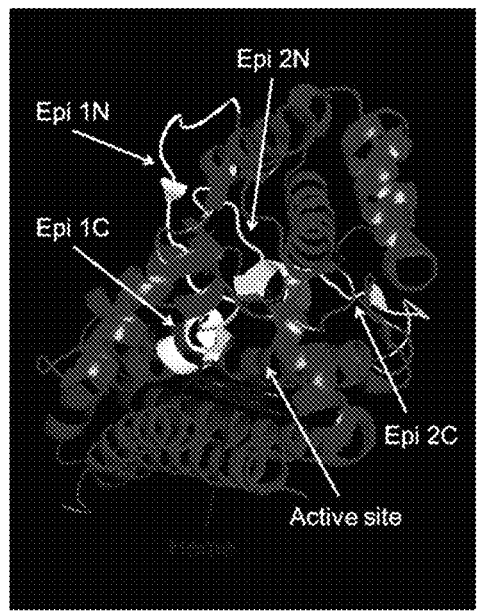
FIGS. 1A-1B: Epitopes derived from the IDO1 protein.

The disclosed method and compositions can be understood more readily by reference to the following detailed description of particular embodiments and the Example included therein and to the Figures and their previous and following description.

Protein target is indoleamine 2,3-dioxygenase 1 (IDO1), an intracellular heme enzyme that acts on multiple tryptophan substrates. IDO1 has a suppressive role in the context of immunotherapies targeting immune checkpoints. Developing a PCC imaging agent will have utility in identifying tumors that express IDO1, thus providing an imaging marker for potential resistance to therapy and for emerging treatments targeting IDO1 activity. Epitope-targeted macrocyclic peptide ligands against IDO1 were identified using protein catalyzed capture agent (PCC) technology and have been joined with a small molecule inhibitor of IDO1 via a linker to form heterobiligands useful for binding, detection, imaging, and detecting IDO1.

Epitope-targeted macrocyclic peptide ligands against IDO1 were identified using PCC technology and were further developed as in vivo positron emission tomography (PET) imaging agents and IDO1 inhibitors. Three human IDO1 epitopes have been designed and screened against one-bead-one-compound (OBOC) peptide libraries. Two epitopes are located at or near the active site, while the third epitope is situated on the protein surface. Epitope-targeted macrocyclic peptide ligands were identified against IDO1 with binding affinities (EC50 values) ranging from 20 to 125 nM. In total, there are nine PCC macrocyclic ligands (three for IDO1 Epitope1, four for IDO1 Epitope2, and two for IDO1 Epitope3).

Epitope-targeted macrocyclic peptide ligands against IDO1 were developed by in situ click screening of one-bead-one-compound (OBOC) peptide libraries. Screens were performed against human IDO1 epitopes that show high homology with mouse IDO1. These ligands were designed to bind to specific synthetic epitopes of IDO1, in a manner reminiscent of monoclonal antibodies (mAbs). Cyclic peptides have an ability to display protein-like epitopes with restricted conformational flexibility and thus often display enhanced bioavailability, increased stability towards metabolic degradation, and superior binding affinities as compared to their linear counterparts.

In some forms, the peptide library is composed of exclusively D-amino acids and artificial amino acids. IDO1 inhibitor, 1-methyl-Ltryptophan (Me-Trp), is added during synthesis of the library for increasing hits that recognize the IDO1 active site. In some forms, 4-fluoro-L-phenylalanine (F-Phe) is added during synthesis of the library for increasing cell penetration.

Two biligand strategies are pursued to achieve low nM to pM binding. Biligands can be developed by attaching a small molecule inhibitor to an epitope-targeted PCC macrocycle anchor. This approach takes advantage of a small molecule inhibitor which can add specificity and assist in cell penetration. Biligands can also be developed by joining together pairs of two epitope-targeted PCC macrocyclic peptide ligands using a chemical linker to promote cell penetration. Cell penetration and cellular activity studies of ligands and biligands are pursued with input from medicinal chemistry. The optimized, cell-penetrant PCCs display specific binding and in vivo pharmacokinetics compatible with imaging IDO1 in vivo using fluorine-18 PET. Separately, the PCCs are investigated as novel therapeutic compounds.

A. Definitions

In some forms, the term "IDO1" as used herein refers to human IDO1. In some forms, IDO1 comprises one of the following amino acid sequence or an amino acid sequence substantially identical to it.

```
1. Human IDO1 protein
                                           (SEQ ID NO: 42)
AHAMENSWTI  SKEYHIDEEV  GFALPNPQEN  LPDFYNDWMF

IAKHLPDLIE  SGQLRERVEK  LNMLSIDHLT  DHKSQRLARL

VLGCITMAYV  WGKGHGDVRK  VLPRNIAVPY  CQLSKKLELP

PILVYADCVL  ANWKKKDPNK  PLTYENMDVL  FSFRDGDCSK

GFFLVSLLVE  IAAASAIKVI  PTVFKAMQMQ  ERDTLLKALL

EIASCLEKAL  QVFHQIHDHV  NPKAFFSVLR  IYLSGWKGNP

QLSDGLVYEG  FWEDPKEFAG  GSAGQSSVFQ  CFDVLLGIQQ

TAGGGHAAQF  LQDMRRYMPP  AHRNFLCSLE  SNPSVREFVL

SKGDAGLREA  YDACVKALVS  LRSYHLQIVT  KYILIPASQQ

PKENKTSEDP  SKLEAKGTGG  TDLMNFLKTV  RSTTEKSLLK

EG

2. Mouse IDO1 protein
                                           (SEQ ID NO: 43)
ALSKISPTEG  SRRILEDHHI  DEDVGFALPH  PLVELPDAYS

PWVLVARNLP  VLIENGQLRE  EVEKLPTLST  DGLRGHRLQR

LAHLALGYIT  MAYVWNRGDD  DVRKVLPRNI  AVPYCELSEK

LGLPPILSYA  DCVLANWKKK  DPNGPMTYEN  MDILFSFPGG

DCDKGFFLVS  LLVEIAASPA  IKAIPTVSSA  VERQDLKALE

KALHDIATSL  EKAKEIFKRM  RDFVDPDTFF  HVLRIYLSGW

KCSSKLPEGL  LYEGVWDTPK  MFSGGSAGQS  SIFQSLDVLL

GIKHEAGKES  PAEFLQEMRE  YMPPAHRNFL  FFLESAPPVR

EFVISRHNED  LTKAYNECVN  GLVSVRKFHL  AIVDTYIMKP

SKKKPTDGDK  SEEPSNVESR  GTGGTNPMTF  LRSVKDTTEK

ALLSWP
```

As used herein, the term "mammal" includes humans and both domestic animals such as laboratory animals and household pets (e.g., cats, dogs, swine, cattle, sheep, goats, horses, rabbits), and non-domestic animals such as wildlife and the like.

The term "capture agent" as used herein refers to a composition that comprises one or more target-binding moieties, or ligands which specifically binds to a target protein via those target-binding moieties. Each target-binding moiety exhibits binding affinity for the target protein, either individually or in combination with other target-binding moieties. In some forms, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent. In some forms, capture agents comprising one or more peptide ligands that specifically bind IDO1 are also referred to as epitope-targeted macrocyclic peptide ligands against IDO1.

Reference to "capture agents" further refers to pharmaceutically acceptable salts thereof. "Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The capture agents described herein, or their pharmaceutically acceptable salts, may contain one or more asymmetric centers and may thus give rise to enantiomers, diastereomers, and other stereoisomeric forms that may be defined, in terms of absolute stereochemistry, as (R) or (S) or, as (D) or (L) for amino acids. The disclosed compositions and methods are meant to include all such possible isomers, as well as their racemic and optically pure forms. Optically active (+) and ( ), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G."

A "stereoisomer" refers to a compound made up of the same atoms bonded by the same bonds but having different three-dimensional structures, which are not interchangeable. The disclosed compositions and methods contemplates various stereoisomers and mixtures thereof and includes "enantiomers," which refers to two stereoisomers whose molecules are nonsuperimposeable mirror images of one another.

A "tautomer" refers to a proton shift from one atom of a molecule to another atom of the same molecule. The disclosed compositions and methods include tautomers of any said compounds.

The term "epitope" as used herein refers to a distinct molecular surface of a protein (e.g., IDO1). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, 0-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "artificial amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods. In some forms, artificial amino acids include 4-fluoro-L-phenylalanine (F-Phe) and 1-methyl-L-tryptophan (Me-Trp).

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

The term "imaging agent" refers to capture agents that have been labeled for detection. In some forms, imaging agents are isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$ $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to a pharmacologically important site of action. Certain isotopically-labelled disclosed imaging agents, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled imaging agents can generally be prepared by conventional techniques known to those skilled in the art or by processes analogous to those described in the Examples as set out below using an appropriate isotopically-labeled reagent in place of the non-labeled reagent previously employed.

The present disclosure is also meant to encompass the in vivo metabolic products of the disclosed imaging agents. Such products may result from, for example, the oxidation, reduction, hydrolysis, amidation, esterification, and the like of the administered compound, primarily due to enzymatic processes. Accordingly, disclosed are compounds produced by a process comprising administering a compound as disclosed to a mammal for a period of time sufficient to yield a metabolic product thereof. Such products are typically identified by administering a radiolabelled the disclosed compounds in a detectable dose to an animal, such as rat, mouse, guinea pig, monkey, or to human, allowing sufficient time for metabolism to occur, and isolating its conversion products from the urine, blood or other biological samples.

A "pharmaceutical composition" refers to a formulation of a compound as disclosed and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed binding agent may vary according to factors such as the disease state, age, sex, and weight of the individual, and the ability of the binding agent to elicit a desired response in the individual.

The term "stable" as used herein with regard to a binding agent, protein catalyzed capture agent, or pharmaceutical formulation thereof refers to the agent or formulation retaining structural and functional integrity for a sufficient period of time to be utilized in the methods described herein.

The term "synthetic" as used herein with regard to a protein catalyzed capture agent or binding agent refers to the binding agent having been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

B. Development of IDO1 Binding Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a binding agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>10$^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final binding agent can then be scaled up using relatively simple and largely automated chemistries, and it can be developed with a label, such as a biotin group, as an intrinsic part of its structure. This approach permits the exploration of branched, cyclic, and linear binding agent architectures. While many strategies for protein-directed multiligand assembly have been described, most require detailed structural information on the target to guide the screening strategy, and most (such as the original in situ click approach), are optimized for low-diversity small molecule libraries.

C. IDO1 Heterobiligands and Capture Agents

In one aspect, provided herein is a stable, synthetic capture agent that specifically binds IDO1, wherein the capture agent comprises one or more "anchor" ligands (also referred to as simply "ligands" herein) and a linker where there are one or more ligands, and wherein the ligands selectively bind IDO1. These are referred to herein as capture agents.

In some forms, a ligand comprises one or more polypeptides or peptides. In some forms, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted 1,2,3-triazole. In some forms, the ligand comprises a peptide comprising D-amino acids and artificial amino acids.

In some forms, the ligands are linked to one another via a covalent linkage through a linker. In some forms, the ligand and linker are linked to one another via an amide bond or a 1,4-disubstituted-1,2,3-triazole linkage as shown below:

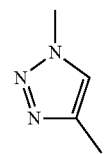

1,4-disubstituted-1,2,3-triazole linkage.

In those forms where the ligands and linker are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In some forms, the ligands and linker are linked to one another by a Tz4 linkage having the following structure:

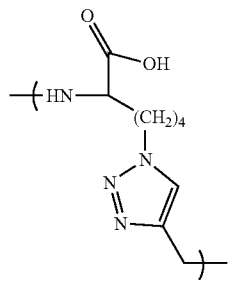

In some forms, the ligands and linker are linked to one another by a Tz5 linkage having the following structure:

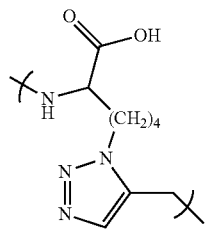

In those forms wherein one or more of the ligands and linker are linked to one another via amide bonds, the amide bond may be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In some forms, the capture agents provided herein are stable across a range of reaction conditions and/or storage times. A capture agent that is "stable" as used herein maintains the ability to specifically bind to a target protein. In some forms, the capture agents provided herein are more stable than an antibody binding to the same target protein under one or more reaction and/or storage conditions. For example, in some forms the capture agents provided herein are more resistant to proteolytic degradation than an antibody binding to the same target protein.

In some forms, the capture agents provided herein have a shelf-life of greater than six months, meaning that they are stable in storage for greater than six months. In some forms, the capture agents have a shelf-life of one year or greater, two years or greater, or more than three years. In some forms, the capture agents are stored as a lyophilized powder. In some forms, the capture agents provided herein have a longer shelf-life than an antibody binding to the same target protein.

In some forms, the capture agents provided herein are stable at temperatures ranging from about −80° to about 120° C. In some forms, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In some forms, the capture agents provided herein are stable across a wider range of temperatures than an antibody binding to the same target protein, and/or remain stable at a specific temperature for a longer time period than an antibody binding to the same target protein.

In some forms, the IDO1 capture agents provided herein are stable at a pH range from about 3.0 to about 8.0. In some forms, the range is about 4.0 to about 7.0. In some forms, the range is about 7.0 to about 8.0.

In some forms, the IDO1 capture agents provided herein are stable in human serum for more than 12 hours. In some forms, the capture agents are stable in human serum for more than 18 hours, more than 24 hours, more than 36 hours, or more than 48 hours. In some forms, the capture agents provided herein are stable for a longer period of time in human serum than an antibody binding to the same target protein. In some forms, the capture agents are stable as a powder for two months at a temperature of about 60° C.

In some forms, the IDO1 capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, 11C, $^{76}$Br, $^{123}$I $^{131}$I, $^{67}$Ga $^{111}$In and $^{99m}$Tc, or other radiolabeled products that may include gamma emitters, proton emitters, positron emitters, tritium, or covered tags detectable by other methods (i.e., gadolinium) among others. In some forms, the detection label is $^{18}$F. The capture agents may be used as diagnostic agents.

In some forms, the IDO1 capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In some forms, the capture agent may be modified by modifying the synthesis blocks of the target-binding moieties before the coupling reaction.

In some forms, the IDO1 capture agents provided herein are stable across a wide range of temperatures, pH values, storage times, storage conditions, and reaction conditions, and in some forms the imaging agents are more stable than a comparable antibody or biologic. In some forms, the capture agents are stable in storage as a lyophilized powder. In some forms, the capture agents are stable in storage at a temperature of about −80° C. to about 60° C. In some forms, the capture agents are stable at room temperature. In some forms, the capture agents are stable in human serum for at least 24 hours. In some forms, the capture agents are stable at a pH in the range of about 3 to about 12. In some forms, the capture agents are stable as a powder for two months at a temperature of about 60° C.

As shown in Example 9, tuning of heterobiligand capture agents can enhance, for example, binding to the target, inhibition, cellular penetration, and combinations of these. For example, incorporation of unnatural or modified amino acids can increase binding and/or cellular penetration. Deletion of amino acids in a hit peptide ligand can increase, for example, binding to the target, inhibition (deletions can also decrease these properties). Related to these, substitution of amino acids can increase, for example, binding to the target, inhibition. Alanine scanning of hit peptides is useful for identify amino acids that can be modified without reducing binding or other properties.

The length and composition of linkers can be tuned to optimize, for example, binding to the target, inhibition, cellular penetration, and combinations of these. For example, in addition to PEG linkers, all carbon (e.g., alkyl) linkers, linkers with mixtures of PEG and alkyl, peptide linkers, linkers with mixtures of PEG and peptides (amino acids), linkers with mixtures of alkyl and peptides (amino acids), and mixtures of PEG, alkyl, and amino acids can be used. In particular, inclusion of an alkyl on the end of the linker that couples to the small molecule inhibitor (or inclusion of an alkyl tail on the small molecule inhibitor for coupling to the linker) is useful for tuning the heterobiligand.

Methylation of amines in heterobiligands, preferably in the peptide ligand, but also in the linker, can increase cell penetration. Addition of a cell penetrating peptide sequence in the heterobiligand can increase cell penetration. Lipidating groups can be added to the heterobiligand, such as in the peptide ligand or in the linker, to increase lipophilicity of the heterobiligand. The closure (cyclization) of the peptide ligand can be accomplished using different chemistries and different groups. For example, triazole linkages can be used.

Combinations of these modifications (tunings) can be use to increase or modulate these effects.

D. Methods of Making/Screening Capture Agents

Provided herein in some forms are methods of screening target-binding moieties and/or making imaging agents that comprise these target-binding moieties. Methods for screening target-binding moieties and/or making imaging agents that comprise these target-binding moieties can also be found in International Publication Nos. WO 2012/106671, WO 2013/033561, WO 2013/009869 and WO 2014/074907, each of which is incorporated by reference, herein, in their entireties.

In some forms, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D=K_{D1} \times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

For developing a set of PCC binders against a target protein, first one or more PCCs that bind an epitope on the target protein are identified. Optionally, one or more different PCCs binding to a second epitope are identified. Additional PCCs that bind to a third, fourth, etc., epitope may be useful as well. The epitope targeted PCC method teaches that this may be accomplished by screening peptide libraries against synthetic epitopes (SynEps). A SynEp is a polypeptide that has the sequence of the naturally occurring target epitope, except that one position contains an artificial amino acid that presents an azide or acetylene chemical group, called a click handle. The SynEp is further modified to contain an assay handle, such as a biotin group, at the N- or C-terminus. The screening procedure can be done using any procedure disclosed herein or known in the art. By screening, one identifies at least one unique peptide binder to each of at least two epitopes on the target. Those peptide binders are validated via carrying out binding assays against the full protein target as well as against the SynEps. For those binding assays, the SynEps are prepared with the naturally occurring residue in place of the click handle.

Ideally, the different regions of the target protein to which the different ligands bind will be relatively close together (a few nanometers or less) in the tertiary protein structure. For even a single SynEp, a screen can produce PCCs that bind to two different sites. During the SynEp screening steps, PCCs that bind to the N-terminal side of the epitope or the C-terminal side may both be identified.

Once the epitope targeted PCCs are identified, there are several methods for selecting a linker.

In a first method, if the folded structure of the protein is known, and if the PCCs bind to that folded structure, then one can use that information, plus knowledge of which PCCs bind to which epitopes, to estimate an optimal linker length. Analysis of the binding arrangement, together with the structure of the protein from, for example, the Protein Data Bank, permits an estimate of the length of an optimized linker. Such an estimate can narrow down the choice of candidate linkers to a very small number. One example might be to use such a length estimate to select one or two length-matched polyethylene glycol oligomers for testing. The best linker is the one that brings the biligand affinity closest to that a fully cooperative binder.

In a second method, if the folded structure of the protein is not known, or if the protein simply does not have a well-defined folded structure, then one uses as much information as is available to determine the composition of a library of candidate linker molecules. That library is then screened to identify a best linker.

In a third method, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In some forms, linkers can include polyethyelene glycol (PEG), alkane, alkene, triazole, amide, or peptides.

E. In Vitro

For detection of IDO1 in solution, a binding or capture agent as described herein can be detectably labeled to form an imaging agent, then contacted with the solution, and thereafter formation of a complex between the imaging agent and the IDO1 target can be detected. As an example, a fluorescently labeled imaging agent can be used for in vitro IDO1 detection assays, wherein the imaging agent is added to a solution to be tested for IDO1 under conditions allowing binding to occur. The complex between the fluorescently labeled imaging agent and the IDO1 target can be detected and quantified by, for example, measuring the increased fluorescence polarization arising from the complex-bound peptide relative to that of the free peptide.

Alternatively, a sandwich-type "ELISA" assay can be used, wherein a imaging agent is immobilized on a solid support such as a plastic tube or well, then the solution suspected of containing IDO1 is contacted with the immobilized binding moiety, non-binding materials are washed away, and complexed polypeptide is detected using a suitable detection reagent for recognizing IDO1.

For detection or purification of soluble IDO1 from a solution, imaging agents as disclosed can be immobilized on a solid substrate such as a chromatographic support or other matrix material, then the immobilized binder can be loaded or contacted with the solution under conditions suitable for formation of an imaging agent/IDO1 complex. The non-binding portion of the solution can be removed and the complex can be detected, for example, using an anti-IDO1 antibody, or an anti-binding polypeptide antibody, or the IDO1 can be released from the binding moiety at appropriate elution conditions.

F. In Vivo Diagnostic Imaging

A particularly preferred use for the disclosed imaging agents is for creating visually readable images of IDO1 or IDO1-expressing cells in a biological fluid, such as, for example, in human serum. The IDO1 imaging agents disclosed herein can be conjugated to a label appropriate for diagnostic detection. Preferably, an imaging agent exhibiting much greater specificity for IDO1 than for other serum proteins is conjugated or linked to a label appropriate for the detection methodology to be employed. For example, the imaging agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In some forms, rather than directly labeling an imaging agent with a detectable label or radiotherapeutic construct, one or more of the disclosed peptides or constructs can be conjugated with for example, avidin, biotin, or an antibody or antibody fragment that will bind the detectable label or radiotherapeutic.

1. Magnetic Resonance Imaging

The IDO1 imaging agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolysis of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7,-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-CI-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N"-tris(2,3-dihydroxybenzoyl)-tricatecholate (LICAM); and 1,3,5-N,N',N"-tris(2,3-dihydroxybenzoyl)aminomethylbenzene (MECAM). A preferred chelator is DTPA, and the use of DO3A is particularly preferred. Examples of representative chelators and chelating groups that can be used in the disclosed compositions and methods are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present disclosure, the chelator of the MRI contrast agent is coupled to the IDO1 imaging agent. The positioning of the chelate should be selected so as not to interfere with the binding affinity or specificity of the IDO1 imaging agent. The chelate also can be attached anywhere on the imaging agent.

In general, the IDO1 imaging agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the IDO1 binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly (vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the disclosed imaging reagents. Depending on their location within the linker, such biodegradable functionalities can include ester, double ester, amide, phosphoester, ether, acetal, and ketal functionalities.

In general, known methods can be used to couple the metal chelate and the IDO1 imaging agent using such linkers (WO 95/28967, WO 98/18496, WO 98/18497 and discussion therein). The IDO1 binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between IDO1-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging IDO1-expressing tissues, such as tumors, intravenous or intraarterial administration is preferred. For MRI, it is contemplated that the subject will receive a dosage of contrast agent sufficient to enhance the MR signal at the site IDO1 expression by at least 10%. After injection with the IDO1 imaging agent containing MRI reagent, the patient is scanned in the MRI machine to determine the location of any sites of IDO1 expression. In therapeutic settings, upon identification of a site of IDO1 expression (e.g., fluid or tissue), an anti-cancer agent (e.g., inhibitors of IDO1) can be immediately administered, if necessary, and the patient can be subsequently scanned to visualize viral load.

2. Nuclear Imaging (Radionuclide Imaging) and Radiotherapy

The disclosed IDO1 imaging agents can be conjugated with a radionuclide reporter appropriate for scintigraphy, SPECT, or PET imaging and/or with a radionuclide appropriate for radiotherapy. Constructs in which the IDO1 imaging agents are conjugated with both a chelator for a radionuclide useful for diagnostic imaging and a chelator useful for radiotherapy are specifically contemplated.

For use as a PET agent a disclosed imaging agent may be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The disclosed binding moieties can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Tb, $^{166}$Dy, $^{166}$Ho, $^{175}$Yb, $^{177}$Ln, $^{186/188}$Re, and $^{199}$Au. $^{99m}$Tc is useful for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to IDO1 imaging agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S.

Pat. Nos. 5,183,653; 5,387,409; and 5,118,797, the disclosures of which are incorporated by reference herein, in their entirety.

The chelators can be covalently linked directly to the IDO1 imaging agent via a linker, as described previously, and then directly labeled with the radioactive metal of choice (see, WO 98/52618, U.S. Pat. Nos. 5,879,658, and 5,849,261).

IDO1 imaging agents comprising $^{18}$F, 4-[$^{18}$F]fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the disclosed reagents, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a disclosed reagent to be labeled and a sufficient amount of reducing agent to label the reagent with $^{99m}$Tc. Alternatively, the complex can be formed by reacting a disclosed peptide conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the disclosed compositions and methods are included the alkali metal salts such as the sodium salt, or ammonium salts or lower alkyl ammonium salts.

Preparation of the disclosed complexes where the metal is radioactive rhenium can be accomplished using rhenium starting materials in the +5 or +7 oxidation state. Examples of compounds in which rhenium is in the Re(VII) state are NH$_4$ReO$_4$ or KReO$_4$. Re(V) is available as, for example, [ReOCl$_4$](NBu$_4$), [ReOCl$_4$](AsPh$_4$), ReOCl$_3$(PPh$_3$)$_2$ and as ReO$_2$(pyridine)$_4^+$, where Ph is phenyl and Bu is n-butyl. Other rhenium reagents capable of forming a rhenium complex also can be used.

Also disclosed are radioactively labeled PET, SPECT, or scintigraphic imaging agents that have a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled IDO1 imaging agent can provide 10-20 mCi. After injection of the radionuclide-labeled IDO1 imaging agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the disclosed radiotherapeutic compounds are known to those skilled in the art. The compounds can be administered using many methods including, but not limited to, a single or multiple IV or IP injections, using a quantity of radioactivity that is sufficient to cause damage or ablation of the targeted IDO1-expressing tissue, but not so much that substantive damage is caused to non-target (normal tissue). The quantity and dose required is different for different constructs, depending on the energy and half-life of the isotope used, the degree of uptake and clearance of the agent from the body and the mass of the IDO1-expressing tissue. In general, doses can range from a single dose of about 30-50 mCi to a cumulative dose of up to about 3 Ci.

The disclosed radiotherapeutic compositions can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

Also disclosed are single or multi-vial kits that contain all of the components needed to prepare the disclosed complexes, other than the radionuclide.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γcyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the disclosed complexes are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an IDO1 imaging agent. In some forms, 4-[$^{18}$F]fluorobenzaldehyde ($^{18}$FB) is conjugated onto an imaging agent bearing an aminooxy moiety, resulting in oxime formation. In some forms, [$^{18}$F]fluorobenzaldehyde is conjugated onto an imaging agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled imaging agents can also be prepared from imaging agents possessing thiosemicarbazide moieties under conditions that promote formation of a thiosemicarbozone, or by use of a $^{18}$F-labeled aldehyde bisulfite addition complex.

The above methods are particularly amenable to the labeling of imaging agents, e.g., the imaging agents described herein, which can be modified during synthesis to contain a nucleophilic hydroxylamine, thiosemicarbazide or hydrazine (or acyl hydrazide) moiety that can be used to react with the labeled aldehyde. The methods can be used for any imaging agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step may be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water may be added to a mixture of Kryptofix and K$_2$CO$_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters®. Oasis HLB LP extraction cartridge. The cartridge may be washed with 9:1 water:acetonitrile and water to remove unbound $^{18}$F and unreacted 4-trimethylammoniumbenzaldehyde triflate. The 4-[$^{18}$F] fluorobenzaldehyde may then be eluted from the cartridge with methanol in fractions.

G. Therapeutic Applications

Provided herein in some forms are methods of using the IDO1 binding and capture agents disclosed herein to identify, detect, quantify, and/or separate IDO1 in a biological sample. In some forms, these methods utilize an immunoassay, with the capture agent replacing an antibody or its equivalent. In some forms, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in some forms are methods of using the IDO1 imaging agents disclosed herein to diagnose and/or classify (e.g., stage) a condition associated with IDO1 expression. In some forms, the methods comprise (a) obtaining a biological sample from a subject; (b) measuring the presence or absence of IDO1 in the sample with the IDO1 imaging agent; (c) comparing the levels of IDO1 to a predetermined control range for IDO1; and (d) diagnosing a condition associated with IDO1 expression based on the difference between IDO1 levels in the biological sample and the predetermined control.

In some forms, the IDO1 capture agents disclosed herein are used as a mutant specific targeted therapeutic. In some forms, the IDO1 capture agent is administered alone without delivering DNA, a radiopharmaceutical or another active agent.

The IDO capture agents described herein also can be used to target genetic material to IDO1 expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In some forms, the disclosed capture agents are utilized in gene therapy. In some forms, genetic material, or one or more delivery vehicles containing genetic material can be conjugated to one or more IDO1 capture agents of this disclosure and administered to a patient.

Therapeutic agents and the IDO1 capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and IDO1 binding polypeptide can be coexpressed from the same synthetic gene, created using recombinant DNA techniques, as described above. The coding sequence for the IDO1 binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the IDO1 binding polypeptide. A particular advantage of this general approach is that concatamerization of multiple, tandemly arranged IDO1 capture agents is possible, thereby increasing the number and concentration of IDO1 binding sites associated with each therapeutic protein. In this manner, IDO1 binding avidity is increased, which would be expected to improve the efficacy of the recombinant therapeutic fusion protein.

A residue of a monomer unit or moiety refers to the portion of the monomer or moiety that is the resulting product of the monomer unit or moiety in a particular reaction scheme or subsequent formulation or chemical product, regardless of whether the portion of the monomer or moiety is actually obtained from the monomer unit or moiety. Thus, an ethylene glycol residue in a polyester refers to one or more —OCH$_2$CH$_2$O— units in the polyester, regardless of whether ethylene glycol was used to prepare the polyester. Similarly, an amino acid residue in a peptide refers to one or more —CO—CHR—NH— moieties in the polyester, regardless of whether the residue is obtained by reacting the amino acid to obtain the peptide.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. Peptide as used herein includes oligomers of amino acids and small and large peptides, including polypeptides.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist." One that decreases, or prevents, a known activity is an "antagonist."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition. The disclosed compositions and methods can be further understood through the following numbered paragraphs.

1. A heterobiligand comprising a first ligand having affinity for an epitope on indoleamine 2,3-dioxygenase 1 (IDO1), a linker, and a second ligand, wherein the second ligand comprises a small molecule inhibitor of IDO1, wherein the linker links the first ligand and the second ligand, wherein the heterobiligand specifically binds and inhibits IDO1, wherein IDO1 comprises an active site, wherein the first ligand comprises a 3-10 amino acid sequence of D-amino acids, artificial amino acids, or combinations thereof, and wherein the small molecule inhibitor of IDO1 binds the IDO1 active site.

2. The heterobiligand of paragraph 1, wherein the small molecule inhibitor of IDO1 binds the heme at the IDO1 active site.

3. The heterobiligand of paragraph 1 or 2, wherein the small molecule inhibitor of IDO1 is

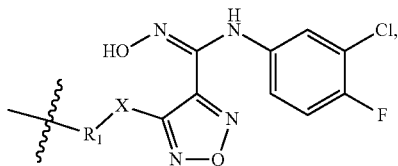

wherein X is S, O, or NH, wherein $R_1$ is —$CH_2$—$R_2$—, —$(CH_2)_n$—$R_2$—, absent, —$(CH_2$—$CH_2$—$O)_m$—$CH_2$—$CH_2$—$R_2$—, or —$CH_2$—$CH_2$—NH—$SO_2$—$R_2$—, wherein $R_2$ is —CO— or —NH—, wherein n is an integer from 2 to 10, wherein m is an integer from 1 to 6.

4. The heterobiligand of any one of paragraphs 1-3, wherein the small molecule inhibitor of IDO1 is

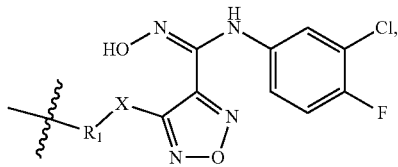

wherein X is S, wherein $R_1$ is —$CH_2$—$R_2$—, and wherein $R_2$ is —CO—.

5. The heterobiligand of any one of paragraphs 1-3, wherein the small molecule inhibitor of IDO1 is

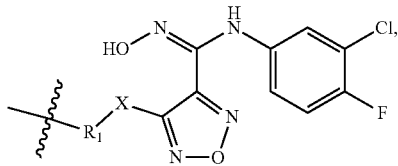

wherein X is NH, and wherein $R_1$ is absent.

6. The heterobiligand of any one of paragraphs 1-3, wherein the small molecule inhibitor of IDO1 is

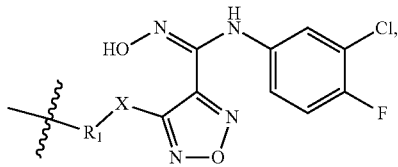

wherein X is NH, wherein $R_1$ is —$CH_2$—$CH_2$—NH—$SO_2$—$R_2$—, and wherein $R_2$ is —NH—.

7. The heterobiligand of any one of paragraphs 1-6, wherein the first ligand comprises 5 to 9 amino acids.

8. The heterobiligand of any one of paragraphs 1-7, wherein the epitope comprises the amino acid sequence GFWEDPKEFAGGSAGQSSVFQ (SEQ ID NO:1).

9. The heterobiligand of any one of paragraphs 1-8, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t(Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), yfn(Me-Trp)(Me-Trp) (SEQ ID NO:19), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

10. The heterobiligand of any one of paragraphs 1-9, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t(Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), and yfn(Me-Trp)(Me-Trp) (SEQ ID NO:19)

11. The heterobiligand of any one of paragraphs 1-10, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), and frf(Me-Trp)s (SEQ ID NO:7).

12. The heterobiligand of any one of paragraphs 1-11, wherein the first ligand comprises an amino acid sequence wyvay (SEQ ID NO:2) or wyray (SEQ ID NO:3).

13. The heterobiligand of any one of paragraphs 1-12, wherein the first ligand comprises an amino acid sequence wyvay (SEQ ID NO:2).

14. The heterobiligand of any one of paragraphs 1-12, wherein the first ligand does not comprise an amino acid sequence selected from the group consisting of wyray (SEQ ID NO:3), wyry (SEQ ID NO:4), nsfr(Me-Trp) (SEQ ID NO:6), frf(Me-Trp)s (SEQ ID NO:7), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

15. The heterobiligand of any one of paragraphs 1-14, wherein the first ligand comprises a 1,4-substituted-1,2,3-triazole residue (Tz4) or a 1,5-substituted-1,2,3-triazole residue (Tz5).

16. The heterobiligand of any one of paragraphs 1-15, wherein the triazole residue is a 1,4-substituted-1,2,3-triazole (Tz4) residue.

17. The heterobiligand of any one of paragraphs 1-16, wherein the length of the linker is from about 11 Å to about 38 Å.

18. The heterobiligand of any one of paragraphs 1-17, wherein the heterobiligand further comprises a detectable moiety.

19. The heterobiligand of paragraph 18, wherein the detectable moiety is selected from the group consisting of biotin, copper-DOTA, biotin-PEG$_3$, aminooxyacetate, $^{19}$FB, $^{18}$FB, and FITC-PEG$_3$.

20. The heterobiligand of paragraph 18 or 19, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, 124I, $^{86}$Y, $^{94m}$Tc, $^{110m}$In, $^{11}$C and $^{76}$Br.

21. The heterobiligand of any one of paragraphs 18-20, wherein the detectable moiety is $^{18}$F.

22. A composition comprising a first ligand having affinity for an epitope on indoleamine 2,3-dioxygenase 1 (IDO1), a linker, and an E3 ligase ligand, wherein the linker links the first ligand and the E3 ligase ligand, wherein the composition specifically binds IDO1.

23. The composition of paragraph 22, wherein the first ligand comprises a 3-10 amino acid sequence of D-amino acids, artificial amino acids, or combinations thereof.

24. The composition of paragraph 22 or 23, wherein the first ligand comprises 5 to 9 amino acids.

25. The composition of any one of paragraphs 22-24, wherein the epitope comprises the amino acid sequence LPPILVYADCVLANWKKKDPNK (SEQ ID NO:24).

26. The composition of any one of paragraphs 22-25, wherein the first ligand comprises an amino acid sequence selected from the group consisting of rys(Me-Trp)r (SEQ ID NO:25), X41f(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:26 and 27), nlw(Me-Trp)r (SEQ ID NO:28), and sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present (SEQ ID NOs:29 and 30).

27. The composition of any one of paragraphs 22-26, wherein the first ligand comprises an amino acid sequence of nlf(Me-Trp)(F-Phe) (SEQ ID NO:31), alf(Me-Trp)(F-Phe) (SEQ ID NO:32), or lf(Me-Trp)(F-Phe) (SEQ ID NO:27).

28. The composition of any one of paragraphs 22-26, wherein the first ligand comprises an amino acid sequence of spww(F-Phe) (SEQ ID NO:33), saww(F-Phe) (SEQ ID NO:34), or sww(F-Phe) (SEQ ID NO:35).

29. The composition of any one of paragraphs 22-24, wherein the epitope comprises the amino acid sequence NKPLTYENMDVLFSFR (SEQ ID NO:36).

30. The composition of any one of paragraphs 22-24 or 29, wherein the first ligand comprises an amino acid sequence selected from the group consisting of rffyl (SEQ ID NO:37) and nsh(F-Phe)r (SEQ ID NO:38).

31. The composition of any one of paragraphs 22-24, wherein the epitope comprises the amino acid sequence GFWEDPKEFAGGSAGQSSVFQ (SEQ ID NO:1).

32. The composition of any one of paragraphs 22-24 or 31, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t (Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), yfn(Me-Trp)(Me-Trp) (SEQ ID NO:19), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

33. The composition of any one of paragraphs 22-24, 31, or 32, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), frf(Me-Trp)s (SEQ ID NO:7), wyaay (SEQ ID NO:8), (F-Phe)rhl(Me-Trp) (SEQ ID NO:9), (F-Phe)t (Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO:14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), and yfn(Me-Trp)(Me-Trp) (SEQ ID NO:19).

34. The composition of any one of paragraphs 22-24 or 31-33, wherein the first ligand comprises an amino acid sequence selected from the group consisting of wyvay (SEQ ID NO:2), wyray (SEQ ID NO:3), wyry (SEQ ID NO:4), (F-Phe)n(Me-Trp)(Me-Trp)w (SEQ ID NO:5), nsfr(Me-Trp) (SEQ ID NO:6), and frf(Me-Trp)s (SEQ ID NO:7).

35. The composition of any one of paragraphs 22-24 or 31-34, wherein the first ligand comprises an amino acid sequence wyvay (SEQ ID NO:2) or wyray (SEQ ID NO:3).

36. The composition of any one of paragraphs 22-24 or 31-35, wherein the first ligand comprises an amino acid sequence wyvay (SEQ ID NO:2).

37. The composition of any one of paragraphs 22-24 or 31-35, wherein the first ligand does not comprise an amino acid sequence selected from the group consisting of wyray (SEQ ID NO:3), wyry (SEQ ID NO:4), nsfr(Me-Trp) (SEQ ID NO:6), frf(Me-Trp)s (SEQ ID NO:7), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), and rf(Me-Trp).

38. The composition of any one of paragraphs 22-37, wherein the first ligand comprises a 1,4-substituted-1,2,3-triazole residue (Tz4) or a 1,5-substituted-1,2,3-triazole residue (Tz5).

39. The composition of any one of paragraphs 22-38, wherein the triazole residue is a 1,4-substituted-1,2,3-triazole (Tz4) residue.

40. The composition of any one of paragraphs 22-39, wherein the length of the linker is sufficient to allow the E3 ligase ligand to recruit E3 ligase to IDO1 in proximity to a lysine residue on IDO1 when the composition is bound to IDO1.

41. The composition of any one of paragraphs 22-39, wherein the length of the linker is from about 11 Å to about 38 Å.

42. The composition of any one of paragraphs 22-41, wherein the composition further comprises a detectable moiety.

43. The composition of paragraph 42, wherein the detectable moiety is selected from the group consisting of biotin, copper-DOTA, biotin-PEG$_3$, aminooxyacetate, $^{19}$FB, $^{18}$FB, and FITC-PEG$_3$.

44. The composition of paragraph 42 or 43, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, 124I, $^{86}$Y, $^{94m}$Tc, $^{110m}$In, $^{11}$C and $^{76}$Br.

45. The composition of any one of paragraphs 42-44, wherein the detectable moiety is $^{18}$F.

46. A method of detecting IDO1 in a biological sample, comprising contacting the biological sample with the heterobiligand of any one of paragraphs 18-21 or the composition of any one of paragraphs 42-45.

47. The method of paragraph 46, further comprising binding IDO1 to the heterobiligand or composition, and detecting the detectable moiety linked to the heterobiligand or composition.

48. A method of reducing IDO1 enzymatic activity comprising contacting IDO1 with an effective amount of the heterobiligand of any one of paragraphs 18-21 or the composition of any one of paragraphs 42-45, thereby reducing IDO1 enzymatic activity.

49. The method of paragraph 48, wherein the IDO1 is contacted with an effective amount of the heterobiligand of any one of paragraphs 18-21.

50. A method of detecting IDO1 comprising contacting IDO1 with an effective amount of the heterobiligand of any one of paragraphs 18-21 or the composition of any one of paragraphs 42-45.

51. The method of any one of paragraphs 44-50, wherein the IDO1 is located in the cytosol of an intact cell.

EXAMPLES

Example 1: IDO1 Epitope Design

Figure 1B:
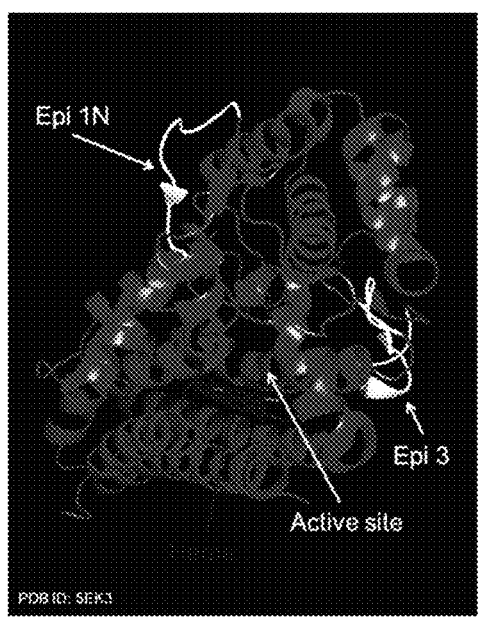

Using the crystal structure of human IDO1 (PDB ID: 5EK3), two epitopes (IDO1 Epitope1 and IDO1 Epitope2) were identified in the heme-containing active site of IDO1, which would serve as good candidates for Synthetic Epitope Targeting (FIG. 1A). These two epitopes are located within 11 to 38 Å of each other near the active site of IDO1. An additional epitope (IDO1 Epitope3) that is located on the other side of the IDO1 protein from Epitope1N was designed against the protein surface (FIG. 1B). They were deemed suitable epitopes for PCC agent development based on the following criteria:

Epitope is a continuous sequence (8 to 30 amino acids).
Epitope occurs in a region of the protein that is accessible in the native folded structure.
Epitopes are separated by short distances.
High homologies are demonstrated between the human and mouse IDO1 sequences.

The sequences of IDO1 Epitope1, IDO1 Epitope2, and IDO1 Epitope3 are:

```
Mouse IDO1
GVWDTPKMFSGGSAGQSSIFQ (a.a. 255-275)
(amino acids 3-23 of SEQ ID NO: 66)

Human IDO1
                                    (SEQ ID NO: 1)
GFWEDPKEFAGGSAGQSSVFQ (a.a. 251-271)

Epitope 1
                                    (SEQ ID NO: 39)
GFWEDPKE[F→Az4]AGGSAGQSSVFQ
```

```
Mouse IDO1
LPPILSYADCVLANWKKKDPNG (a.a. 124-145)
(amino acids 123-144 of SEQ ID NO: 43)

Human IDO1
                                    (SEQ ID NO: 24)
LPPILVYADCVLANWKKKDPNK (a.a. 120-141)

Epitope 2
                                    (SEQ ID NO: 40)
LPPILVYADCV[L→Az4]ANWKKKDPNK Mouse IDO1
NGPMTYENMDILFSFP (a.a. 144-159)
(amino acids 143-158 of SEQ ID NO: 43)

Human IDO1
                                    (SEQ ID NO: 36)
NKPLTYENMDVLFSFR (a.a. 140-155)

Epitope 3
                                    (SEQ ID NO: 41)
NKPLTYENM[D→Az4]VLFSFR
```

An azide click handle (Az4) is substituted at the bracketed amino acid positions. The high homology between the human and mouse IDO1 proteins was leveraged to design epitopes lying in the overlapping region. The primary sequences of human and mouse IDO1 show 62.5% identity (83.8% similarity) in 395 a.a. overlap.

Each epitope was synthesized to include an azide click handle (Az4=L-azidolysine) at a selected internal amino acid location. For IDO1 Epitope3, the D149Az4 substitution was made as it is located in the middle of the exposed loop of interest. For IDO1 Epitope1 and Epitope2, the F259Az4 and L131Az4 substitutions were made because they are adjacent to the residues key to substrate binding. The active site residues of G262-A264 (IDO1 Epitope1) and Y126-V130 (IDO1 Epitope2) are italicized above. Because the azide click handle was installed as a centrally located residue, screening each epitope could yield two sets of epitope-targeted macrocyclic peptide ligands—one set pointing towards the N-terminus and another set pointing towards the C-terminus of the epitope. Epitopes 1C and 2N contain residues forming the active site pockets, while the Epitopes 1N and 2C can be found on the surface of the IDO1 protein.

Example 2: Screening a Macrocycle Library Against IDO1 Epitopes 1, 2, and 3

Screens were performed against human IDO1 epitopes that show high homology with mouse IDO1 with the goal of identifying leads that show equivalent binding to the human and mouse IDO1 proteins. The library was composed exclusively of amino acids with D-chirality and artificial amino acids, and contained all possible combinations of pentapeptide (5-mer) sequences in the variable region. Standard Fmoc-amino acid coupling chemistries and solid-phase synthesis were used. The diversity of the macrocycle D-amino acid library was expanded by including 4-fluoro-L-phenylalanine (F-Phe) to assist in cell penetration and 1-methyl-L-tryptophan (Me-Trp) to help in biasing the screen towards hits that recognize the IDO1 active site.

Screens were performed using a triazole-cyclized OBOC library of the form H$_2$N-Pra-Cy(XXXXX-click)-(D-Met)-TG, where TG=TENTAGEL® S NH$_2$ resin (S 30 902, Rapp Polymere), Pra=L-propargylglycine (alkyne click handle), D-Met=D-methionine, and X=one of sixteen D-amino acids (D-Ala, D-Arg, D-Asn, D-Asp, D-Glu, Gly, D-His, D-Leu, D-Lys, D-Phe, D-Pro, D-Ser, D-Thr, D-Trp, D-Tyr, D-Val), 4-fluoro-L-phenylalanine (F-Phe), or 1-methyl-L-tryptophan (Me-Trp). The notation Cy(XXXXX-click) indicates that macrocycles were closed using Cu-catalyzed azide-alkyne cycloaddition (CuAAC). Macrocycles were identified against the three synthesized IDO1 epitopes in a five-step screening process: 1) a pre-clear to eliminate non-specific binders, 2) a product screen to identify hits resulting from IDO1 Epitope1-templated in situ click chemistry, 3) another product screen to identify hits resulting from IDO1 Epitope2-templated in situ click chemistry, 4) a further product screen to identify hits resulting from IDO1 Epitope3-templated in situ click chemistry, and 5) a target screen against His-tagged IDO1 human recombinant protein to identify peptides that bind to the protein as well as the epitopes.

Pre-clear. Swelled library beads (750 mg) were blocked overnight with Blocking Buffer (25 mM Tris-HCl, 150 mM NaCl, 1% (w/v) BSA, and 0.05% (v/v) TWEEN® 20, pH 7.6) at 4° C., then washed with Blocking Buffer three times. A 1:10,000 dilution of Streptavidin-Alkaline Phosphatase (V559C, Promega) and 1:10,000 dilution of Anti-6×HIS TAG® antibody [HIS-1](Alkaline Phosphatase-conjugated) (ab49746, Abcam) in 4 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM MgCl2, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in 1-methyl-2-pyrrolidinone (NMP) overnight to decolorize.

Product Screen with IDO1 Epitope1. Beads remaining from the pre-clear were washed with water ten times and TBS three times. Beads were then incubated with 3 mL of 100 µM IDO1 Epitope1 fragment (Biotin-PEG3-GFWEDPKE[Az4]AGGSAGQSSVFQ (SEQ ID NO:39)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits and separately the non-hits were treated with 7.5 M guanidine hydrochloride pH 2.0 for 30 min to remove attached streptavidin, washed ten times with water, and incubated in NMP overnight to decolorize.

Product Screen with IDO1 Epitope2. The hits and separately the non-hit beads obtained from the previous product screen were washed with water ten times and TBS three times. The non-hit beads were then incubated with 3 mL of 100 µM IDO1 Epitope2 fragment (Biotin-PEG3-LPPILVY-ADCV[Az4]ANWKKKDPNK (SEQ ID NO:40)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits were treated with 7.5 M guanidine hydrochloride pH 2.0 for 30 min to remove attached streptavidin, washed ten times with water, and incubated in NMP overnight to decolorize.

Product Screen with IDO1 Epitope3. The hits and separately the non-hit beads obtained from the previous product screen were washed with water ten times and TBS three times. The non-hit beads were then incubated with 3 mL of 100 µM IDO1 Epitope3 fragment (Biotin-PEG3-NKPLTY-ENM[Az4]VLFSFR (SEQ ID NO:41)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits were treated with 7.5 M guanidine hydrochloride pH 2.0 for 30 min to remove attached streptavidin, washed ten times with water, and incubated in NMP overnight to decolorize.

Target Screen with His-tagged IDO1 Protein. The hits obtained from the third product screen were washed with water ten times and TBS three times. Next, the hits isolated for IDO1 Epitope1, Epitope2, and Epitope3 were transferred to three CORNING® 8162 COSTAR® SPIN-X® centrifuge tube filters (cellulose acetate membrane) and incubated with Blocking Buffer for 3 h at room temperature. The beads were rinsed three times with Blocking Buffer and then incubated with 150 nM of His-tagged IDO1 human recombinant protein (71182, BPS Biosciences) in Blocking Buffer (preparation: 5.8 µL His-tagged IDO1 human recombinant protein in 642 µL Blocking Buffer) for 1 h at room temperature. The beads were washed three times with Blocking Buffer and then incubated with 500 µL of 1:10,000 Anti-6× HIS TAG® antibody [HIS-1](Alkaline Phosphatase-conjugated) (ab49746, Abcam) in Blocking Buffer for 1 h at room temperature. The beads were subsequently washed with 3×500 µL Blocking Buffer, 3×500 µL TBS, then 3×500 µL Alkaline Phosphatase (pH 9) buffer (centrifuging at 7000 rpm for 30 sec after each wash). After this, the beads were developed with BCIP/NBT for 10 min. Purple hit beads bound to IDO1 protein were selected by pipet and saved. The target hits for IDO1 Epitope1, Epitope2, and Epitope3 were treated with 7.5 M guanidine hydrochloride pH 2.0 for 30 min to remove bound proteins, washed ten times with water, and incubated in NMP overnight to decolorize. The hits were finally washed with water ten times to prepare for sequencing analysis.

Example 3: Sequencing Cyclic Peptide Hits by MALDI-TOF/TOF

1. Manual Edman Degradation.

The process is shown with chemical structures below. Edman steps were adapted from Klemm *Methods Mol. Biol.* 1984.

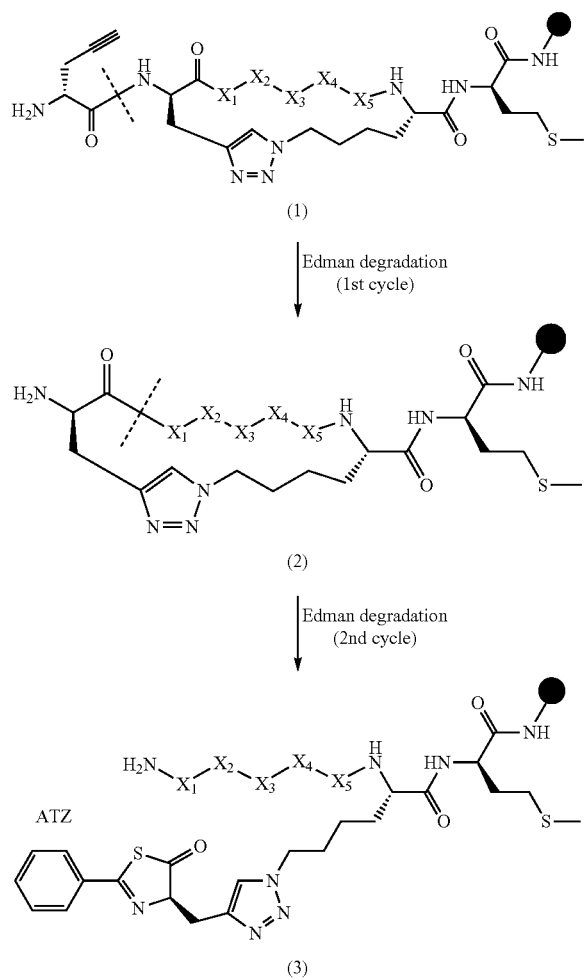

Preparing Cyclic Peptide Hits for MALDI-TOF/TOF Sequencing.
(1) Triazole-cyclized hit bead of the form $H_2N$-Pra-Cy (XXXXX-click)-(D-Met)-TG.
(2) Bead after 1st manual Edman degradation step.
(3) Bead after 2nd manual Edman degradation step. The resultant linear ATZ-peptide is of a form compatible with MALDI-TOF/TOF sequencing.

Cycle 1 (to remove the Pra click handle): Cyclic peptide hits were transferred in 5-10 μL water into a 10×75 mm Pyrex tube. The coupling reaction was initiated by adding 50 μL phenylisothiocyanate (2.5% (v/v) in 50% aq. pyridine) to the beads. The tube was flushed with $N_2$ (g) for 10 s, sealed with a rubber stopper, and allowed to react for 20 min at 50° C. The solution was washed once with 300 μL heptane:ethyl acetate (10:1). The tube was centrifuged at 500 rpm for 30 s, and the organic layer was removed by pipet (being careful to not disturb the beads at the bottom of the tube). The solution was then washed once with 300 μL heptane:ethyl acetate (1:2). The tube was centrifuged at 500 rpm for 30 s, and again the organic layer was removed by pipet. The remaining solution in the tube was dried under centrifugal vacuum at 60° C. for 10 min. The cleavage reaction was initiated by adding 50 μL trifluoroacetic acid (TFA) to the beads. The tube was flushed with $N_2$ (g) for 10 s, lightly covered with a rubber stopper, and allowed to react for 10 min at 45° C. The TFA was then removed by centrifugal vacuum for 10 min. The tube was then placed in an ice bath. Pyridine (50 μL) was added, and the solution was washed three times with 250 μL ice-cold n-butyl acetate saturated with water. The remaining solution (containing the beads) was then dried under centrifugal vacuum at 60° C. for 15 min.

Cycle 2 (ring opening): Beads were taken up in 10 μL water and allowed to re-equilibrate. The coupling and cleavage reactions were performed again (following the same protocol as Cycle 1). The resulting beads containing the linear anilinothiazolinone (ATZ)-peptide were taken up in 200 μL water and allowed to re-equilibrate overnight at room temperature. On the next day, beads were transferred to a CORNING® 8170 COSTAR® SPIN-X® centrifuge tube filter (nylon membrane) and washed with 10×500 μL water by centrifuge (30 s, 7000 rpm).

2. Cleavage of Hit Peptides from Single Beads with Cyanogen Bromide (CNBr).

Following the manual Edman degradation, each hit bead was transferred to a microcentrifuge tube containing pure water (10 μL). After addition of CNBr (10 μL, 0.50 M in 0.2 N HCl solution) the reaction vessel was purged with argon and then placed under microwave for 1 min (Lee et al. *J. Comb. Chem.* 2008). Acidic aq. CNBr results in methionine-specific cleavage at the C-terminus of the linear ATZ-peptide, resulting in cleavage of the peptide from the bead. The resulting solution was concentrated under centrifugal vacuum for 2 hours at 45° C.

3. Sequencing of Linear ATZ-Peptides Cleaved from Single Beads by MALDI-MS and MS/MS.

To each tube was added α-cyano-4-hydroxycinnamic acid (CHCA) (0.5 μL, 5 mg/mL matrix solution in acetonitrile/water (70:30) containing 0.1% TFA (v/v)). The mixture was taken up to be spotted onto a 384-well MALDI plate, which was allowed to stand for 15 min to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each sample in LIFT™ mode. BIOTOOLS® was used to assign the sequence based on analysis of the MS/MS spectra.

Candidate peptides were re-synthesized on a cleavable resin. The linear peptide was first synthesized on Rink amide resin using conventional Fmoc-based solid phase peptide synthesis (SPPS). The peptide was cyclized between the N-terminal Pra and C-terminal Az4 using copper(I) iodide (1.5 equiv) and ascorbic acid (5 equiv) in 4:1 NMP:piperidine. On the next day, the residual copper bound to the resin was removed by shaking the resin with NMP containing 5% (w/v) sodium diethyldithiocarbamate trihydrate and 5% (v/v) N,N-diisopropylethylamine for 5 min. These monocyclic peptides were then cleaved from the resin for 2 h with 92.5% TFA, 2.5% $H_2O$, 2.5% TIS (triisopropylsilane), and 2.5% DODT (3,6-dioxa-1,8-octanedithiol), and then purified by reversed phase HPLC using a $C_{18}$ column (Phenomenex Luna, 5 μm, 250×10 mm).

Example 4: In Vitro Assays with IDO1 Epitope Targeted Ligands

1. IDO1 ELISA (Affinity Assay).

Protocol: A black 96-well NEUTRAVIDIN® Coated High Binding Capacity plate (15510, Pierce) was coated with 2 μM biotinylated macrocyclic peptide ligand in TBS (25 mM Tris-HCl, 150 mM NaCl, pH 7.6) for 2 h at room temperature. The plate was aspirated and then washed with Wash Buffer (0.05% (v/v) TWEEN® 20 in PBS, 6×). His-tagged IDO1 human recombinant protein (71182, BPS Biosciences) was serially diluted in Wash Buffer (from 200 to 0 nM) and incubated in the designated microwells for 1 h at room temperature. Microwells were aspirated and subsequently washed with Wash Buffer (11×). To detect the bound IDO1 protein, Alkaline Phosphatase (AP)-conjugated Anti-6×HIS TAG® antibody [HIS-1] (ab49746, Abcam) was prepared at 1:10,000 dilution and added to the microwells for 1 h at room temperature. The plate was aspirated and washed with Wash Buffer (5×). ATTOPHOS® AP Fluorescent Substrate System (S1000, Promega) was employed to develop the microwells. Using an excitation wavelength of 430 nm, fluorescent emission at 535 nm was recorded by Beckman Coulter DTX880 photometer. Titration curves were fit using a four-parameter regression curve fitting program to determine $EC_{50}$ values.

Results and Discussion: The binding affinities of biotin-$PEG_3$-modified macrocyclic peptide ligands were tested in an ELISA format. For these assays, a dilution series of His-tagged IDO1 human recombinant protein was captured using the macrocyclic peptide ligands immobilized on a NEUTRAVIDIN®-coated plate. The nine macrocyclic peptide ligands displayed $EC_{50}$ values ranging from 20 to 125 nM for human IDO1 protein. The sequences of the peptide ligands are listed in Table 1, where D-amino acids are denoted in lowercase, Me-Trp=1-methyl-L-tryptophan, and F-Phe=4-fluoro-L-phenylalanine. Chemical structures are shown below Table 1.

TABLE 1

Sequences of macrocyclic peptide hits identified against IDO1

| | Epitope Targeted | x2 | x3 | x4 | x5 | x6 | SEQ ID NO |
|---|---|---|---|---|---|---|---|
| hit1 | 1 | f | r | f | Me-Trp | s | 7 |
| hit2 | 1 | n | s | f | r | Me-Trp | 6 |
| hit3 | 2 | r | y | s | Me-Trp | r | 25 |
| hit4 | 2 | n | l | f | Me-Trp | F-Phe | 31 |
| hit5 | 2 | n | l | w | Me-Trp | r | 28 |
| hit6 | 2 | s | P | w | w | F-Phe | 33 |
| hit7 | 3 | r | f | f | y | l | 37 |
| hit8 | 3 | n | s | h | F-Phe | r | 38 |
| hit9 | 1 | w | Y | r | a | y | 3 |

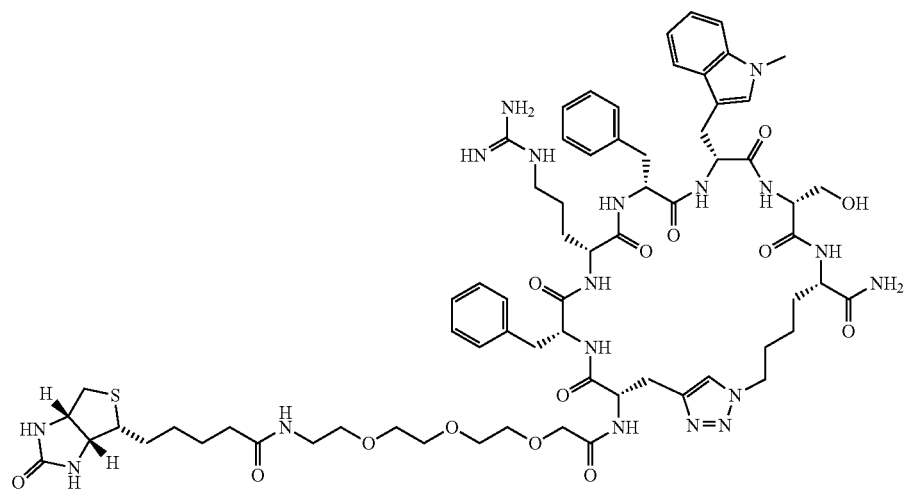 [SMILES: Cn1cc(C[C@H]2NC(=O)[C@@H](Cc3ccccc3)NC(=O)[C@@H](CCCNC(=N)N)NC(=O)[C@@H](Cc3ccccc3)NC(=O)[C@@H](NC(=O)COCCOCCOCCNC(=O)CCCC[C@H]3SC[C@H]4NC(=O)N[C@H]43)Cc3cn(nn3)CCCC[C@@H](C(N)=O)NC(=O)[C@@H](CO)NC2=O)c2ccccc21]

Macrocycle biotin-PEG$_3$-Cy(frf(Me-Trp)s) (SEQ ID NO:7). MALDI-MS (m/z): calcd. for C$_{68}$H$_{94}$N$_{18}$O$_{14}$S (M+H) 1419.65; found 1420.38. Sandwich ELISA for human IDO1 protein against biotin-PEG$_3$-modified Cy(frf (Me-Trp)s) (SEQ ID NO:7) yields EC$_{50}$ value of 20 nM.

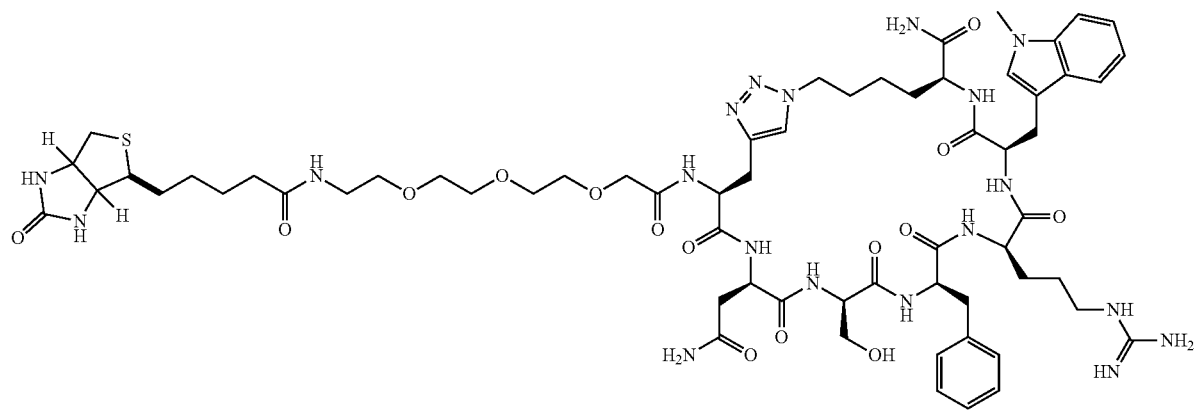 [SMILES: Cn1cc(C[C@H]2NC(=O)[C@@H](CCCNC(=N)N)NC(=O)[C@@H](Cc3ccccc3)NC(=O)[C@@H](CO)NC(=O)[C@@H](CC(N)=O)NC(=O)[C@@H](NC(=O)COCCOCCOCCNC(=O)CCCC[C@@H]3SCC4NC(=O)NC43)Cc3cn(nn3)CCCC[C@@H](C(N)=O)NC2=O)c2ccccc21]

Macrocycle biotin-PEG$_3$-Cy(nsfr(Me-Trp)) (SEQ ID NO:6). MALDI-MS (m/z): calcd. for C$_{63}$H$_{91}$N$_{19}$O$_{15}$S (M+H) 1386.58; found 1387.26. Sandwich ELISA for human IDO1 protein against biotin-PEG$_3$-modified Cy(nsfr (Me-Trp)) (SEQ ID NO:6) yields EC$_{50}$ value of 124 nM.

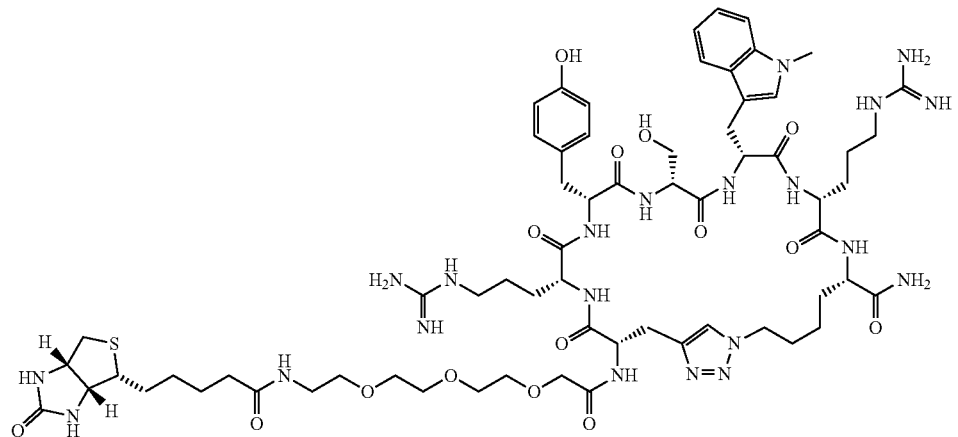 [SMILES: Cn1cc(C[C@H]2NC(=O)[C@@H](CO)NC(=O)[C@@H](Cc3ccc(O)cc3)NC(=O)[C@@H](CCCNC(=N)N)NC(=O)[C@@H](NC(=O)COCCOCCOCCNC(=O)CCCC[C@H]3SC[C@H]4NC(=O)N[C@H]43)Cc3cn(nn3)CCCC[C@@H](C(N)=O)NC(=O)[C@@H](CCCNC(=N)N)NC2=O)c2ccccc21]

Macrocycle biotin-PEG$_3$-Cy(rys(Me-Trp)r) (SEQ ID NO:25). MALDI-MS (m/z): calcd. for C$_{65}$H$_{97}$N$_{21}$O$_{15}$S (M+H) 1444.66; found 1445.11. Sandwich ELISA for human IDO1 protein against biotin-PEG$_3$-modified Cy(rys (Me-Trp)r) (SEQ ID NO:25) yields EC$_{50}$ value of 81 nM. A solution of 200 nM macrocycle was immobilized in this assay.

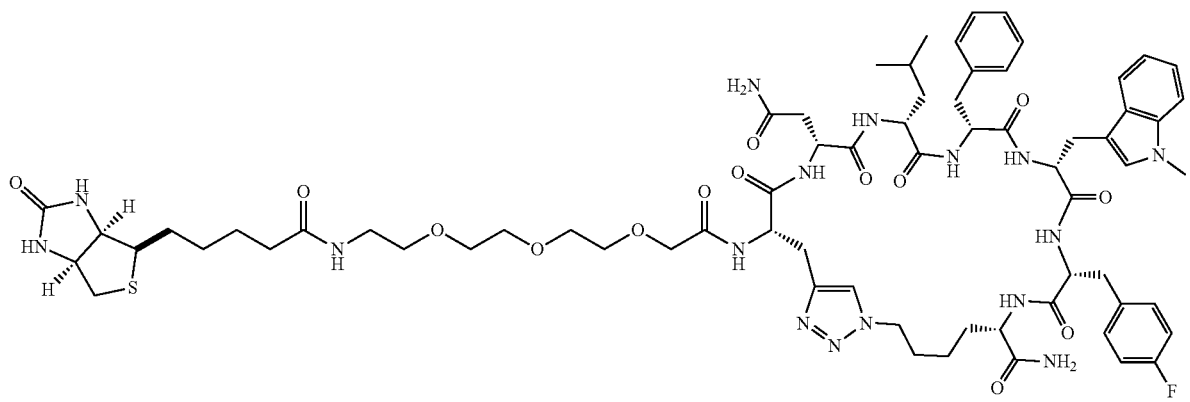 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(F)cc2)NC(=O)[C@@H](Cc2cn(C)c3ccccc23)NC(=O)[C@@H](Cc2ccccc2)NC1=O]

Macrocycle biotin-PEG$_3$-Cy(nlf(Me-Trp)(F-Phe)) (SEQ ID NO:31). MALDI-MS (m/z): calcd. for $C_{69}H_{93}FN_{16}O_{14}S$ (M+H) 1421.64; found 1421.47. Sandwich ELISA for human IDO1 protein against biotin-PEG$_3$-modified Cy(nlf(Me-Trp)(F-Phe)) (SEQ ID NO:31) yields EC$_{50}$ value of 20 nM.

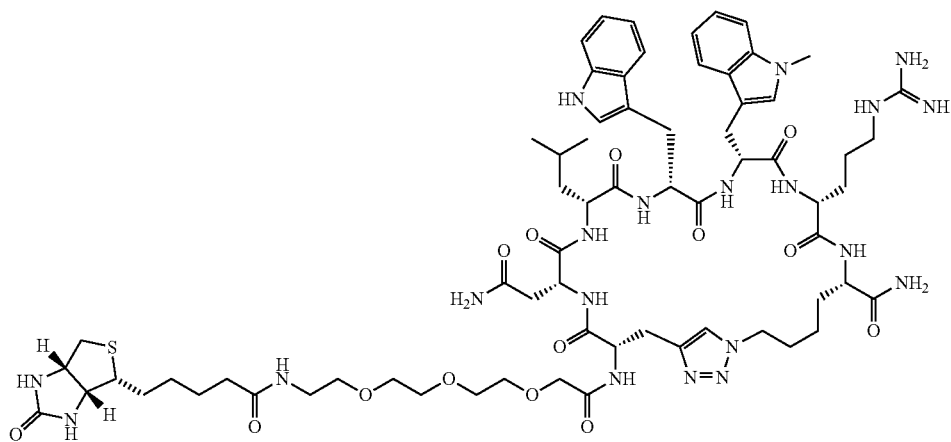 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](CCCNC(=N)N)NC(=O)[C@@H](Cc2cn(C)c3ccccc23)NC(=O)[C@@H](Cc2c[nH]c3ccccc23)NC1=O]

Macrocycle biotin-PEG$_3$-Cy(nlw(Me-Trp)r) (SEQ ID NO:28). MALDI-MS (m/z): calcd. for $C_{68}H_{98}N_{20}O_{14}S$ (M+H) 1451.70; found 1452.17. Sandwich ELISA for human IDO1 protein against biotin-PEG$_3$-modified Cy(nlw(Me-Trp)r) (SEQ ID NO:28) yields EC$_{50}$ value of 43 nM.

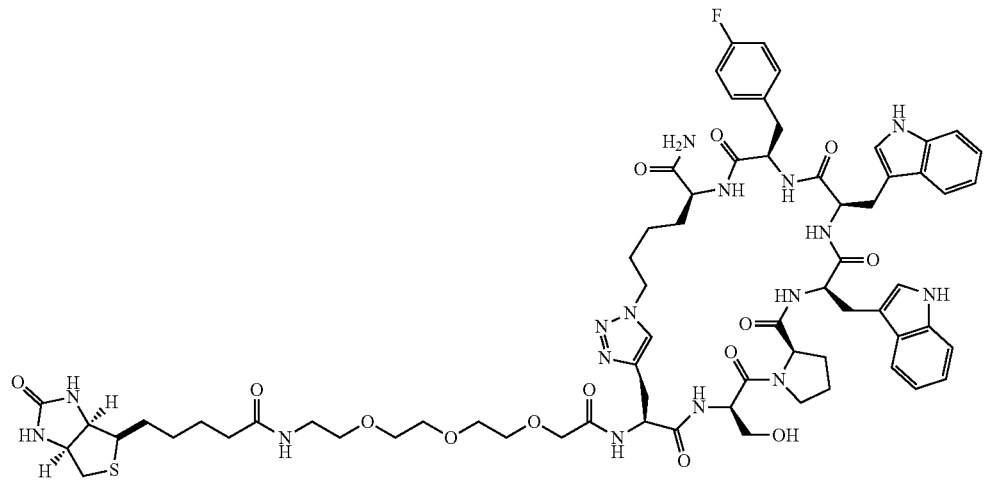 [SMILES: NC(=O)[C@@H]1CCCCn2cc(nn2)C[C@H](NC(=O)COCCOCCOCCNC(=O)CCCC[C@H]2SC[C@H]3NC(=O)N[C@H]32)C(=O)N[C@H](CO)C(=O)N2CCC[C@@H]2C(=O)N[C@H](Cc2c[nH]c3ccccc23)C(=O)N[C@H](Cc2c[nH]c3ccccc23)C(=O)N[C@H](Cc2ccc(F)cc2)C(=O)N1]

Macrocycle biotin-PEG$_3$-Cy(spww(F-Phe)) (SEQ ID NO:33). MALDI-MS (m/z): calcd. for C$_{68}$H$_{87}$FN$_{16}$O$_{14}$S (M+H) 1403.58; found 1403.60. Sandwich ELISA for human IDO1 protein against biotin-PEG$_3$-modified Cy(spww(F-Phe)) (SEQ ID NO:33) yields EC$_{50}$ value of 65 nM.

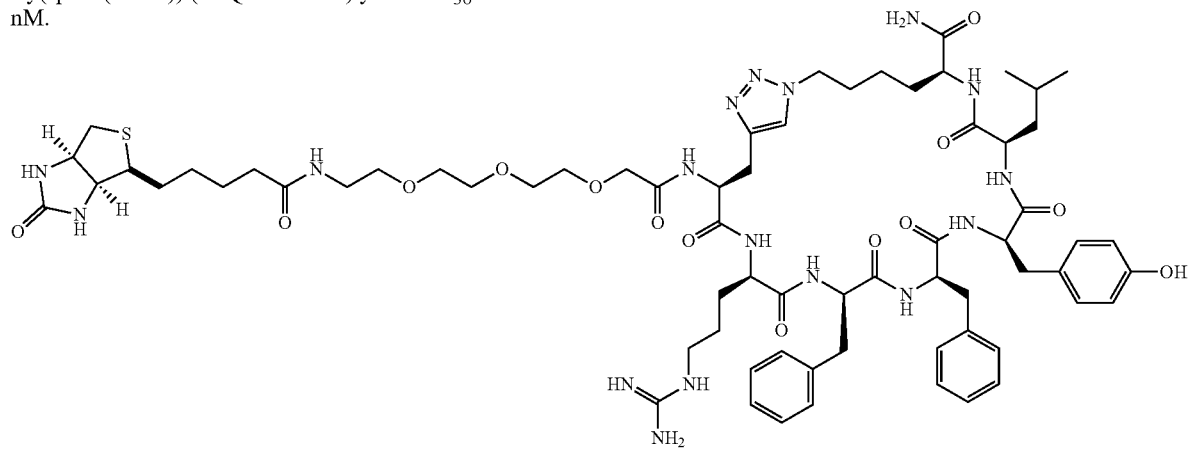

Macrocycle biotin-PEG$_3$-Cy(rffyl) (SEQ ID NO:37). MALDI-MS (m/z): calcd. for C$_{68}$H$_{97}$N$_{17}$O$_{14}$S (M+H) 1408.67; found 1408.92. Sandwich ELISA for human IDO1 protein against biotin-PEG$_3$-modified Cy(rffyl) (SEQ ID NO:37) yields EC$_{50}$ value of 125 nM.

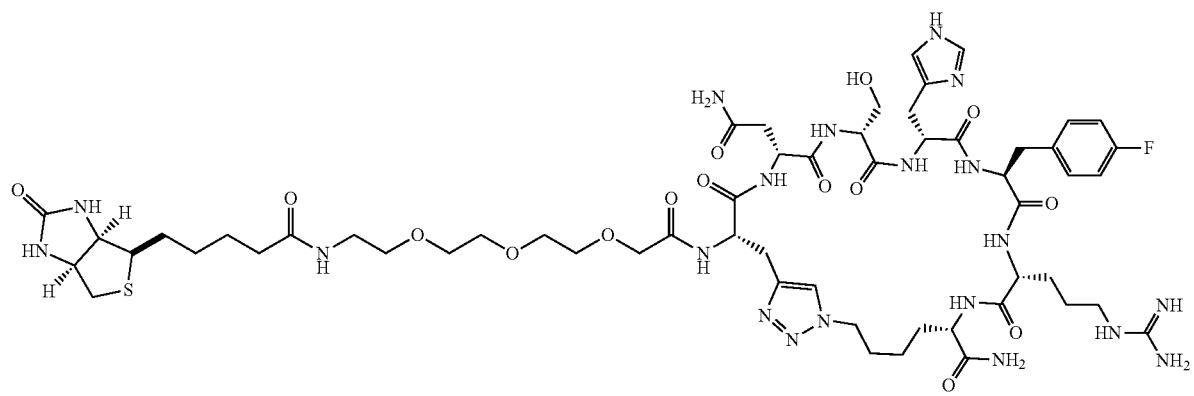 [SMILES: N=C(N)NCCC[C@H]1NC(=O)[C@H](Cc2ccc(F)cc2)NC(=O)[C@@H](Cc2c[nH]cn2)NC(=O)[C@@H](CO)NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC1=O]

Macrocycle biotin-PEG$_3$-Cy(nsh(F-Phe)r) (SEQ ID NO:38). MALDI-MS (m/z): calcd. for $C_{57}H_{86}FN_{20}O_{15}S$ (M+H) 1341.62; found 1341.63. Sandwich ELISA for human IDO1 protein against biotin-PEG$_3$-modified Cy(nsh (F-Phe)r) (SEQ ID NO:38) yields EC$_{50}$ value of 68 nM.

incubated at 37° C. for 4 h to produce a fluorescent product. Activity was measured by reading sample fluorescence at λ=510 nm following excitation of the reaction product at λ=400 nm. INCB024360 analogue was tested as a control IDO1 inhibitor.

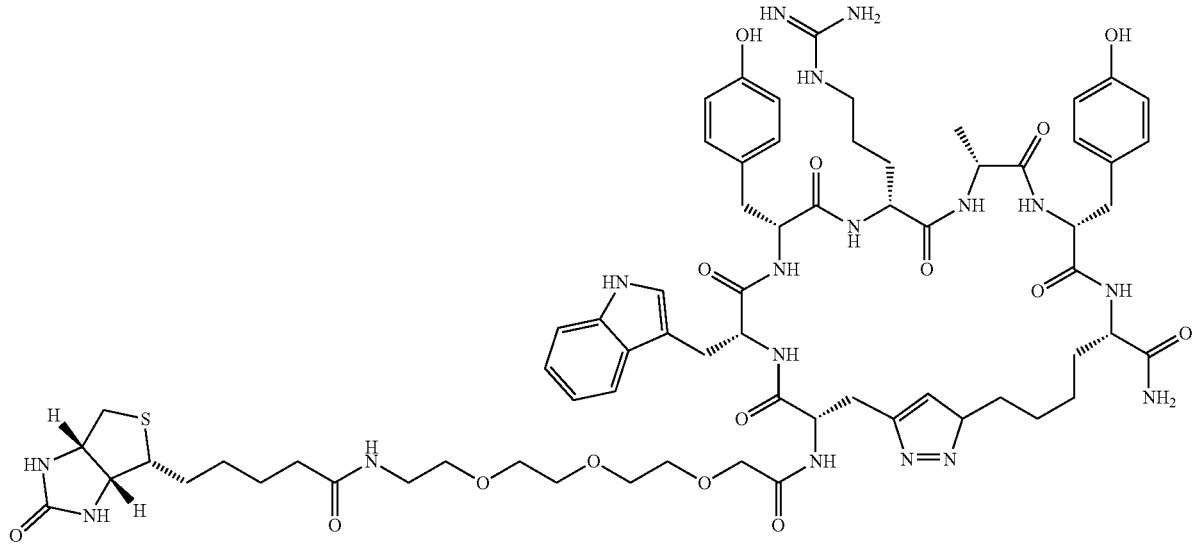 [SMILES: C[C@H]1NC(=O)[C@@H](CCCNC(=N)N)NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)CC2=CC(CCCC[C@@H](C(N)=O)NC(=O)[C@@H](Cc3ccc(O)cc3)NC1=O)N=N2]

Macrocycle biotin-PEG$_3$-Cy(wyray) (SEQ ID NO:3). MALDI-MS (m/z): calcd. for $C_{67}H_{92}N_{18}O_{15}S$ (M+H) 1420.67; found 1421.04. Sandwich ELISA for human IDO1 protein against biotin-PEG$_3$-modified Cy(wyray) (SEQ ID NO:3) yields EC$_{50}$ value of 25 nM.

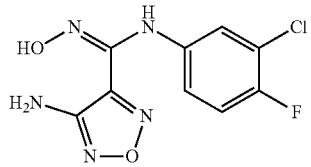

INCB024360 analogue

Example 5: Species Cross-Reactivity Analysis

To test for cross-reactivity with murine IDO1, the human IDO1 targeted macrocyclic peptide ligands were assayed against the murine IDO1 protein by ELISA. FIG. 2 shows curves from the ELISA titrations of human and murine IDO1 proteins against the immobilized macrocycles. As expected, the macrocyclic peptide ligands showed binding to both proteins because they were developed against IDO1 epitopes that show high homology between human and mouse. EC$_{50}$ values ranging from 18 to 158 nM for human IDO1 protein, and 17 to 130 nM for mouse IDO1 protein were obtained.

Example 6: Enzyme Assay for IDO1

Figure 3:
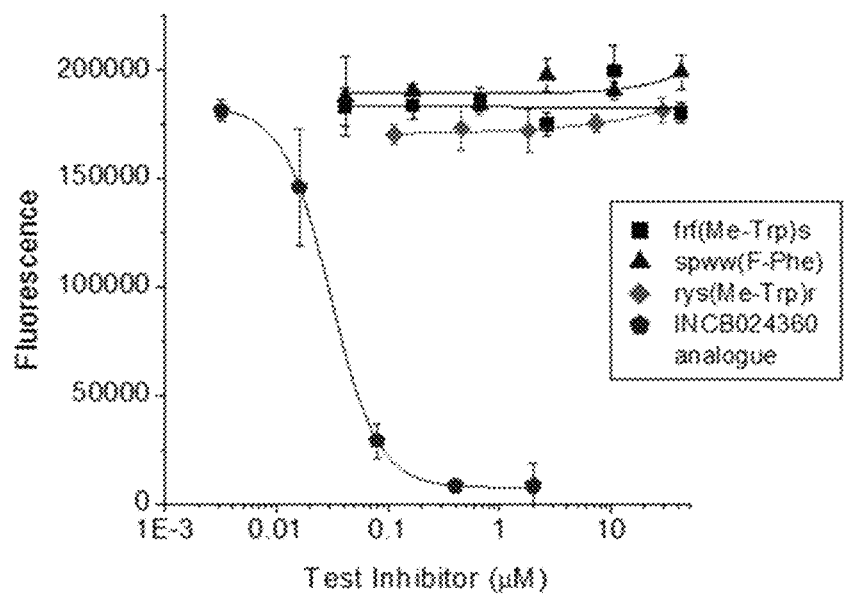
FIG. 3: IDO1 enzyme assay. Recombinant human IDO1 inhibition data for INCB024360 analogue compared to macrocycles frf(Me-Trp)s (SEQ ID NO:7), spww(F-Phe) (SEQ ID NO:33), and rys(Me-Trp)r (SEQ ID NO:25).

Since the macrocyclic peptide ligands are designed against epitopes near the active site, we sought to determine whether they can modulate the activity of IDO1. The IDO1 Fluorogenic Inhibitor Screening Assay Kit (72037, BPS Biosciences) was used to measure the enzyme inhibition of human IDO1 in the presence of macrocyclic peptide ligands. IDO1 catalyzes the conversion of the essential amino acid L-tryptophan (L-Trp) to N-formylkynurenine (NFK). In the assay, the test inhibitor and enzyme were added to a sample containing L-Trp substrate. After incubation for 1 h at room temperature, 20 µL Fluorescence Solution was added and INCB024360 analogue displayed an IC$_{50}$ value of 31 nM, in agreement with the published value (Röhrig et al. J. Med. Chem. 2015). Inhibitory potency of the macrocyclic peptide ligands was not observed (IC$_{50}$>40 µM) (FIG. 3).

Example 7: Assay to Determine Orientation of Macrocycle Binding to Synthetic IDO1 Epitopes Protocol: A black 96-well NEUTRAVIDIN® Coated High Binding Capacity plate (15510, Pierce) was coated with 2 µM macrocyclic peptide ligand in TBS (pH 7.6) for 1 h at room temperature. The plate was aspirated and then washed with Wash Buffer (0.05% (v/v) TWEEN® 20 in PBS, 6x). Chemically synthesized 6xHis-tagged IDO1 epitopes were prepared at 2 µM in Wash Buffer and incubated in the designated microwells for 1 h at room temperature. Wash Buffer without epitope was added as a control. Microwells were aspirated and subsequently washed with Wash Buffer (11x). To detect the bound IDO1 epitopes, AP-conjugated Anti-6xHIS TAG® antibody [HIS-1] (ab49746, Abcam) was prepared at 1:10,000 dilution and added to the microwells for 1 h at room temperature. The plate was aspirated and washed with Wash Buffer (5x). ATTOPHOS® AP Fluorescent Substrate System (S1000, Promega) was employed to develop the microwells. Using an excitation wavelength of 430 nm, fluorescent emission at 535 nm was recorded by Beckman Coulter DTX880 photometer. Data are shown after subtraction of the no-epitope background.

Results and Discussion: For this experiment, variants of IDO1 Epitope1 were synthesized with a 6×His assay handle and strategic scrambling of the sequences either N-terminal or C-terminal to the location of the click handle (F259). Regions of scrambled sequence are shown in italics.

```
E1Ctrl
                                   (SEQ ID NO: 1)
6XHis-PEG-GFWEDPKEFAGGSAGQSSVFQ Epitope1N
                                   (SEQ ID NO: 74)
6XHis-PEG-GFWEDPKEFQAFGVGSSAQGS Epitope1C
                                   (SEQ ID NO: 75)
6XHis-PEG-EPDFKEWGFAGGSAGQSSVFQ
```

Variants of IDO1 Epitope2 were similarly synthesized with a 6×His assay handle and strategic sequence scrambling (either N-terminal or C-terminal to L131). Regions of scrambled sequence are shown in italics.

```
E2Ctrl
                                   (SEQ ID NO: 24)
6XHis-PEG-LPPILVYADCVLANWKKKDPNK Epitope2N
                                   (SEQ ID NO: 76)
6XHis-PEG-LPPILVYADCVLKAKNNPWKKD Epitope2C
                                   (SEQ ID NO: 77)
6XHis-PEG-LCPDPAIVLYLANWKKKDPNK
```

Figure 4A:
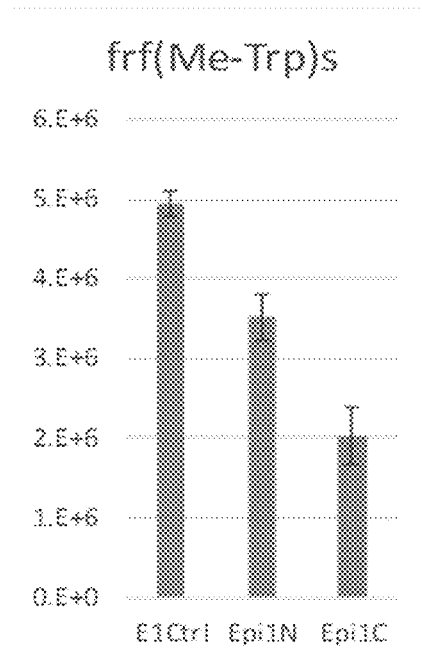
FIGS. 4A-4C: Orientation of macrocycle binding to IDO1 Epitopes 1 and 2.
Figure 4B:
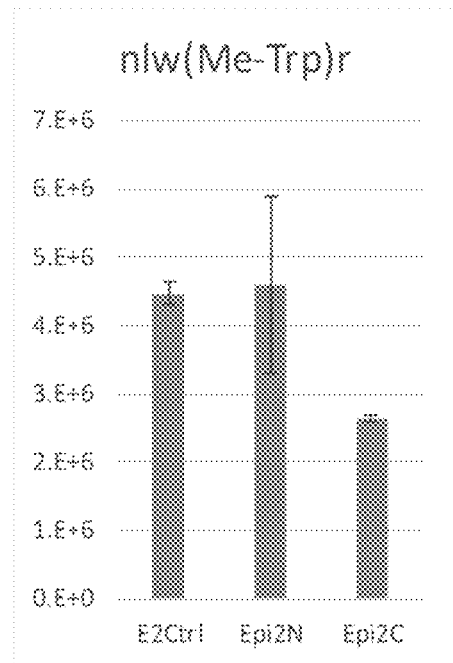
Figure 4C:
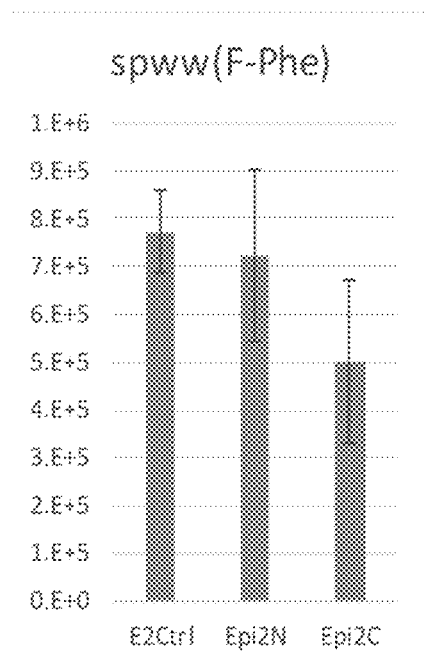

Point ELISAs for these 6×His-tagged IDO1 epitopes were conducted against the immobilized macrocyclic peptide ligands. For biotin-PEG$_3$-modified frf(Me-Trp)s (SEQ ID NO:7), maximum ELISA signals were obtained for binding to IDO1 Epitope1N (FIG. 4A) indicating preferential binding to the N-terminal portion of IDO1 Epitope1. For biotin-PEG$_3$-modified nlw(Me-Trp)r (SEQ ID NO:28) and spww (F-Phe) (SEQ ID NO:33), maximum ELISA signals were obtained for binding to IDO1 Epitope2N (FIGS. 14B and C) indicating preferential binding to the N-terminal portion of IDO1 Epitope2. These results confirm the selective nature of the epitope-targeting strategy.

Example 8: Alanine Scan and Tighter Rings (3- and 4-mers)

The effect of amino acid substitutions of the macrocycles on IDO1 binding was also studied. Each amino acid was systematically replaced with a D-alanine (Tables 2-5).

TABLE 2

Synthesis Data for spww(F-Phe) (SEQ ID NO: 33) Alanine Scan Variants

1

Biotin-PEG$_3$-Cy(apww(F-Phe)) (SEQ ID NO: 44). MALDI-MS (m/z): calcd. for C$_{68}$H$_{87}$FN$_{16}$O$_{13}$S (M + H) 1387.63; found 1388.07.

2

Biotin-PEG3-Cy(saww(F-Phe)) (SEQ ID NO: 34). MALDI-MS (m/z): calcd. for C$_{66}$H$_{85}$FN$_{16}$O$_{14}$S (M + H) 1377.61; found 1377.79.

TABLE 2-continued
Synthesis Data for spww(F-Phe) (SEQ ID NO: 33) Alanine Scan Variants
3
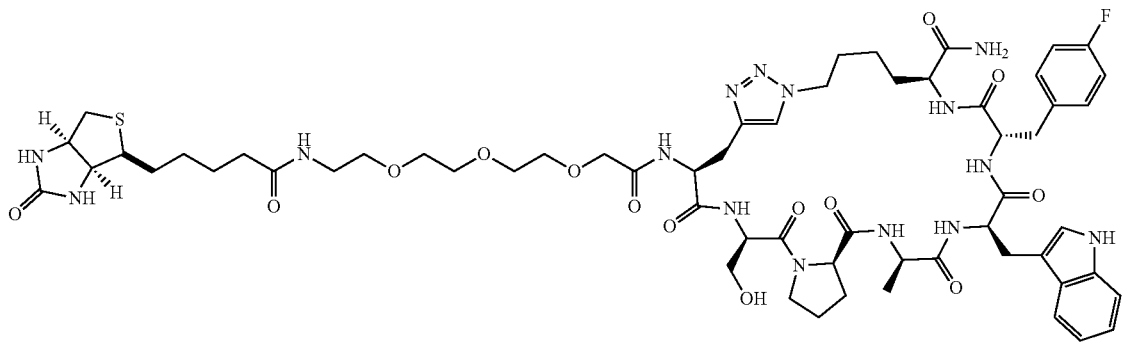 [SMILES: C[C@H]1NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC(=O)[C@@H](Cc2c[nH]c3ccccc23)NC1=O]
Biotin-PEG$_3$-Cy(spaw(F-Phe)) (SEQ ID NO: 45). MALDI-MS (m/z): calcd. for C$_{60}$H$_{82}$FN$_{15}$O$_{14}$S (M + H) 1288.59; found 1288.82.
4
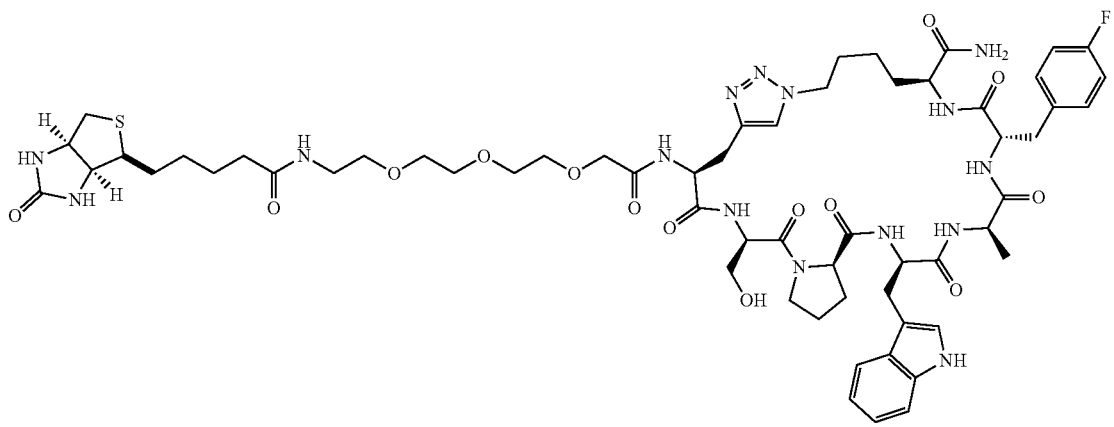 [SMILES: C[C@H]1NC(=O)[C@@H](Cc2c[nH]c3ccccc23)NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC1=O]
Biotin-PEG$_3$-Cy(spwa(F-Phe)) (SEQ ID NO: 46). MALDI-MS (m/z): calcd. for C$_{60}$H$_{82}$FN$_{15}$O$_{14}$S (M + H) 1288.59; found 1288.90.
5
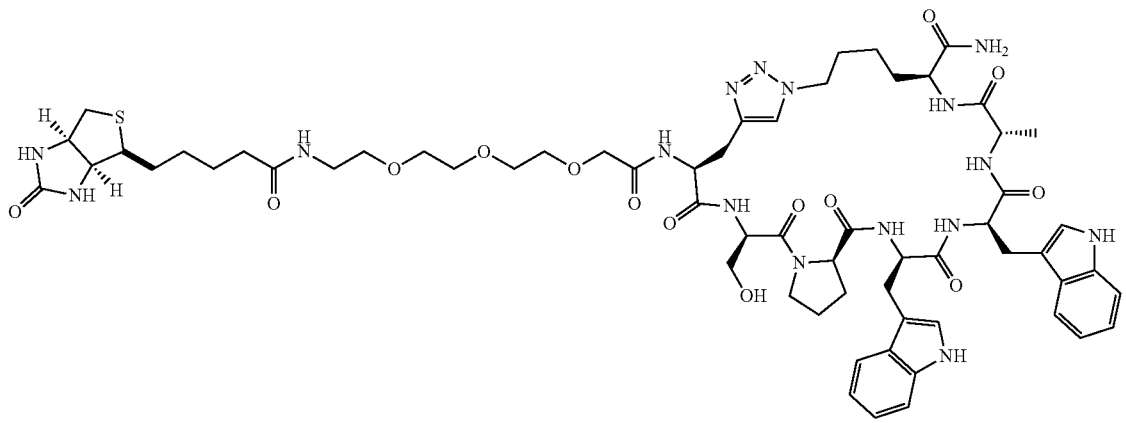 [SMILES: C[C@@H]1NC(=O)[C@@H](Cc2c[nH]c3ccccc23)NC(=O)[C@@H](Cc2c[nH]c3ccccc23)NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC1=O]
Biotin-PEG$_3$-Cy(spwwa) (SEQ ID NO: 47). MALDI-MS (m/z): calcd. for C$_{62}$H$_{84}$N$_{16}$O$_{14}$S (M + H) 1309.61; found 1309.92.

TABLE 3
Synthesis Data for nlf(Me-Trp)(F-Phe) (SEQ ID NO: 31) Alanine Scan Variants
1
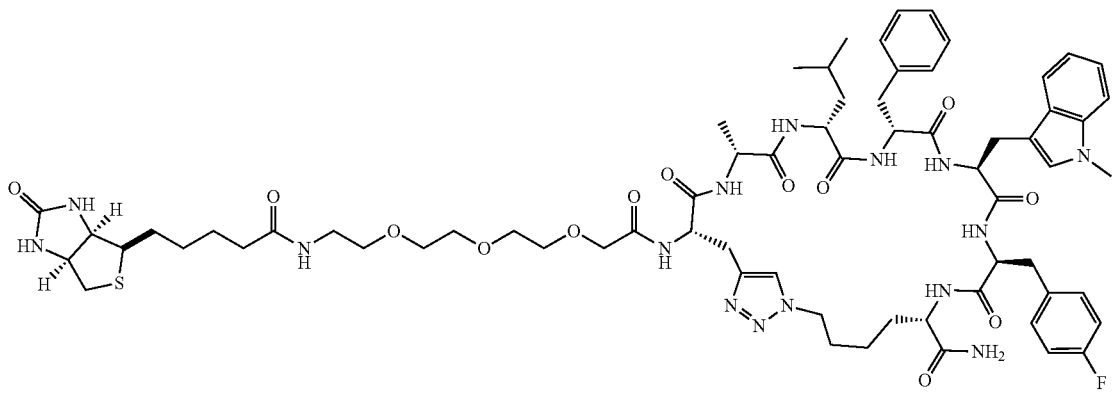
Biotin-PEG$_3$-Cy(alf(Me-Trp)(F-Phe)) (SEQ ID NO: 32). MALDI-MS (m/z): calcd. for $C_{68}H_{92}FN_{15}O_{13}S$ (M + H) 1378.67; found 1378.58.
2
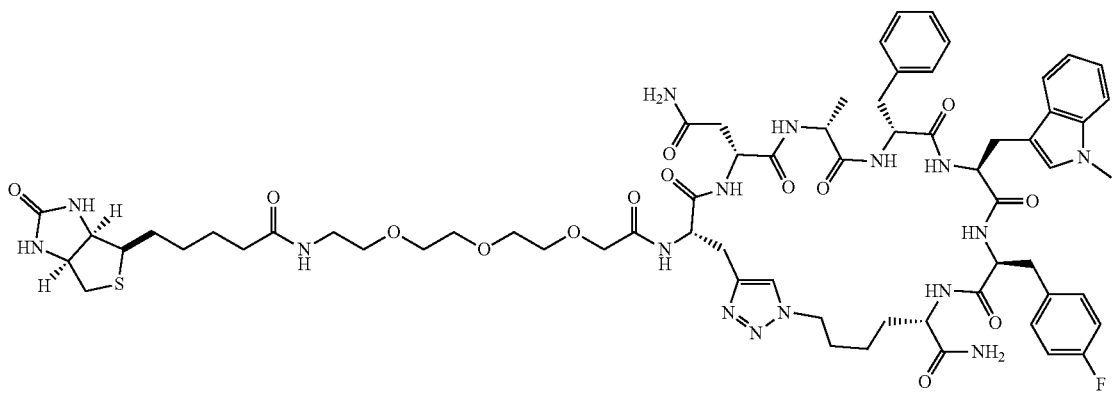
Biotin-PEG$_3$-Cy(naf(Me-Trp)(F-Phe)) (SEQ ID NO: 48). MALDI-MS (m/z): calcd. for $C_{66}H_{87}FN_{16}O_{14}S$ (M + H) 1379.63; found 1379.83.
3
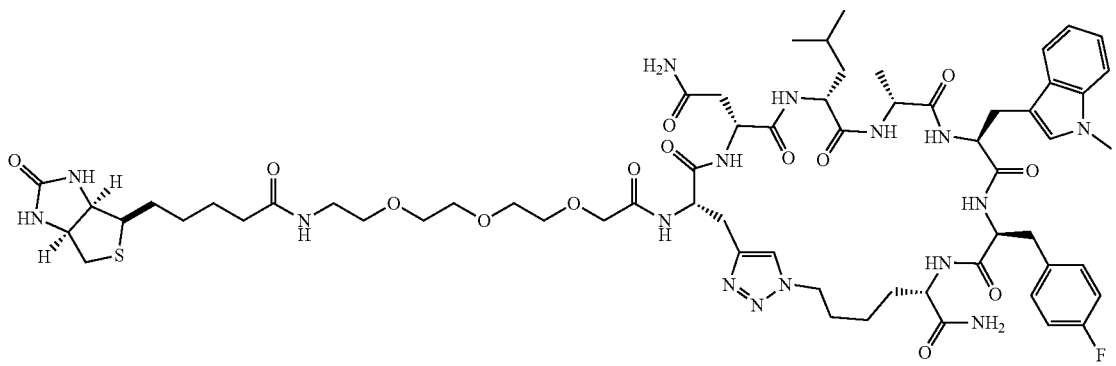
Biotin-PEG$_3$-Cy(nla(Me-Trp)(F-Phe)) (SEQ ID NO: 49). MALDI-MS (m/z): calcd. for $C_{63}H_{89}FN_{16}O_{14}S$ (M + H) 1345.64; found 1345.64.

TABLE 3-continued

Synthesis Data for nlf(Me-Trp)(F-Phe) (SEQ ID NO: 31) Alanine Scan Variants

4

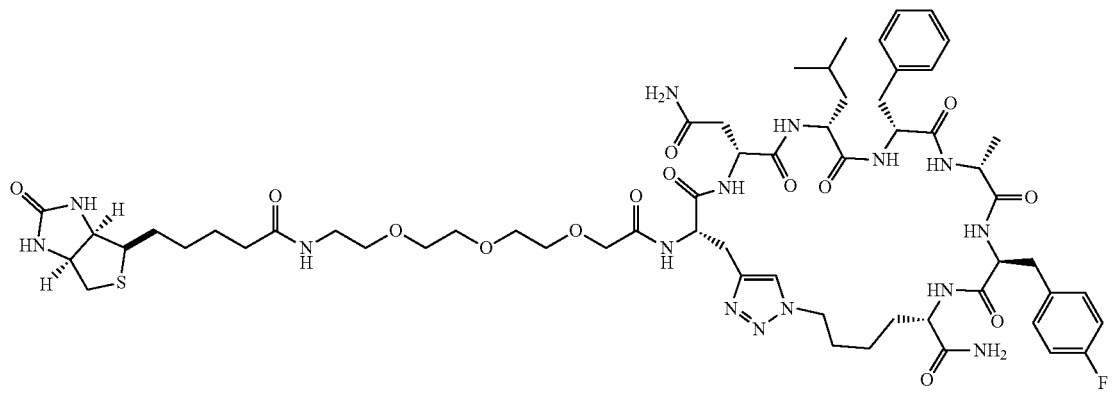

Biotin-PEG$_3$-Cy(nlfa(F-Phe)) (SEQ ID NO: 50). MALDI-MS (m/z): calcd. for C$_{60}$H$_{86}$FN$_{15}$O$_{14}$S (M + H) 1292.62; found 1292.55.

5

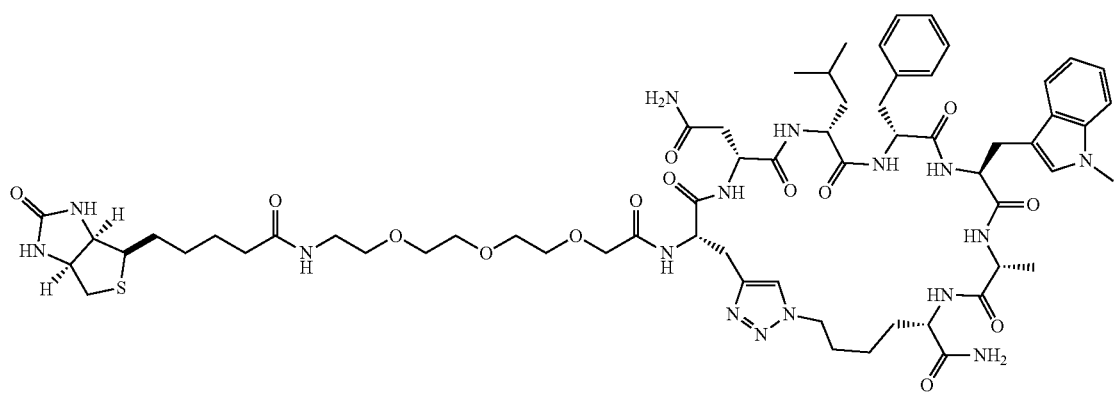

Biotin-PEG$_3$-Cy(nlf(Me-Trp)a) (SEQ ID NO: 51). MALDI-MS (m/z): calcd. for C$_{63}$H$_{90}$N$_{16}$O$_{14}$S (M + H) 1327.65; found 1327.63.

TABLE 4

Synthesis Data for frf(Me-Trp)s (SEQ ID NO: 7) Alanine Scan Variants

1

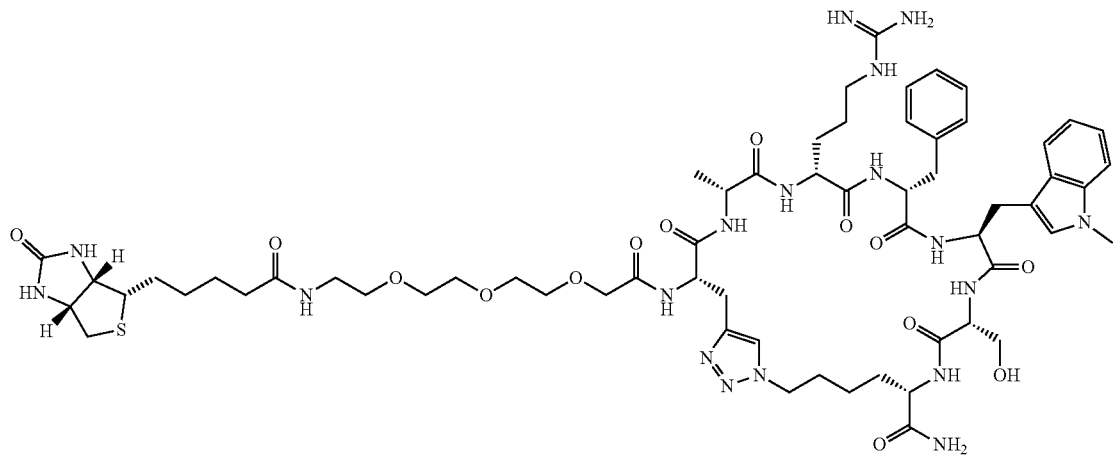

Biotin-PEG$_3$-Cy(arf(Me-Trp)s) (SEQ ID NO: 20). MALDI-MS (m/z): calcd. for C$_{62}$H$_{90}$N$_{18}$O$_{14}$S (M + H) 1343.66; found 1343.64.

TABLE 4-continued
Synthesis Data for frf(Me-Trp)s (SEQ ID NO: 7) Alanine Scan Variants
2
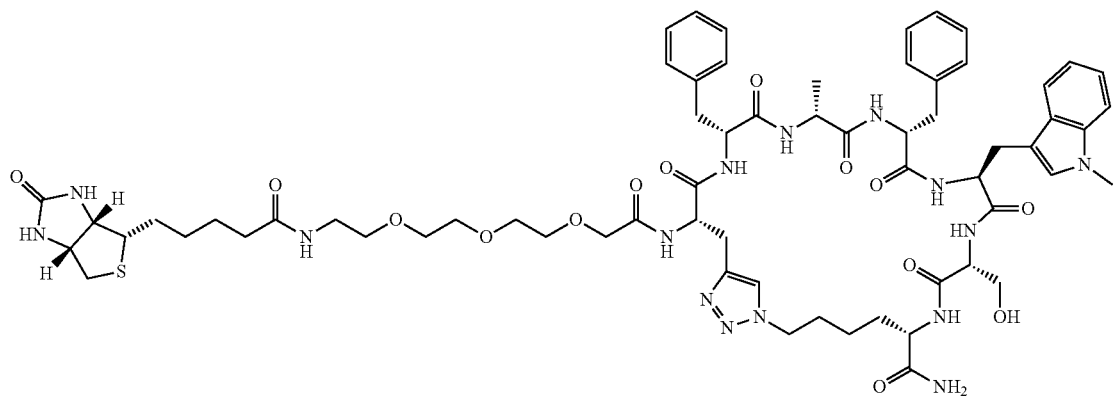
Biotin-PEG$_3$-Cy(faf(Me-Trp)s) (SEQ ID NO: 52). MALDI-MS (m/z): calcd. for C$_{65}$H$_{87}$N$_{15}$O$_{14}$S (M + H) 1334.63; found 1334.21.
3
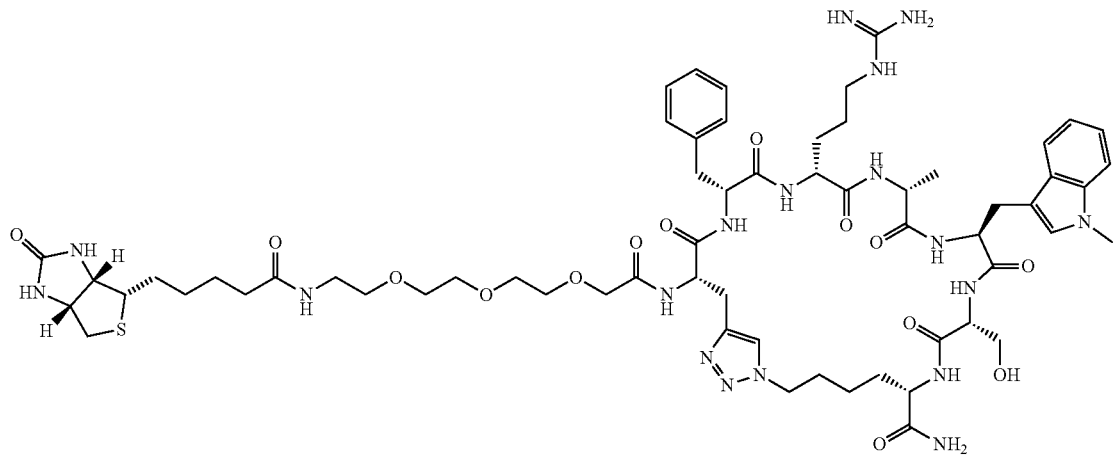
Biotin-PEG$_3$-Cy(fra(Me-Trp)s) (SEQ ID NO: 53) MALDI-MS (m/z): calcd. for C$_{62}$H$_{90}$N$_{18}$O$_{14}$S (M + H) 1343.66; found 1343.66.
4
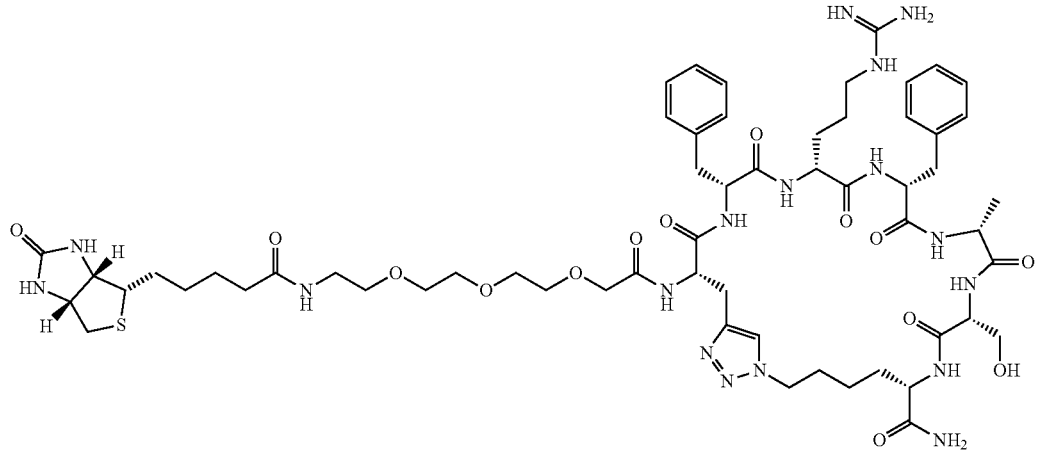
Biotin-PEG$_3$-Cy(frfas) (SEQ ID NO: 54). MALDI-MS (m/z): calcd. for C$_{59}$H$_{87}$N$_{17}$O$_{14}$S (M + H) 1290.63; found 1290.07.

TABLE 4-continued
Synthesis Data for frf(Me-Trp)s (SEQ ID NO: 7) Alanine Scan Variants
5
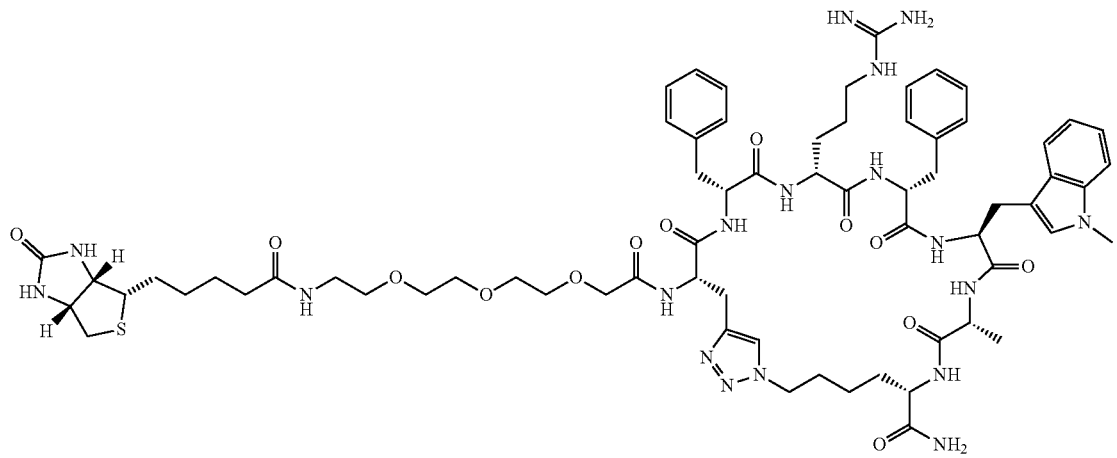
Biotin-PEG$_3$-Cy(frf(Me-Trp)a) (SEQ ID NO: 22). MALDI-MS (m/z): calcd. for C$_{68}$H$_{94}$N$_{18}$O$_{13}$S (M + H) 1403.70; found 1403.84.
TABLE 5
Synthesis Data for wyray (SEQ ID NO: 3) Alanine Scan Variants
1
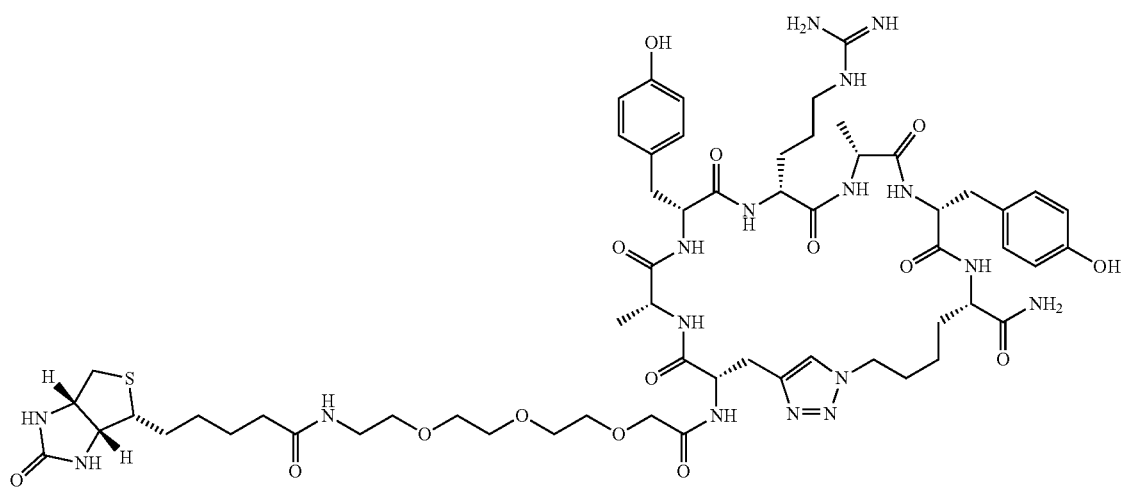 [SMILES: C[C@H]1NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC(=O)[C@@H](C)NC(=O)[C@@H](CCCNC(=N)N)NC(=O)[C@@H](Cc2ccc(O)cc2)NC1=O]
Biotin-PEG$_3$-Cy(ayray) (SEQ ID NO: 55). MALDI-MS (m/z): calcd. for C$_{59}$H$_{87}$N$_{17}$O$_{15}$S (M + H) 1306.63; found 1307.02.

TABLE 5-continued
Synthesis Data for wyray (SEQ ID NO: 3) Alanine Scan Variants
2
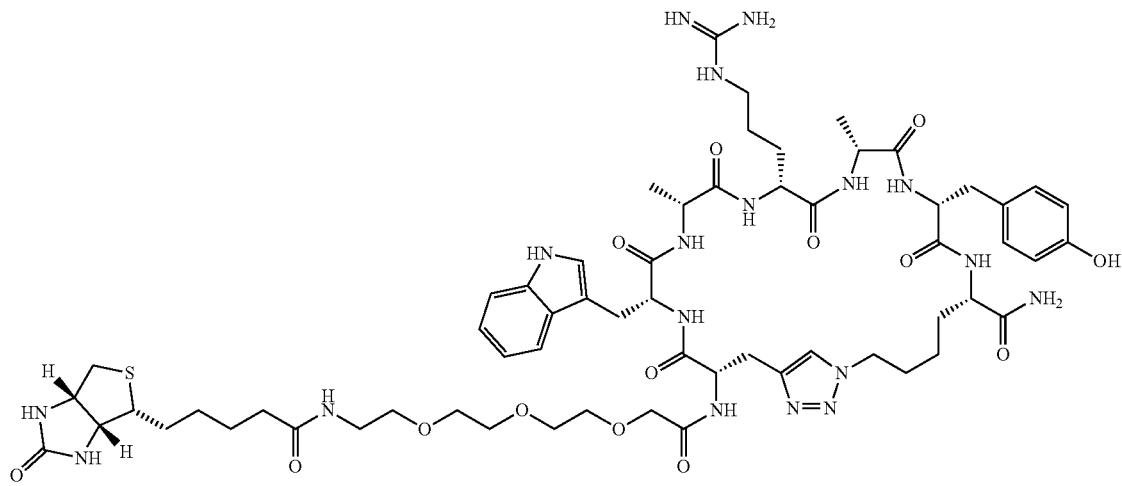 [SMILES: C[C@H]1NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC(=O)[C@@H](C)NC(=O)[C@@H](CCCNC(=N)N)NC1=O]
Biotin-PEG$_3$-Cy(waray) (SEQ ID NO: 56). MALDI-MS (m/z): calcd. for $C_{61}H_{88}N_{18}O_{14}S$ (M + H) 1329.64; found 1329.81.
3
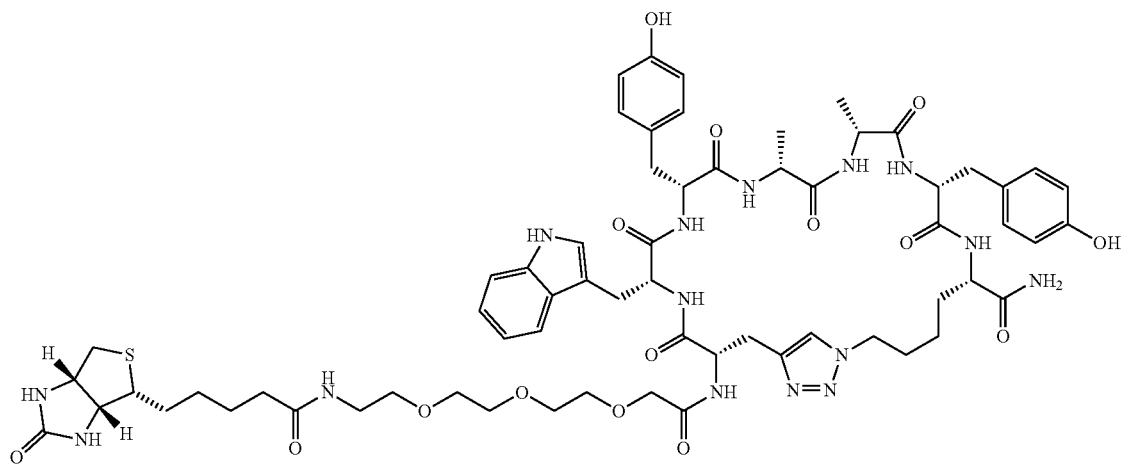 [SMILES: C[C@H]1NC(=O)[C@@H](C)NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(wyaay) (SEQ ID NO: 8). MALDI-MS (m/z): calcd. for $C_{64}H_{85}N_{15}O_{15}S$ (M + H) 1336.61; found 1336.76.
4
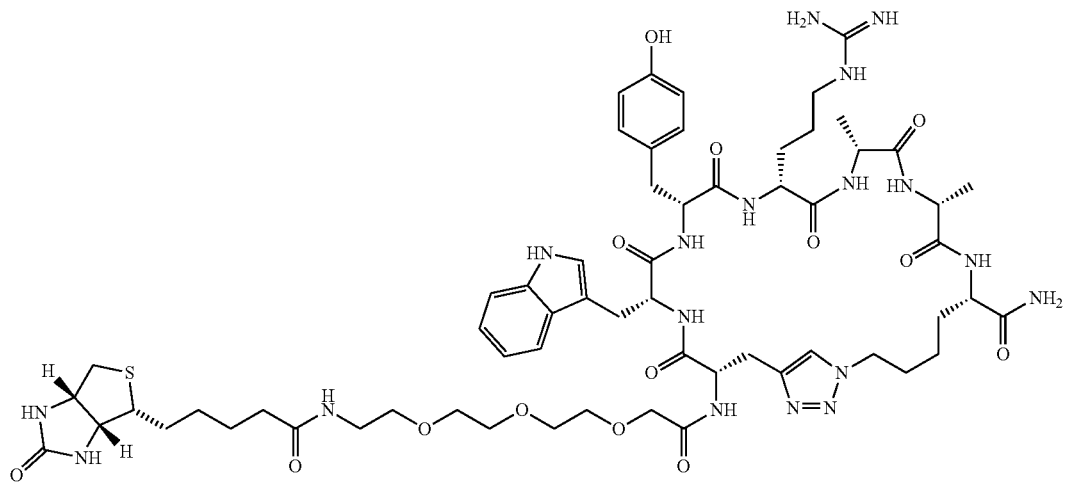 [SMILES: C[C@H]1NC(=O)[C@@H](C)NC(=O)[C@@H](CCCNC(=N)N)NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC1=O]
Biotin-PEG$_3$-Cy(wyraa) (SEQ ID NO: 57). MALDI-MS (m/z): calcd. for $C_{61}H_{88}N_{18}O_{14}S$ (M + H) 1329.64; found 1330.40.

The D-alanine substituted, biotin-PEG₃-modified macrocycles were tested in the IDO1 ELISA (Affinity assay). For these assays, a dilution series of His-tagged IDO1 human recombinant protein was captured using macrocycles immobilized on a NEUTRAVIDIN®-coated plate.

Based on the results of the alanine scan, 3-mer and 4-mer macrocycles were synthesized and assayed for IDO1 binding using the IDO1 ELISA (Affinity assay). Synthesis data for the 3-mer and 4-mer macrocycles is shown in Tables 6-9.

TABLE 6

Synthesis Data for spww(F-Phe) (SEQ ID NO: 33) 4-mer and 3-mer Variants

1

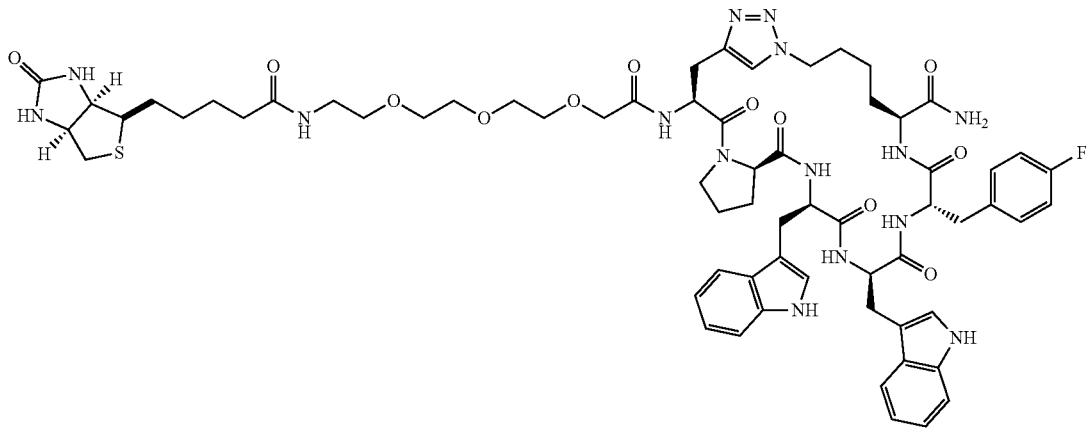

Biotin-PEG$_3$-Cy(pww(F-Phe)) (SEQ ID NO: 58). MALDI-MS (m/z): calcd. for C$_{65}$H$_{82}$FN$_{15}$O$_{12}$S (M + H) 1316.60; found 1316.72.

2

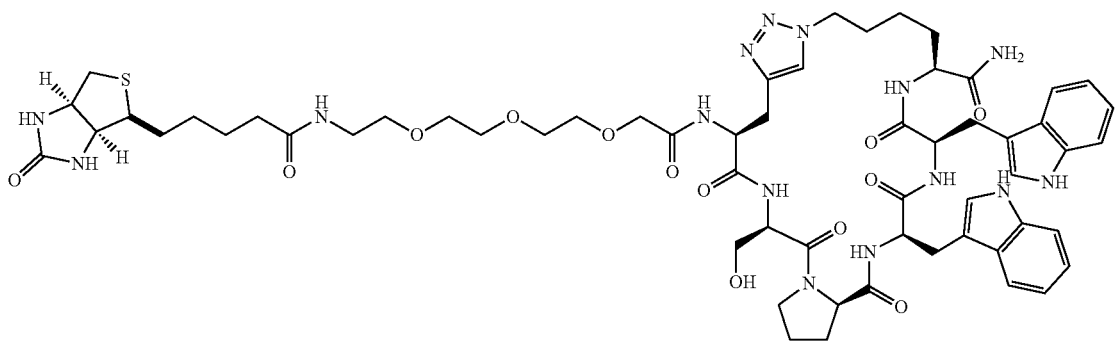 [SMILES: NC(=O)[C@@H]1CCCCn2cc(nn2)C[C@H](NC(=O)COCCOCCOCCNC(=O)CCCC[C@@H]2SC[C@@H]3NC(=O)N[C@@H]32)C(=O)N[C@H](CO)C(=O)N2CCC[C@@H]2C(=O)N[C@H](Cc2c[nH]c3ccccc23)C(=O)N[C@H](Cc2c[nH]c3ccccc23)C(=O)N1]

Biotin-PEG$_3$-Cy(spww) (SEQ ID NO: 59). MALDI-MS (m/z): calcd. for C$_{59}$H$_{79}$N$_{15}$O$_{13}$S (M + H) 1238.57; found 1238.59.

3

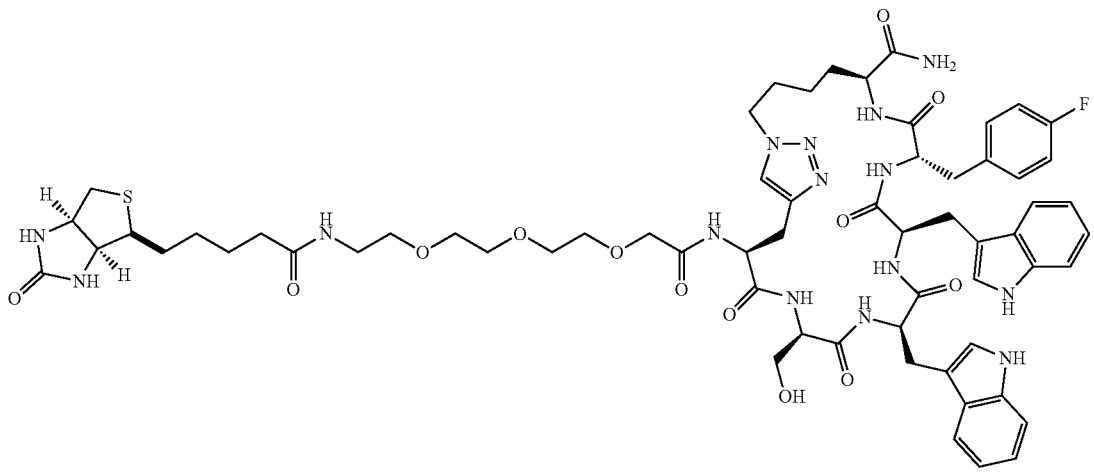 [SMILES: NC(=O)[C@@H]1CCCCn2cc(nn2)C[C@H](NC(=O)COCCOCCOCCNC(=O)CCCC[C@@H]2SC[C@@H]3NC(=O)N[C@@H]32)C(=O)N[C@H](CO)C(=O)N[C@H](Cc2c[nH]c3ccccc23)C(=O)N[C@H](Cc2c[nH]c3ccccc23)C(=O)N[C@@H](Cc2ccc(F)cc2)C(=O)N1]

Biotin-PEG$_3$-Cy(sww(F-Phe)) (SEQ ID NO: 35). MALDI-MS (m/z): calcd. for C$_{63}$H$_{80}$FN$_{15}$O$_{13}$S (M + H) 1306.58; found 1306.65.

TABLE 6-continued

Synthesis Data for spww(F-Phe) (SEQ ID NO: 33) 4-mer and 3-mer Variants

4

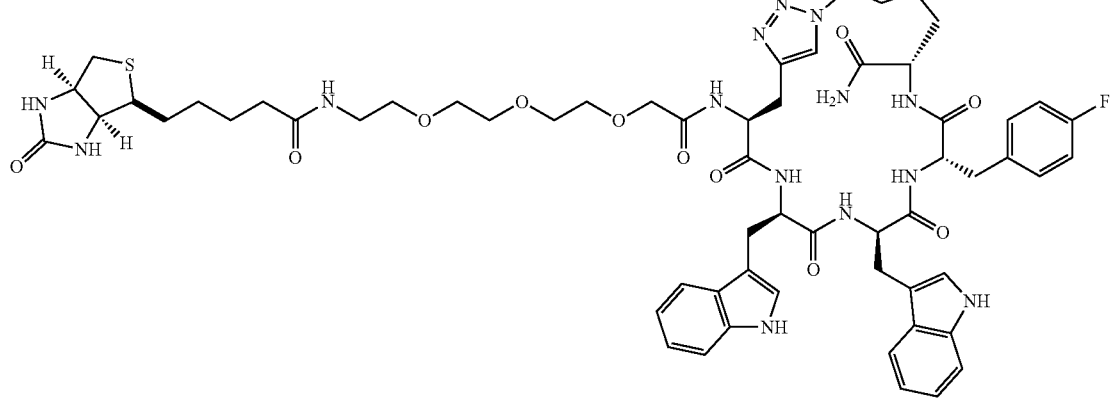

Biotin-PEG$_3$-Cy(ww(F-Phe)). MALDI-MS (m/z): calcd. for C$_{60}$H$_{75}$FN$_{14}$O$_{11}$S (M + H) 1219.54; found 1219.29.

TABLE 7

Synthesis Data for nlf(Me-Trp)(F-Phe) (SEQ ID NO: 31) 4-mer and 3-mer Variants

1

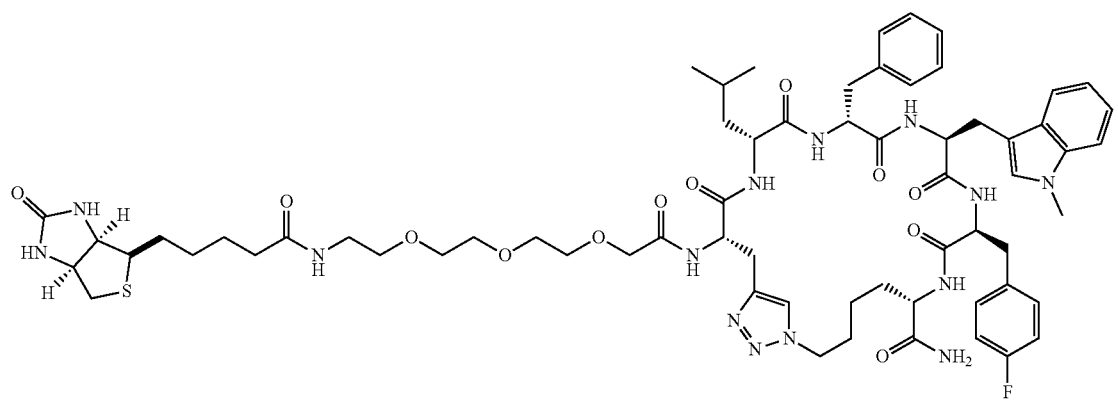

Biotin-PEG$_3$-Cy(lf(Me-Trp)(F-Phe)) (SEQ ID NO: 27). MALDI-MS (m/z): calcd. for C$_{65}$H$_{87}$FN$_{14}$O$_{12}$S (M + H) 1307.63; found 1307.54.

2

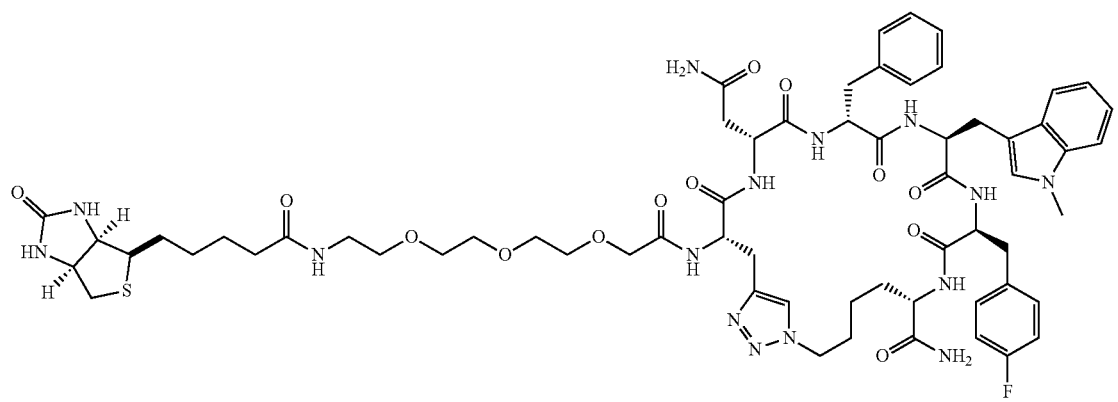

Biotin-PEG$_3$-Cy(nf(Me-Trp)(F-Phe)) (SEQ ID NO: 60). MALDI-MS (m/z): calcd. for C$_{63}$H$_{82}$FN$_{15}$O$_{13}$S (M + H) 1308.59; found 1308.31.

TABLE 7-continued
Synthesis Data for nlf(Me-Trp)(F-Phe) (SEQ ID NO: 31) 4-mer and 3-mer Variants
3
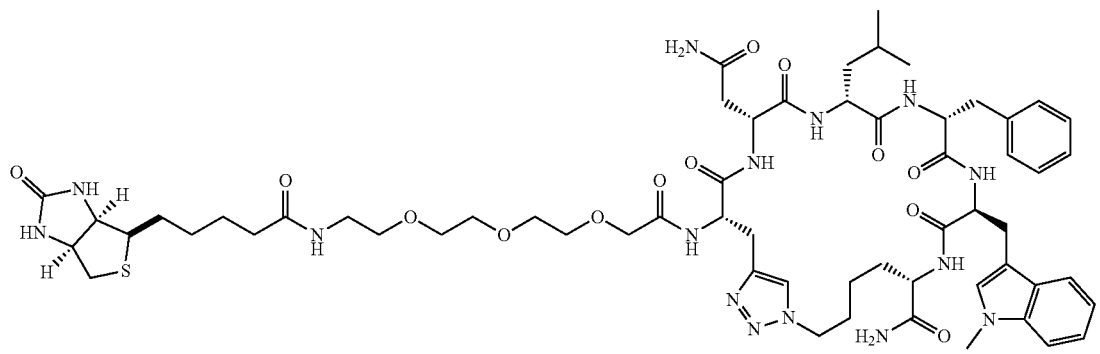
Biotin-PEG$_3$-Cy(nlf(Me-Trp)) (SEQ ID NO: 61). MALDI-MS (m/z): calcd. for $C_{60}H_{85}N_{15}O_{13}S$ (M + H) 1256.62; found 1256.51.
4
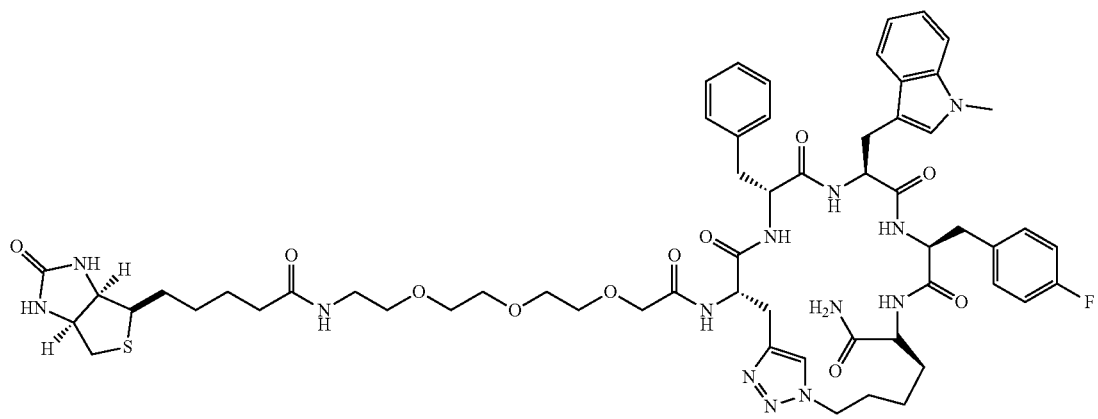
Biotin-PEG$_3$-Cy(f(Me-Trp)(F-Phe)). MALDI-MS (m/z): calcd. for $C_{59}H_{76}FN_{13}O_{11}S$ (M + H) 1194.55; found 1194.62.
TABLE 8
Synthesis Data for frf(Me-Trp)s (SEQ ID NO: 7) 4-mer Variants
1
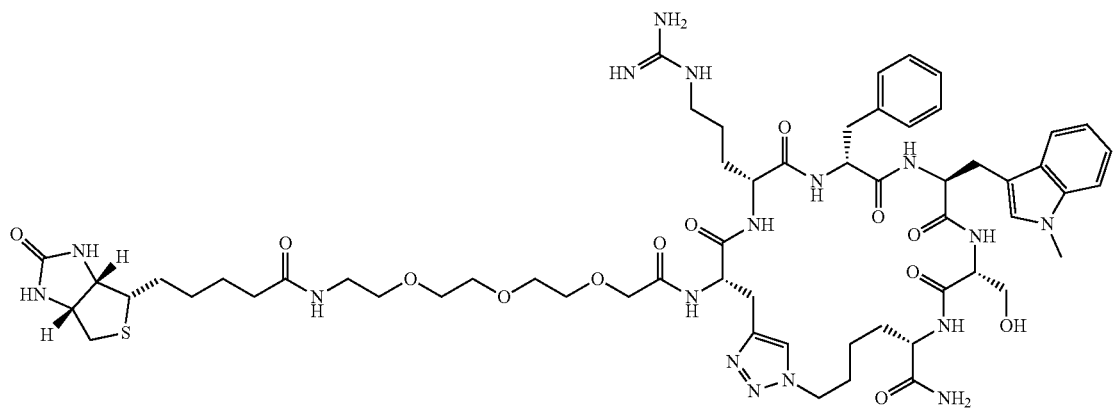
Biotin-PEG$_3$-Cy(rf(Me-Trp)s) (SEQ ID NO: 21). MALDI-MS (m/z): calcd. for $C_{59}H_{85}N_{17}O_{13}S$ (M + H) 1273.62; found 1273.41.

TABLE 8-continued
Synthesis Data for frf(Me-Trp)s (SEQ ID NO: 7) 4-mer Variants
2
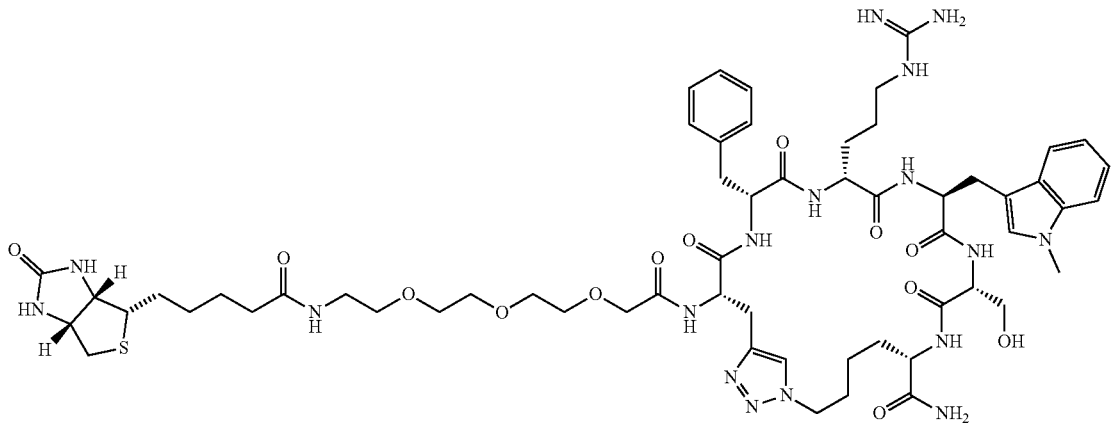
Biotin-PEG$_3$-Cy(fr(Me-Trp)s) (SEQ ID NO: 62). MALDI-MS (m/z): calcd. for $C_{59}H_{85}N_{17}O_{13}S$ (M + H) 1272.62; found 1273.07.
3
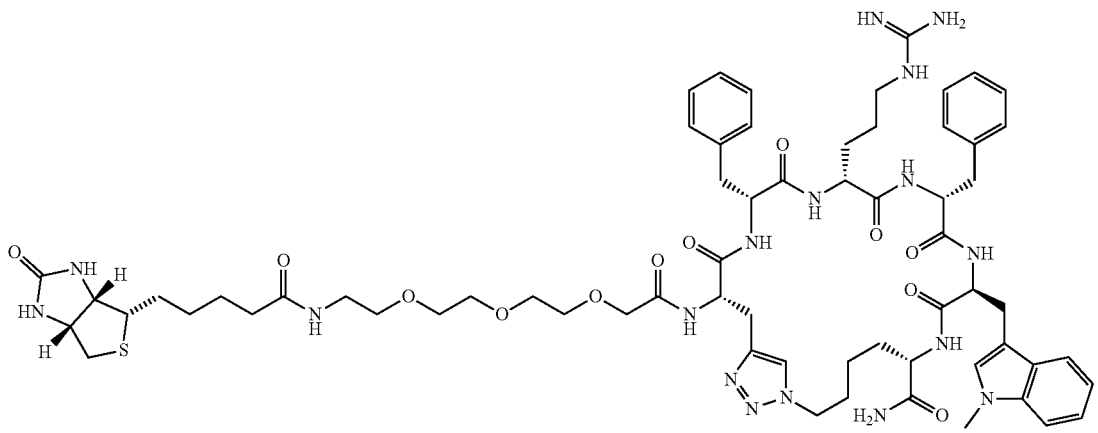
Biotin-PEG$_3$-Cy(frf(Me-Trp)) (SEQ ID NO: 23). MALDI-MS (m/z): calcd. for $C_{65}H_{89}N_{17}O_{12}S$ (M + H) 1332.66; found 1333.32.
TABLE 9
Synthesis Data for wyray (SEQ ID NO: 3) 4-mer Variants
1
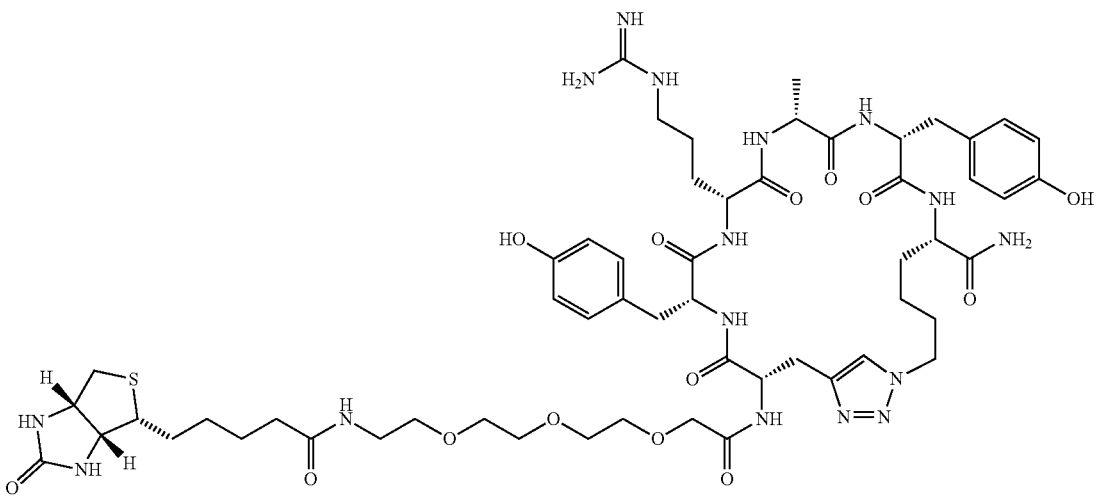 [SMILES: C[C@H]1NC(=O)[C@@H](CCCNC(=N)N)NC(=O)[C@@H](Cc2ccc(O)cc2)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(yray) (SEQ ID NO: 63). MALDI-MS (m/z): calcd. for $C_{56}H_{82}N_{16}O_{14}S$ (M + H) 1235.59; found 1235.68.

TABLE 9-continued

Synthesis Data for wyray (SEQ ID NO: 3) 4-mer Variants

2
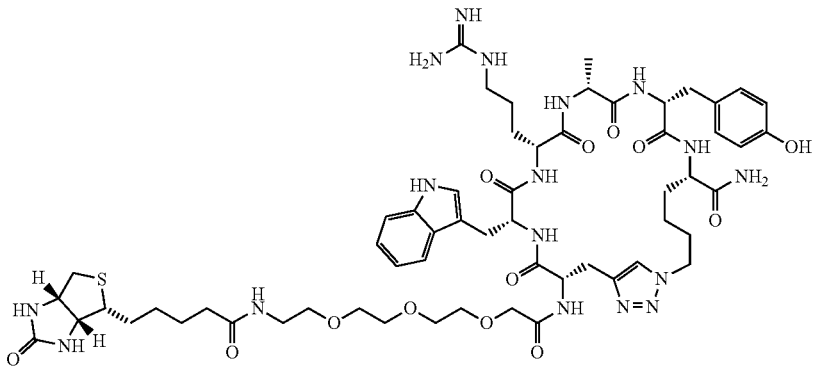 [SMILES: C[C@H]1NC(=O)[C@@H](CCCNC(=N)N)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]

Biotin-PEG$_3$-Cy(wray) (SEQ ID NO: 64). MALDI-MS (m/z): calcd. for C$_{58}$H$_{83}$N$_{17}$O$_{13}$S (M + H) 1258.61; found 1259.08.

3
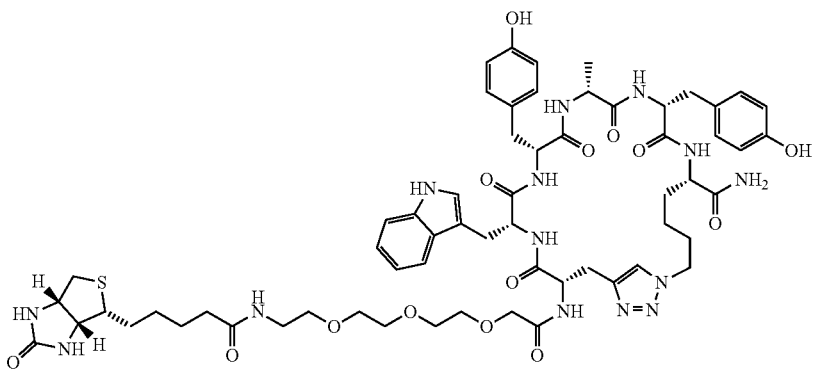 [SMILES: C[C@H]1NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]

Biotin-PEG$_3$-Cy(wyay) (SEQ ID NO: 65). MALDI-MS (m/z): calcd. for C$_{61}$H$_{80}$N$_{14}$O$_{14}$S (M + H) 1265.57; found 1265.69.

4
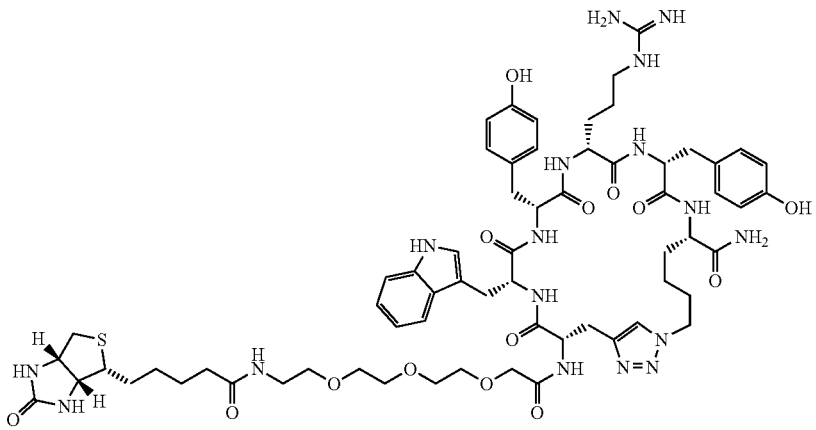 [SMILES: N=C(N)NCCC[C@H]1NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]

Biotin-PEG$_3$-Cy(wyry) (SEQ ID NO: 4). MALDI-MS (m/z): calcd. for C$_{64}$H$_{87}$N$_{17}$O$_{14}$S (M + H) 1350.63; found 1350.96.

Figure 5A:
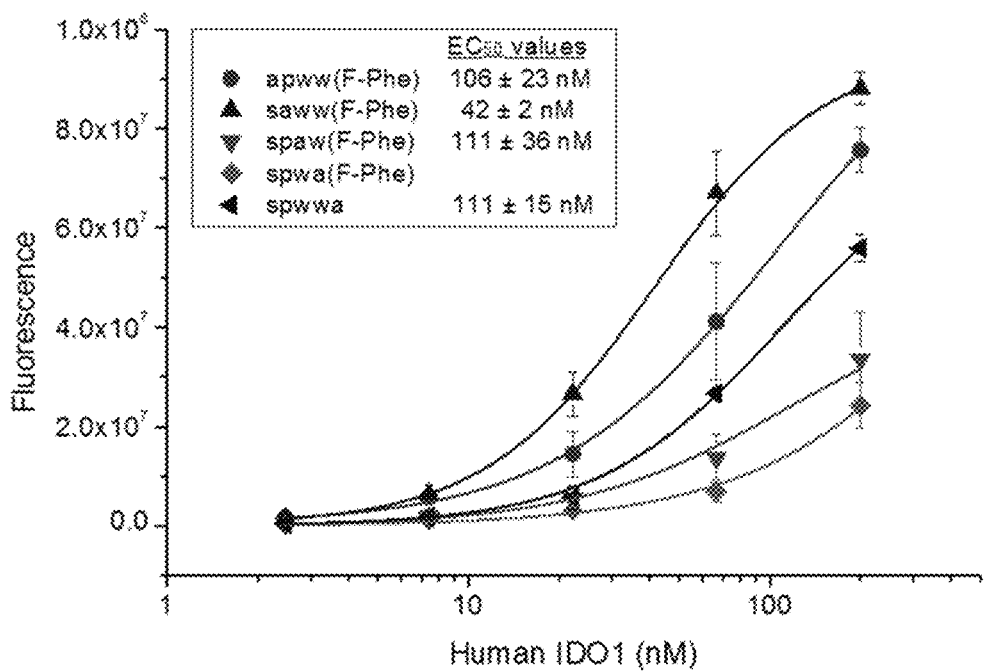
FIGS. 5A-5B: Optimization of biotin-PEG$_3$-Cy(spww(F-Phe)) (SEQ ID NO:33).
Figure 5B:
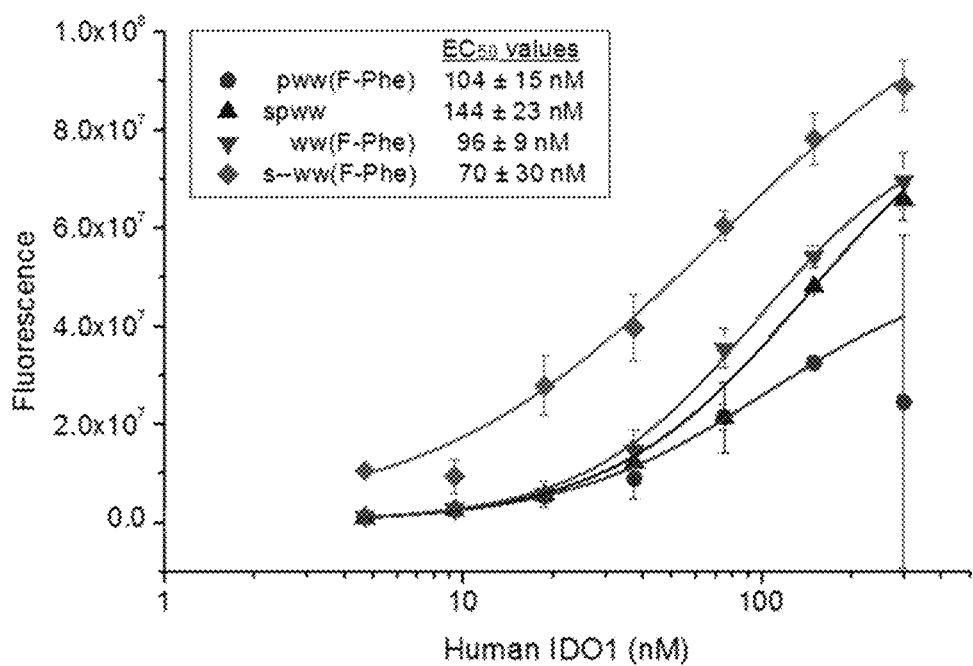

The five single alanine mutants of biotin-PEG$_3$-Cy(spww (F-Phe)) (SEQ ID NO:33) were assayed for binding to human IDO1 (FIG. 5A). Substitution of D-Trp (w) in this macrocycle weakens the binding to IDO1, signifying that D-Trp (w) is important. On the other hand, substitution of D-Pro (p) is tolerated. Macrocycle saww(F-Phe) (SEQ ID NO:34) shows a similar binding affinity to the original spww(F-Phe) (SEQ ID NO:33), with a similar maximum signal. The maximum signal of the 4-mer macrocycle sww (F-Phe) (SEQ ID NO:35), which lacks D-Pro (p), is superior to the other 4-mers generated (FIG. 5B).

Figure 6A:
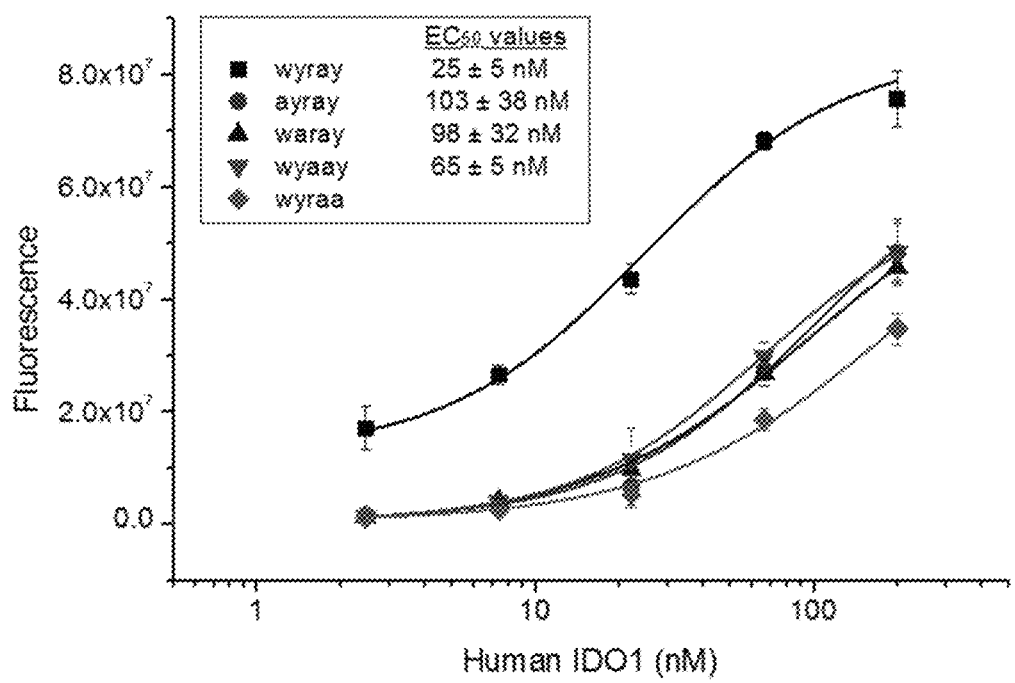
FIGS. 6A-6B: Optimization of biotin-PEG$_3$-Cy(wyray) (SEQ ID NO:3).
Figure 6B:
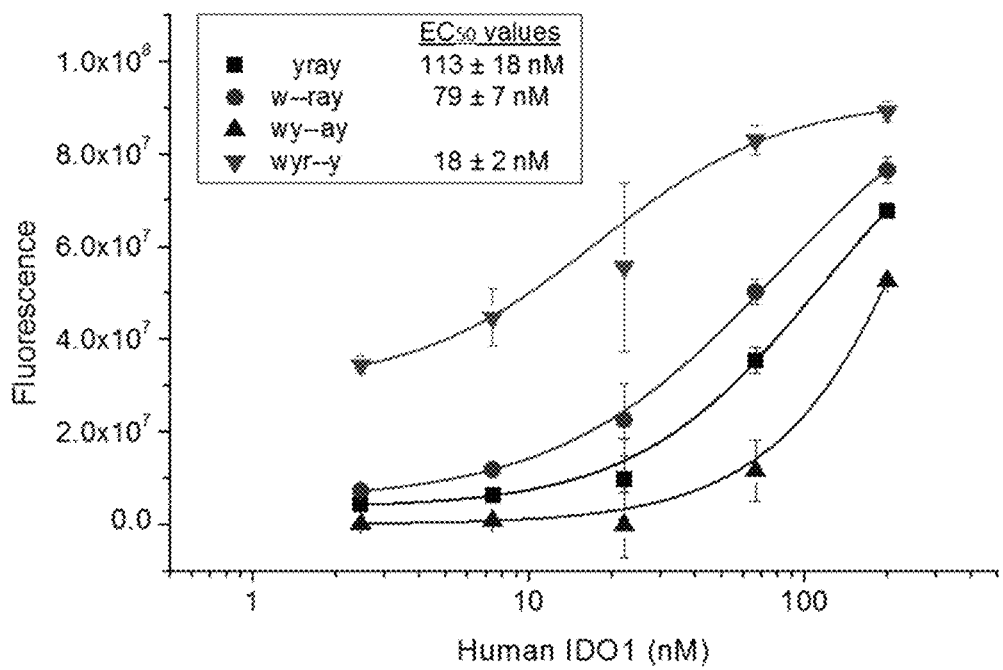

The four single alanine mutants of biotin-PEG$_3$-Cy (wyray) (SEQ ID NO:3) were assayed for binding to human IDO1 (FIG. 6A). Substituting any of the positions causes a small perturbation to IDO1 binding. The EC$_{50}$ values for these alanine mutants are similar, suggesting that all residues are equally important for IDO1 binding. Macrocycle wyry (SEQ ID NO:4) exhibited the best affinity among the 4-mer macrocycles suggesting that the D-Ala (a) is not required for IDO1 binding (FIG. 6B).

Figure 7A:
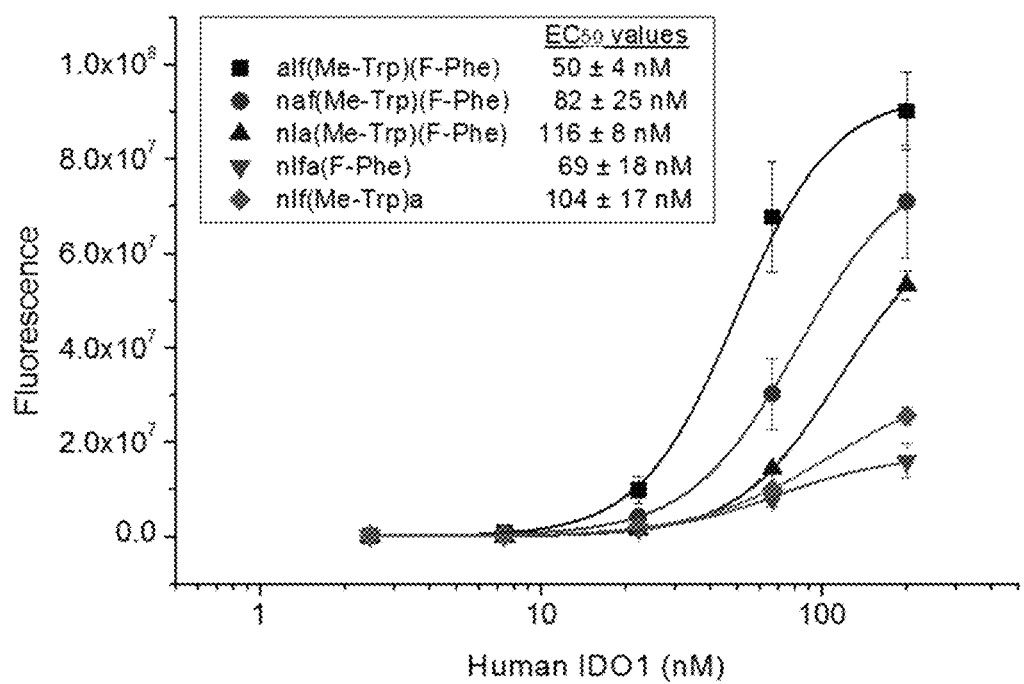
FIGS. 7A-7B: Optimization of biotin-PEG$_3$-Cy(nlf(Me-Trp)(F-Phe)) (SEQ ID NO:31).
Figure 7B:
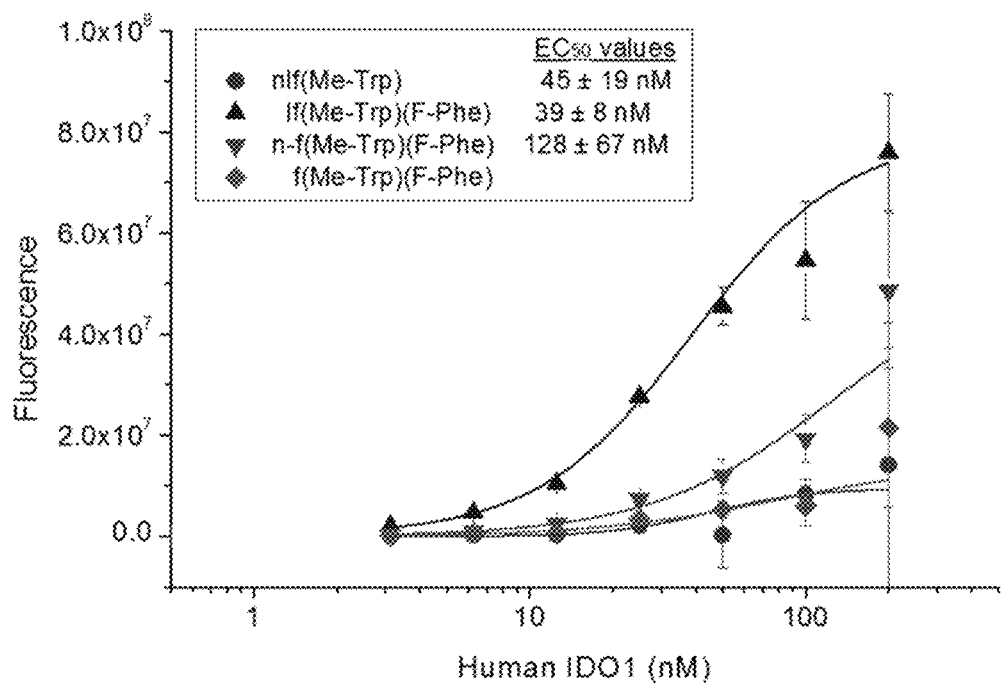

The five single alanine mutants of biotin-PEG$_3$-Cy(nlf (Me-Trp)(F-Phe)) (SEQ ID NO:31) were assayed for binding to human IDO1 (FIG. 7A). Making substitutions to the C-terminus of this macrocycle weakens the binding to IDO1, signifying that the C-terminus is important. The 4-mer macrocycle lf(Me-Trp)(F-Phe) (SEQ ID NO:27) only demonstrated a slight decrease in binding affinity when compared to the original 5-mer (FIG. 7B).

Figure 8A:
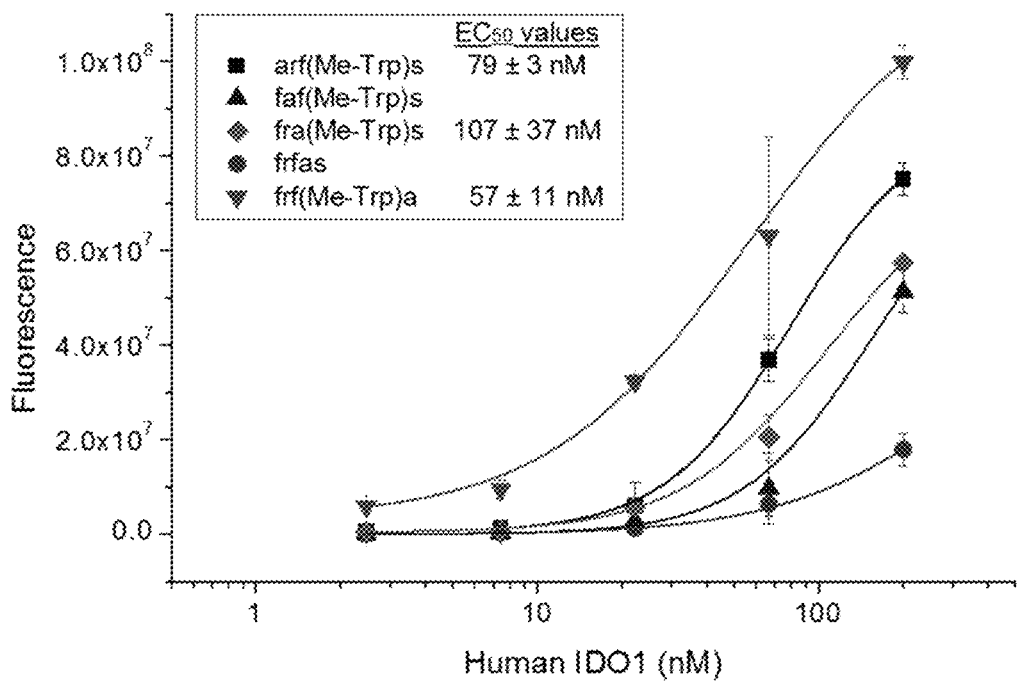
FIGS. 8A-8B: Optimization of biotin-PEG$_3$-Cy(frf(Me-Trp)s) (SEQ ID NO:7).
Figure 8B:
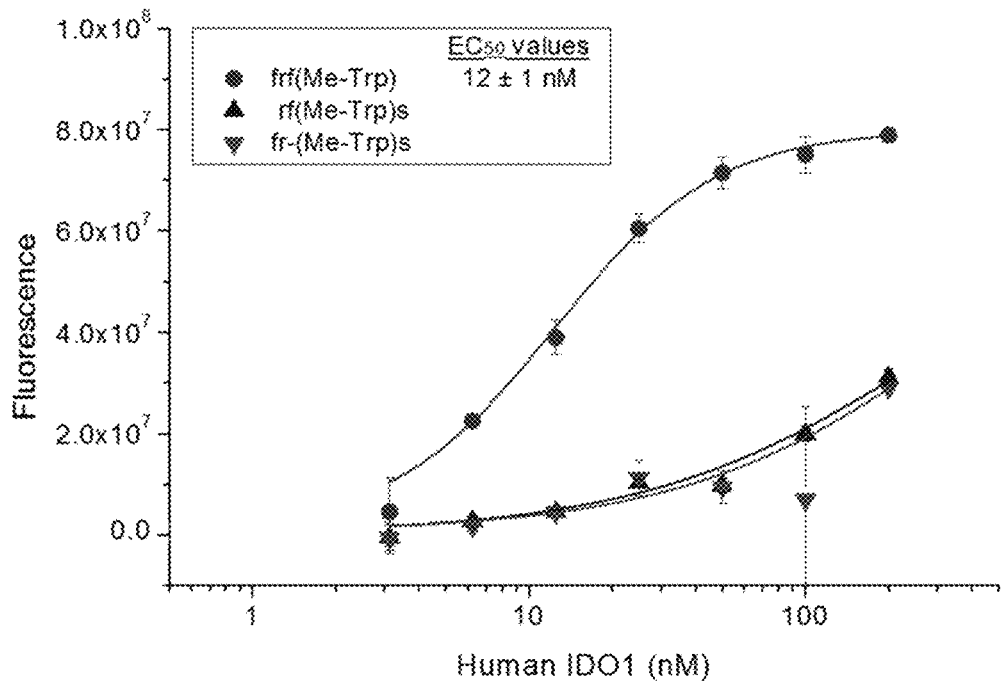

The five single alanine mutants of biotin-PEG$_3$-Cy(frf (Me-Trp)s) (SEQ ID NO:7) were assayed for binding to human IDO1 (FIG. 8A). Me-Trp appears to be the key amino acid for binding. Macrocycle frfas shows the weakest binding to IDO1. Substitution of the N- and C-termini of this macrocycle anchor is tolerated with a small loss of binding affinity. The 4-mer macrocycle frf(Me-Trp) (SEQ ID NO:23) shows a similar binding affinity to the original frf(Me-Trp)s (SEQ ID NO:7), with a similar maximum signal (FIG. 8B).

Some features of epitope targeted IDO1 macrocycles are shown in Table 10.

TABLE 10

Features of Epitope Targeted IDO1 Macrocycles

| Anchor (5-mer) | Epitope | Human IDO EC$_{50}$ (nM) | Mouse IDO EC$_{50}$ (nM) |
|---|---|---|---|
| frf(Me-Trp)s (SEQ ID NO: 7) | 1-N | 18 ± 2 | 36 ± 16 |
| rys(Me-Trp)r (SEQ ID NO: 25) | 2-C | 91 ± 22 | 17 |
| nlf(Me-Trp)(F-Phe) (SEQ ID NO: 31) | 2-C | 19 ± 1 | 89 ± 26 |
| nlw(Me-Trp)r (SEQ ID NO: 28) | 2-N | 51 ± 17 | 48 |
| spww(F-Phe) (SEQ ID NO: 33) | 2-N | 85 ± 18 | 44 |

Example 9: Design and Screening of Heterobiligands of IDO1

Figure 9:
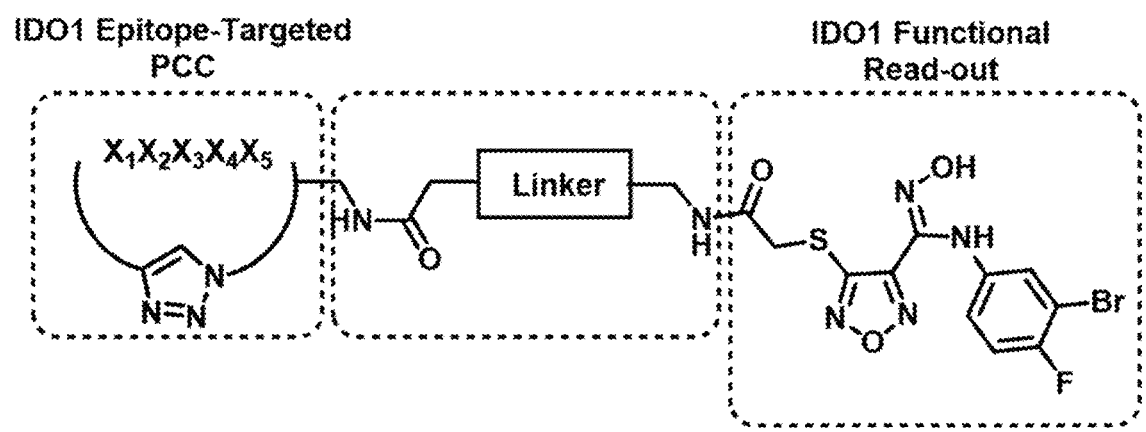
FIG. 9: Diagram of example of a heterobiligand comprising a first ligand having affinity for an epitope on indoleamine 2,3-dioxygenase 1 (IDO1), a linker, and a second ligand, where the second ligand comprises a small molecule inhibitor of IDO1.
Figure 10:
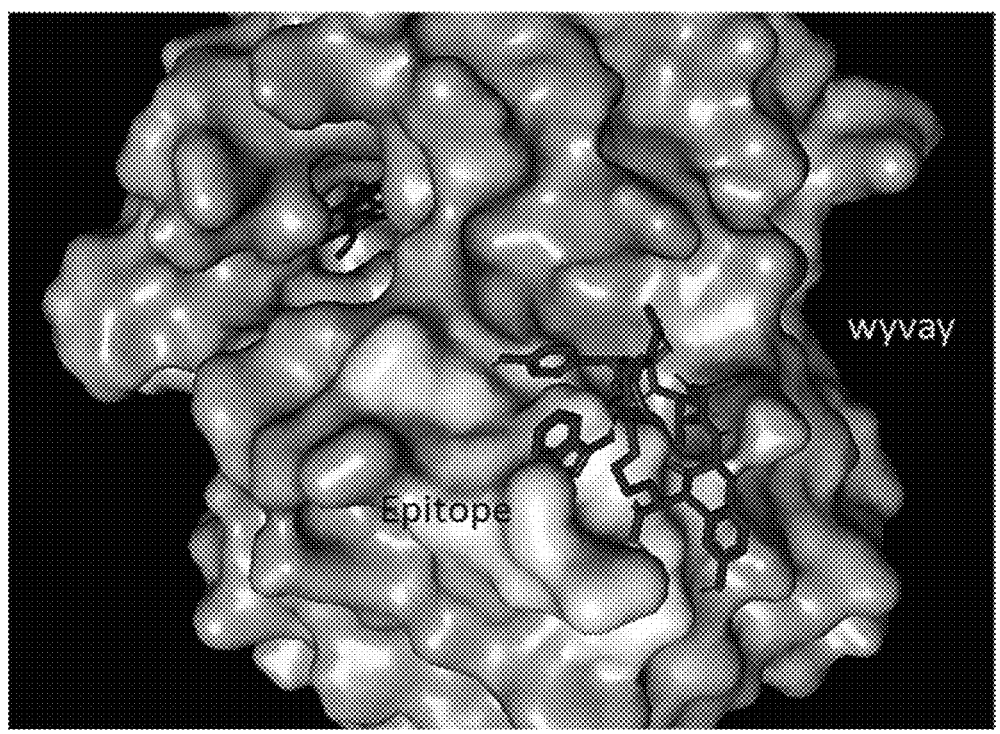
FIG. 10: Crystal structure of human IDO1 with macrocycle wyvay (SEQ ID NO:2) bound to Epitope 1.

Indoleamine 2,3-dioxygenase 1 (IDO1) is an intracellular iron heme-containing protein with high levels of expression in tumors and the associated tumor microenvironment. The cavity of the IDO1 active site was predicted to be unable to accommodate a 5-mer PCC macrocycle. In order to provide a functional readout, a final compound comprised of a PCC IDO1 binder, linker, and IDO1 inhibitor was envisioned (FIG. 9). The surface topology of IDO1 surrounding the active site was examined for possible binding epitopes. Targeting IDO1 epitopes that are further away from the active site would require long linkers to span this distance. Given the established correlation between low molecular weight and successful cellular internalization, limiting the linker length was an important design parameter to target this intracellular protein. A contiguous sequence comprised of 21 residues was identified and designated as epitope 1. The click handle substitution was selected to target the solvent exposed N-terminal region of this epitope and to maximize the catalytic surface of the epitope.

| Epitope 1 | |
|---|---|
| Sequence | GFWEDPKE[F → Az4]AGGSAGQSSVFQ (SEQ ID NO: 39) |
| Charge | −2 |
| Distance to Active site | 19.5 Å |
| Solvent Exposed Surface Area | 991.1 Å$^2$ |

Following the synthesis of the azide-containing epitope, a OBOC library was screened using the click-based protein capture protocol. Two non-canonical amino acids, 4-fluoro-L-phenylalanine (F-Phe), and 1-methyl-L-tryptophan (Me-Trp), were added to the library of sixteen D-amino acids (D-alanine, D-arginine, D-asparagine, D-aspartic acid, D-glutamic acid, glycine, D-histidine, D-leucine, D-lysine, D-phenylalanine, D-proline, D-serine, D-threonine, D-tryptophan, D-tyrosine, and D-valine). Not only did this library modification expand the diversity of the OBOC library, but these unnatural amino acids would assist in cellular penetration and eliminate known metabolic liabilities. Beads containing positive hits were sequenced using MALDI TOF/TOF and synthesized on a 0.1 mmol scale. Hit compounds are shown in Table 11.

TABLE 11

Epitope 1 Hits

| | x2 | x3 | x4 | x5 | x6 | SEQ ID NO |
|---|---|---|---|---|---|---|
| hit1 | y | y | y | Me-Trp | t | 18 |
| hit2 | f | r | f | Me-Trp | s | 7 |
| hit3 | n | d | n | Me-Trp | w | 13 |
| hit4 | n | P | v | F-Phe | w | 14 |
| hit5 | P | P | Me-Trp | s | Me-Trp | 17 |
| hit6 | n | s | f | r | Me-Trp | 6 |
| hit7 | n | t | k | Me-Trp | P | 15 |
| hit8 | G | F-Phe | n | w | k | 11 |
| hit9 | w | Y | r | a | y | 3 |
| hit10 | y | f | n | Me-Trp | Me-Trp | 19 |
| hit11 | F-Phe | n | Me-Trp | Me-Trp | w | 5 |
| hit12 | F-Phe | r | h | l | Me-Trp | 9 |
| hit13 | F-Phe | t | Me-Trp | y | Me-Trp | 10 |
| hit14 | Me-Trp | f | f | k | f | 12 |
| hit15 | n | Me-Trp | P | Me-Trp | f | 16 |

Figure 11A:
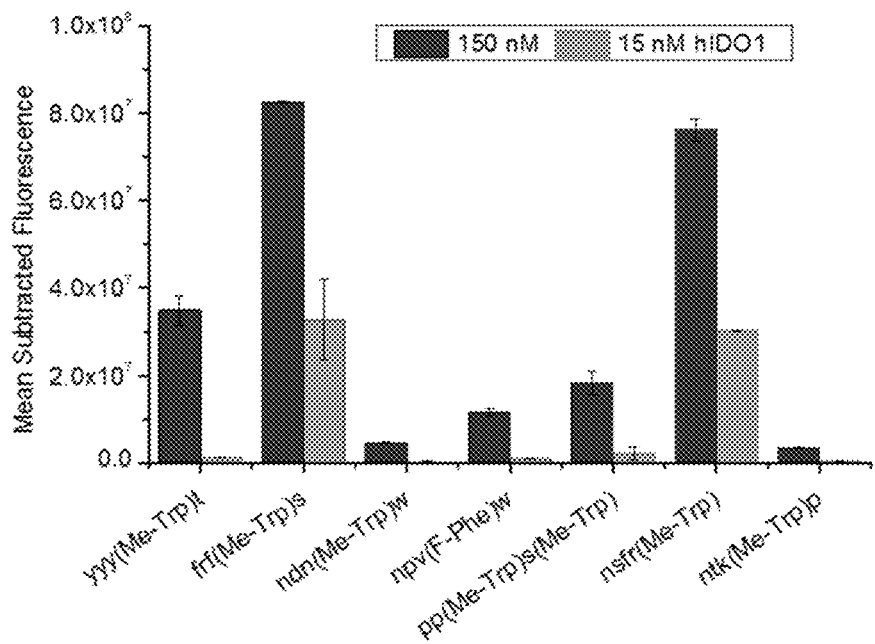
FIGS. 11A-11B: Ranking macrocycles by ELISA. Macrocycles were ranked by the mean fluorescence in a two-point ELISA assay against recombinant human IDO1. 6×His-tagged human IDO1 protein was titrated against biotinylated peptides immobilized on NEUTRAVIDIN® plate, and the amount bound was detected with an enzyme-linked anti-6×His antibody.
Figure 11B:
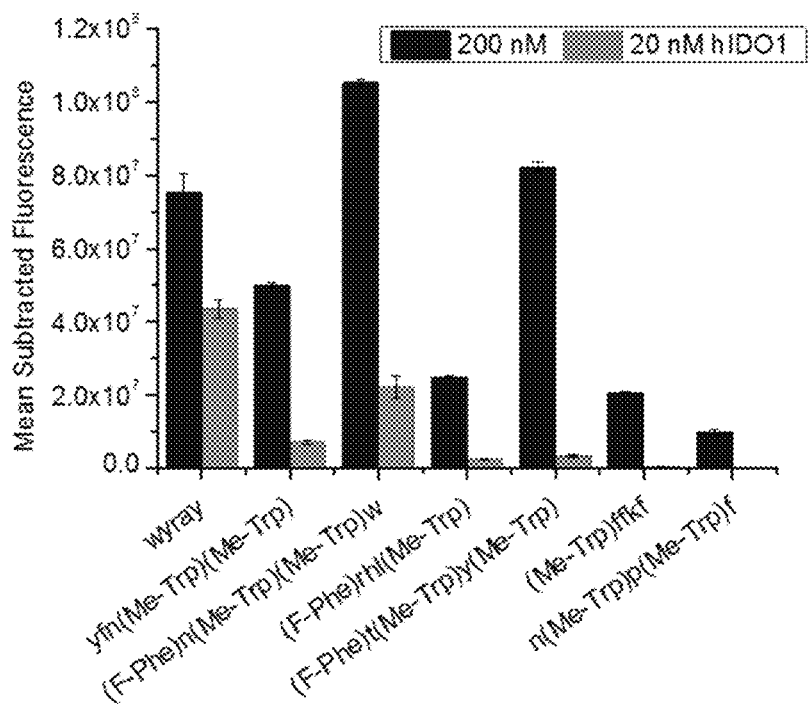

These macrocycles were ranked by the mean fluorescence in a two-point ELISA assay against recombinant human IDO1 (FIGS. 11A and 11B). 6×His-tagged human IDO1 protein was titrated against biotinylated peptides immobilized on NEUTRAVIDIN® plate, and the amount bound was detected with an enzyme-linked anti-6×His antibody. Prioritized hits were frf(Me-Trp)s (SEQ ID NO:7), nsfr(Me-Trp) (SEQ ID NO:6), wyray (SEQ ID NO:3), and (F-Phe)n(Me-Trp)(Me-Trp)w (SEQ ID NO:5).

Binding affinities ($EC_{50}$) were obtained for the prioritized compounds demonstrating a high mean fluorescence and attractive physiochemical properties. Two compounds, frf(Me-Trp)s (SEQ ID NO:7) and wyray (SEQ ID NO:3) were the most potent compounds identified, with binding affinities of 20 nM and 25 nM respectively. The macrocycles nsfr(Me-Trp) (SEQ ID NO:6) and (F-Phe)n(Me-Trp)(Me-Trp)w (SEQ ID NO:5) were less potent, possessing EC50s of 124 nM and 100 nM.

(SEQ ID NO: 7)

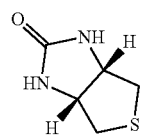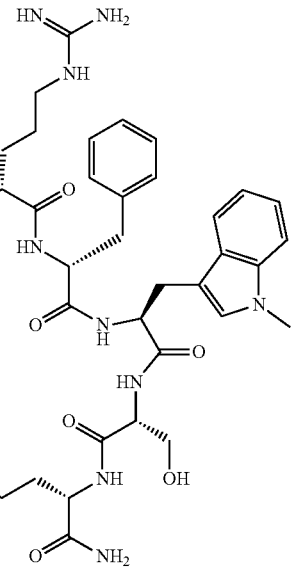

rf(Me-Trp)s (SEQ ID NO: 3)

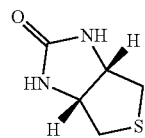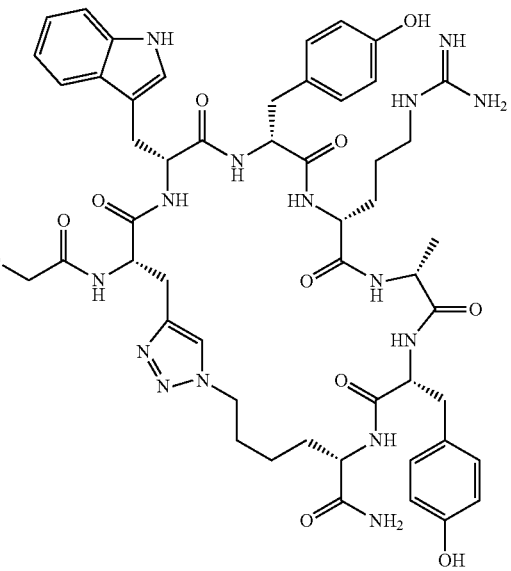

wyray (SEQ ID NO: 6)

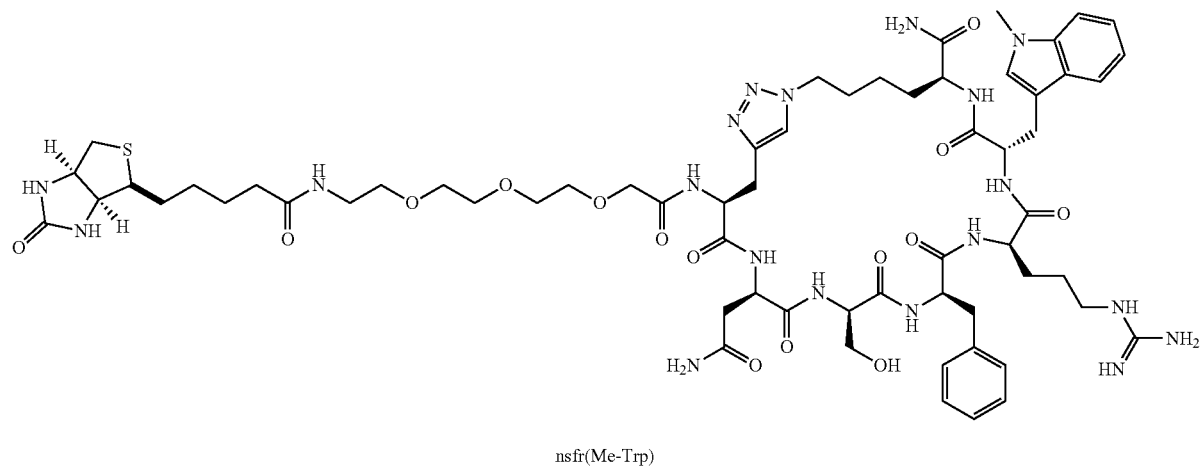

nsfr(Me-Trp)

(SEQ ID NO: 5)

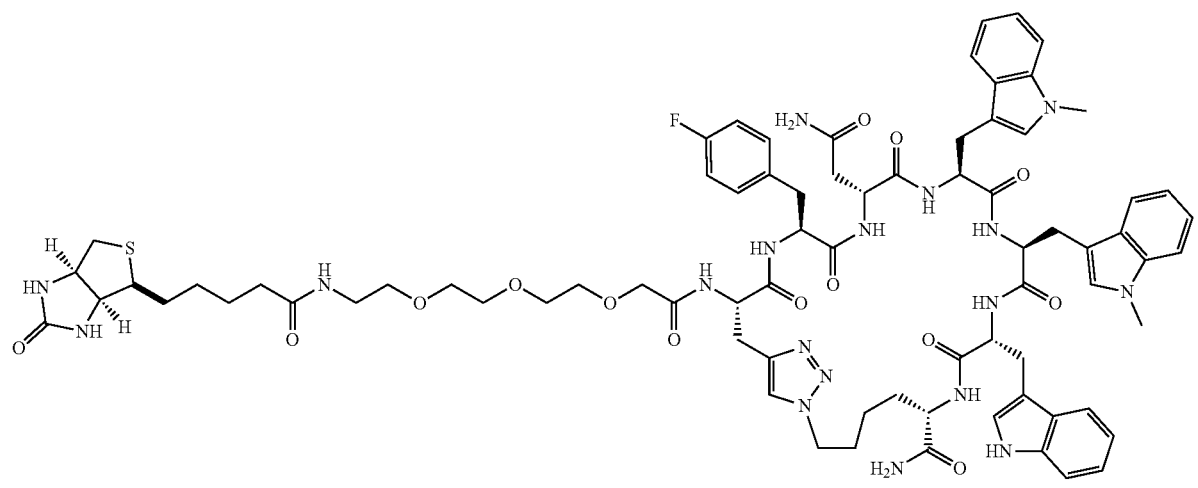

(F-Phe)n(Me-Trp)(Me-Trp)w

Figure 2A:
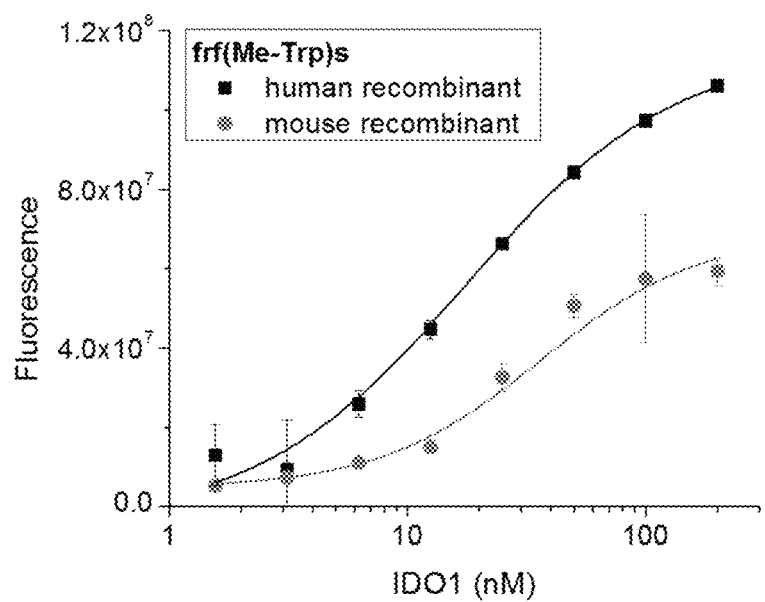
FIGS. 2A-2H: Binding affinities. Binding affinities of anti-human IDO1 macrocyclic peptide ligands against human (black, square) and murine (grey, circle) IDO1 proteins, as measured by ELISA.
Figure 2B:
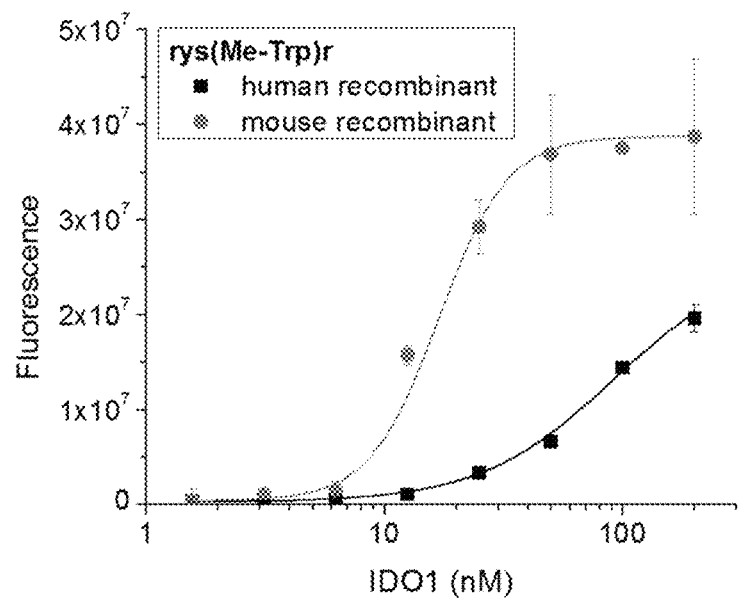
Figure 2C:
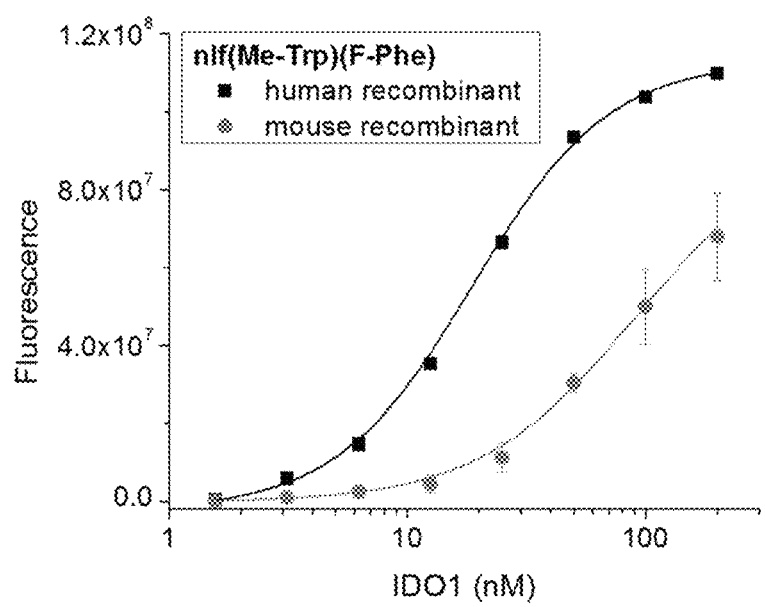
Figure 2D:
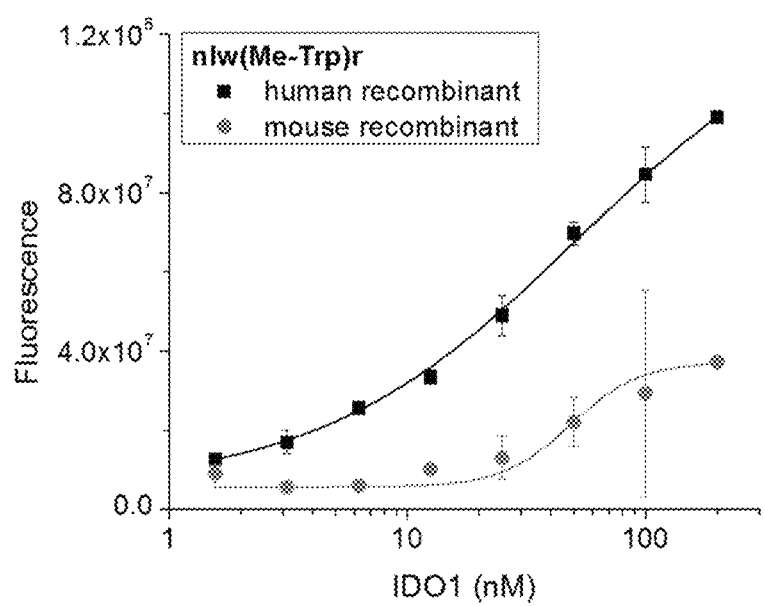
Figure 2E:
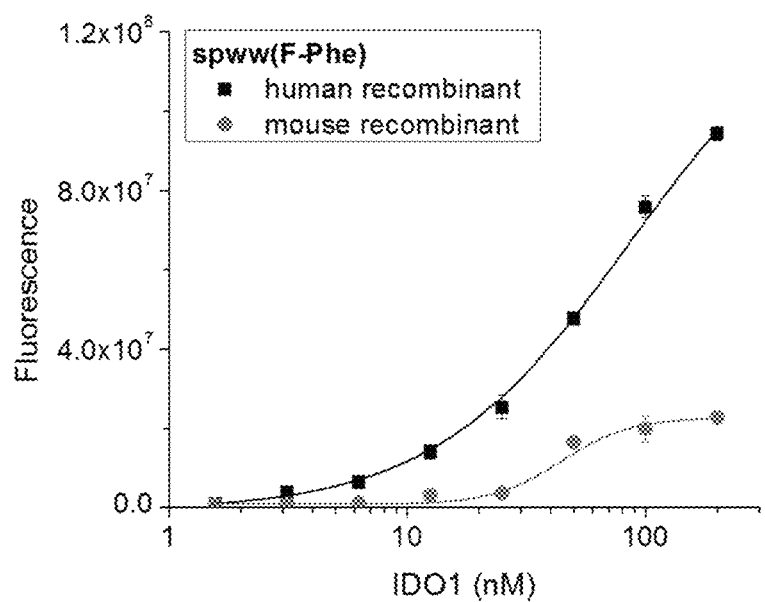
Figure 2F:
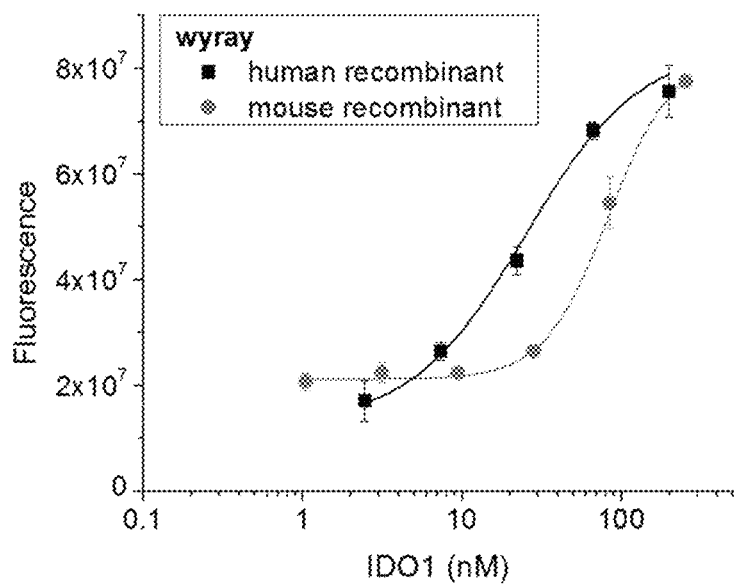
Figure 2G:
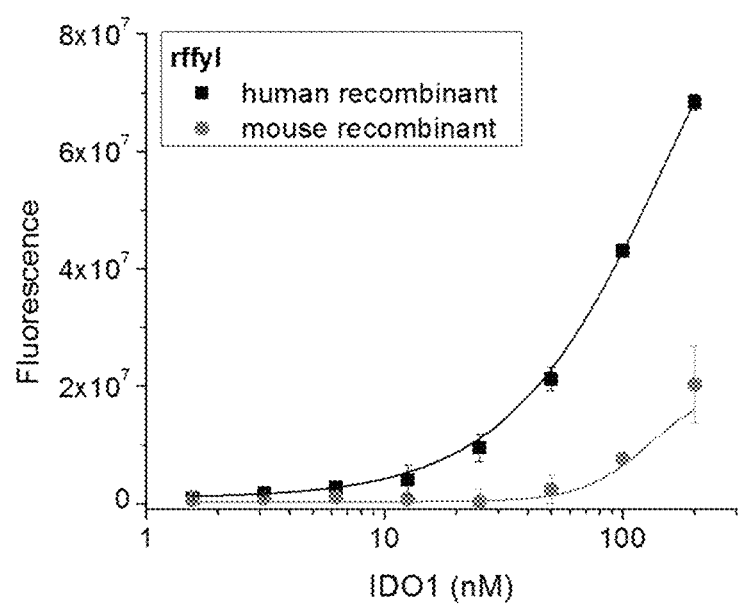
Figure 2H:
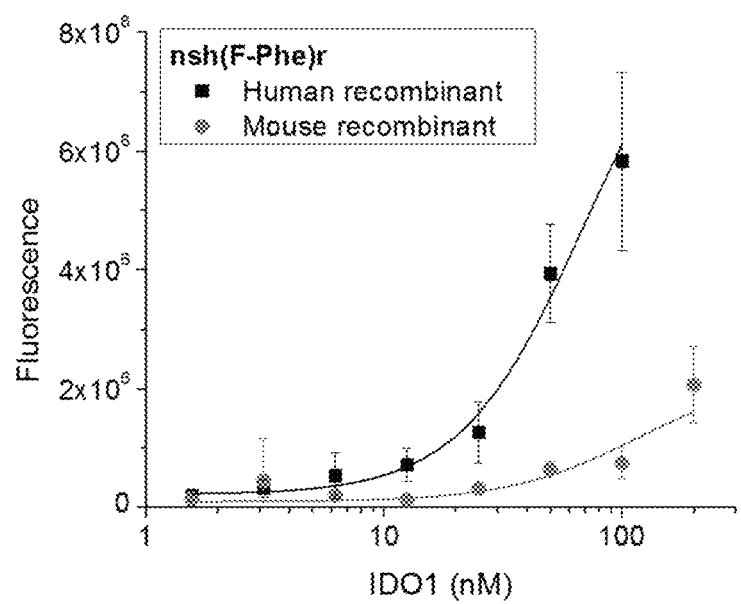

The selectivity of wyray (SEQ ID NO:3) was further profiled. Despite the high levels of sequence homology between human and mouse IDO1, selectivity for the human recombinant protein over mouse is observed by ELISA (FIG. 2F).

```
Human    YEGFWEDPKEFAGGSAGQSSVFQCF

Mu       YEGVWDTPKMFSGGSAGQSSIFQSL

Mac      YEGFWEGPKKFAGGSAAQSSIFQCF
         ***.*: ** *:****.***:**.:
```

Human ,                              (SEQ ID NO: 66)

Murine (Mu),                         (SEQ ID NO: 67)

Macaque (Mac)                        (SEQ ID NO: 68)

To understand the relative contributions of each amino acid position within the macrocycle, an alanine scan was performed. Substituting any of the five positions causes a perturbation to IDO1 binding, indicating that each position contributes to IDO1 binding. The magnitude of the perturbation suggests that Tyr5 is the most critical position, while Trp1 and Tyr2 contributions are moderate (FIG. 12A). Of the five positions, Arg3 was identified as the residue least critical for IDO1 binding. In addition to an alanine scan, ring-reductions were performed to identify 4-mers which maintain IDO1 binding. Deletion of the alanine yields wyry (SEQ ID NO:4), a compound that has a superior binding affinity to that of wyray (SEQ ID NO:3) (FIG. 12B). However, yray and wray are less potent binders. Other variation in the amino acid composition of peptide ligands can include rings size reduction (i.e., reduction in the number of amino acids in the peptide), chirality change for one of the amino acids, N-methylation of the amide backbone, and retroinversion.

Given that the arginine position was both the least important according to the alanine scan, and most detrimental to passive diffusion, D-valine was substituted for Arg3 (Table 12).

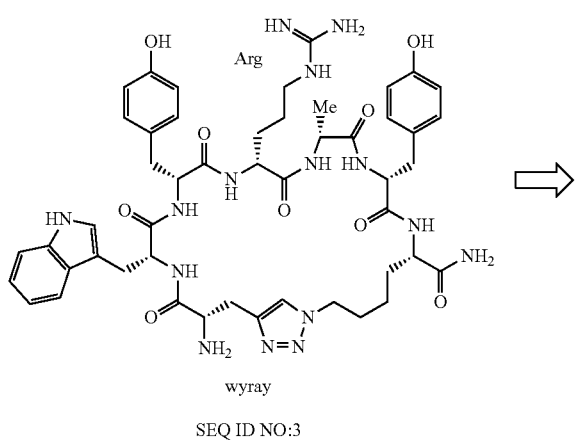

wyray

SEQ ID NO:3

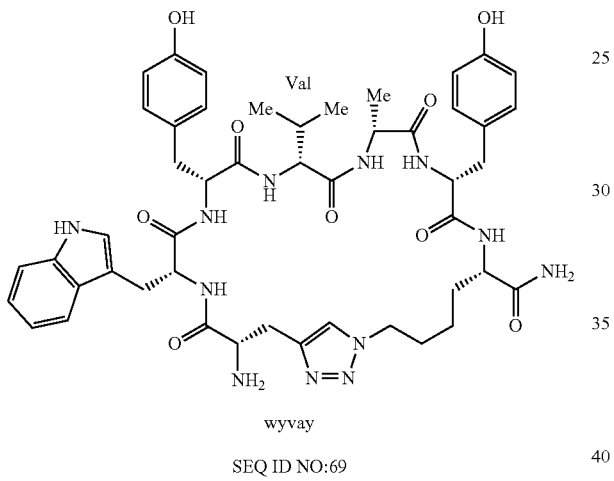

wyvay

SEQ ID NO:69

The calculated lipophilicity (ClogP) increased from −0.74 to 1.85 (peptide wyry (SEQ ID NO:4), with the alanine deleted, had a ClogP of −0.85). The predicted increase in lipophilicity for wyvay (SEQ ID NO:2) was experimentally confirmed by the percent organic (% B) elution during reverse-phase HPLC (RP-HPLC) using a $C_{18}$ column where solvents A=water+0.1% TFA and B=acetonitrile+0.1% TFA. Binding of wyvay (SEQ ID NO:2) to IDO1 was probed by ELISA and the modest loss in binding affinity echoes the results obtained in the alanine scan.

TABLE 12

Comparison of Arg to Val Substitution

| | wyray (SEQ ID NO: 3) | wyvay (SEQ ID NO: 2) |
|---|---|---|
| ClogP | −0.74 | 1.85 |
| HPLC % B | 25.7% | 33.4% |
| $EC_{50}$ | 25 nM | 45 nM |

To further understand the cellular penetration of wyvay (SEQ ID NO:2), two dye-labeled conjugates were prepared. Both FITC and Cy5 labeled wyvay (SEQ ID NO:2) demonstrate dose response cellular uptake (data not show).

The linker length required to span the distance separating the active site and the epitope 1 binding site was modeled computationally. Given that the precise binding mode of the small molecule inhibitor was known, the compound was placed in the active site in such a way that the hydroxyl amidine was interacting with the iron heme. Using CHEMDRAW® 3D, coordinates of the PCC macrocycle were generated and the structure was minimized. The PCC was docked using Autodock Vina, limiting the search area to the solvent-exposed region of epitope 1. The highest scoring pose of wyvay (SEQ ID NO:2) positions the PCC with the N-terminus positioned towards the IDO1 active site (FIG. 10). This fortuitous observation allowed for the modeling of the linker length by using the build and measuring tool in Pymol. The measured distance was 19.5 Å, with a 20 methylene spacer (fully extended and non-minimized) required to connect the small molecule to the PCC.

With an estimation of the correct linker in hand, an active and inactive set were synthesized to probe the binding contributions of the PCC and small molecule inhibitor.

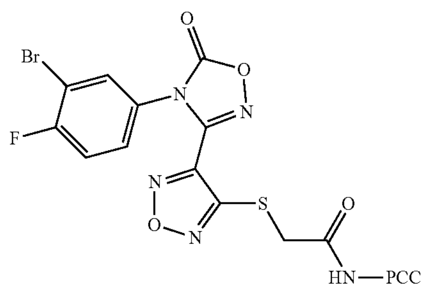

Protected Heme Binder
$IC_{50}$ > 10,000 nM
$EC_{50}$ = 92 nM

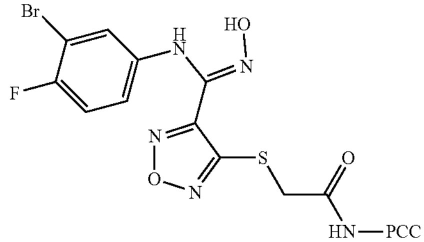

Heme Binder
$IC_{50}$ = 350 nM
$EC_{50}$ = 34 nM

The hydroxyamidine moiety binds directly to the iron heme of IDO1 and is responsible for the inhibitory effects of the small molecule. A $PEG_8$ linker was selected to provide sufficient length and flexibility. In an IDO1 inhibition assay, masking the small molecule as its oxadiazolone reduces the potency ($IC_{50}$) of the heterobiligand from 350 nM to >10,000 nM. However, in the context of an ELISA binding assay, the protected heterobiligand reduced the binding affinity ($EC_{50}$) from 34 nM to 92 nM, a threefold decrease. In concert, these results indicate that while the small molecule is solely responsible for the inhibition of IDO1 (that is, the hydroxyamidine is the key pharmacophore), both the small molecule and PCC contribute to the overall binding affinity. The effect of linker and of protection of the small molecule inhibitor was examined with the heterobiligands protected-Inh-PEG8-wyvay (SEQ ID NO:2), deprotected-Inh-PEG8-wyvay (SEQ ID NO:2), and deprotected-Inh-Gly$_2$-wyvay (SEQ ID NO:2). The data give the following IC$_{50}$s:

```
                                            (SEQ ID NO: 2)
    Protected-Inh-PEG₈-wyvay    IC₅₀ > 10000 nM (SEQ ID NO: 2)
    Deprotected-Inh-PEG₈-wyvay  IC₅₀ = 407 nM (SEQ ID NO: 2)
    Deprotected-Inh-Gly₂-wyvay  IC₅₀ = 1012 nM Deprotected-Inh             IC₅₀ = 616 nM
```

As expected, the protected Inh heterobiligand exhibited minimal inhibition at 10 μM. Revealing (i.e., deprotecting) the hydroxyamidine of the PEG8-linked heterobiligand provides a compound that is more potent (407 nM) than Inh itself (616 nM). The Gly$_2$-linked heterobiligand, which was expected to be too short to span the distance between the active site and Epitope 1, is less active than the small molecule alone.

Confident that the PCC was contributing to the binding of the heterobiligand, the linker length of the PEG spacer was optimized.

Figure 13:
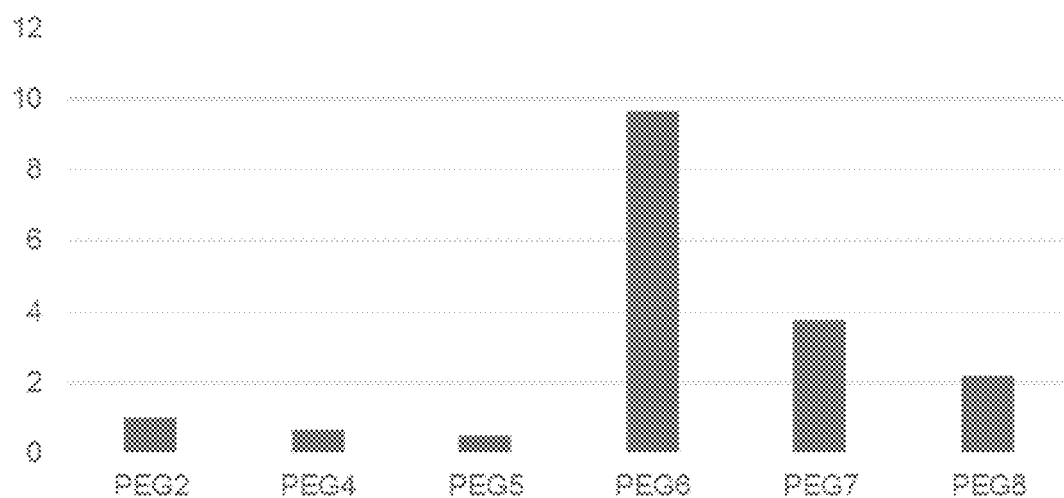
FIG. 13: Graph of IC$_{50}$ of heterobiligands with different linker lengths.

A small set of heterobiligands were synthesized with varying PEG lengths. Three linkers shorter than the predicted length requirement (PEG$_2$, PEG$_4$, and PEG$_5$) provided heterobiligands that were less active than the small molecule alone (FIG. 13). Increasing the spacer to a PEG$_6$ provided a compound that was an order of magnitude more potent than the small molecule and was the best compound identified in the series (FIG. 13). The best inhibition was also observed with a PEG$_6$ spacer.

The data give the following IC$_{50}$s:

```
                                            (SEQ ID NO: 2)
    Inh-PEG₇-wyvay      IC₅₀ = 2003 nM
```

```
                                            (SEQ ID NO: 2)
    Inh-PEG₅-wyvay      IC₅₀ = 2133 nM (SEQ ID NO: 2)
    Inh-PEG₆-wyvay      IC₅₀ = 265 nM Inh                 IC₅₀ = 1051 nM
```

These observations are in agreement with the length requirements predicted by the computational studies.

Related to this, heterobiligands with the alanine deleted (wyry (SEQ ID NO:4)) showed similar linker length effects. Inh-PEG6-wyry (SEQ ID NO:4) was more than three times as potent as Inh alone, while Inh-PEG4-wyry (SEQ ID NO:4) was equal in potency and Inh-PEG8-wyry (SEQ ID NO:4) was significantly less potent than Inh alone.

The data give the following IC$_{50}$s:

```
                                            (SEQ ID NO: 4)
    Inh-PEG₄-wyry       IC₅₀ = 871 nM (SEQ ID NO: 4)
    Inh-PEG₆-wyry       IC₅₀ = 338 nM (SEQ ID NO: 4)
    Inh-PEG₈-wyry       IC₅₀ = 3745 nM Inh                 IC₅₀ = 1089 nM
```

Internalization of fluorescently labeled peptides (using Cy5 or FITC) was measured by concentration dependent flow cytometry of unstimulated HeLa cells incubated for one hour with the peptide. Concentration dependent internalization of both wyvay (SEQ ID NO:2) and wyry (SEQ ID NO:4) was detected, with Cy5 giving a stronger signal than FITC (data not shown). Internalization was also testing using a cellular inhibition assay, which occurs over 48 hours (rather than the one hour for the flow cytometry assay). Internalized FITC-wyvay (SEQ ID NO:2) at 48 hours was compared to one hour in both unstimulated and stimulated HeLa cells (Table 13). Cell penetration of FITC-wyvay (SEQ ID NO:2) increases with time; more internalized FITC-wyvay (SEQ ID NO:2) can be detected at 48 hours compared to one hour. After one hour, no difference in intracellular staining of FITC-wyvay (SEQ ID NO:2) is observed in unstimulated versus stimulated cells. At 48 hours, there is a slight increase in intracellular FITC-wyvay (SEQ ID NO:2) in stimulated compared to unstimulated cells.

TABLE 13

MFIR of Unstimulated and Stimulated HeLa Cells

| | MFIR | |
|---|---|---|
| | unstimulated | stimulated |
| unstained | 1 | 1 |
| 48 hours | 4.91 | 5.27 |
| 1 hour | 2.27 | 2.11 |

Ligands identified for Epitope 2, with a focus on lead ligand nlf(Me-Trp)(F-Phe) (SEQ ID NO:31), were also tested and analyzed. Internalized Cy5-nlf(Me-Trp)(F-Phe) (SEQ ID NO:31) was detected by flow cytometry and imaging; reduced but detectable and concentration dependent FITC-nlf(Me-Trp)(F-Phe) (SEQ ID NO:31) internalization was observed by flow cytometry (data not shown).

Lipophilic modifications to the peptide ligand were also explored as a way to increase cell penetration of the heterobiligands. Using a combination of molecular dynamics (to determine which N—H bonds are involved in intramolecular H-bonds) and docking, three N-methylated heterobiligands were synthesized with methyl added at the third, fifth, or sixth N—H bond in the peptide ligand (Table 14).

TABLE 14

Predicted Binding Affinity and ClogP of N-methyl Modified Peptide Ligands

| (N—H → N—Me) | Binding Affinity (kcal/mol) | ClogP |
|---|---|---|
| — | -7.9 | 1.81 |
| 1 | -7.8 | 2.46 |
| 2 | -7.4 | 2.46 |
| 3 | -8.8 | 2.46 |
| 4 | -7.8 | 2.46 |
| 5 | -8.7 | 2.46 |
| 6 | -8.8 | 2.46 |

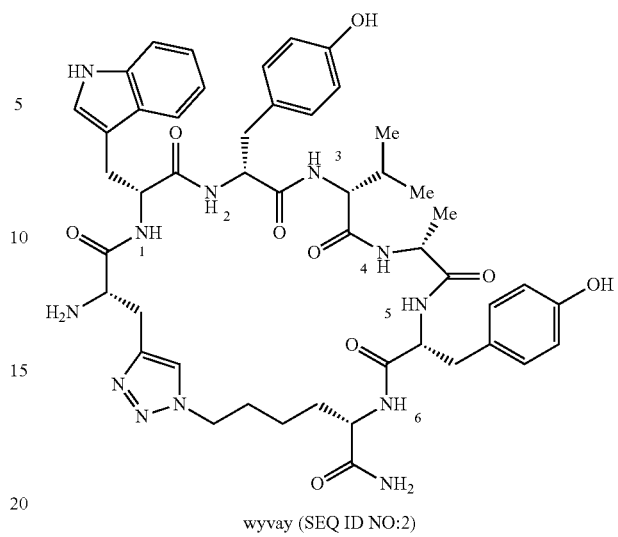

wyvay (SEQ ID NO:2)

Given the PEG optimization experiments, a PEG6 linker was used. The heterobiligands were tested in the IDO1 enzyme inhibition assay. The data give the following $IC_{50}$s:

```
Inh                        IC50 = 928 nM (SEQ ID NO: 2)
Inh-PEG6-wyvay             IC50 = 44 nM (SEQ ID NO:2)
Inh-PEG6-wy(N-Me-v)ay      IC50 = 1455 nM (SEQ ID NO: 2)
Inh-PEG6-wyva(N-Me-y)      IC50 = 3572 nM (SEQ ID NO: 2)
Inh-PEG6-wyvay(N-Me)       IC50 = 622 nM
```

N-methylation of the valine and the Az4 in the peptide provided heterobiligands with similar activity to Inh alone. N-methylation of tyrosine does not appear to be tolerated. The two best N-methylated heterobiligands were tested in the cellular inhibition assay.

N-methylated valine (N-Me-v) in place of valine in Inh-PEG6-wyvay (SEQ ID NO:2) enhanced inhibition in cells by increasing cell penetration (Table 15).

TABLE 15

Comparison of In vitro and Cellular Inhibition

| Heterobiligand | Inhibition Recombinant IDO1 IC50 nM | Inhibition HeLa cells IC50 nM |
|---|---|---|
| Inh-PEG6-wyvay (SEQ ID NO: 2) | 44 | 15313 |
| Inh-PEG6-wyvay(N-Me) (SEQ ID NO: 2) | 622 | 7626 |
| Inh-PEG6-wy(N-Me-v)ay (SEQ ID NO: 2) | 1455 | 157.9 |
| Inh | 928 | 124.8 |

Concentration dependent internalization of peptide wy(N-Me-v)ay (SEQ ID NO:69) was much higher than wyvay (SEQ ID NO:2), wyry (SEQ ID NO:4), or nlf(Me-Trp)(F-

Phe) (SEQ ID NO:31) (data not shown). Inh-PEG6-wy(N-Me-v)ay (SEQ ID NO:69) resulted in cellular inhibition similar activity to Inh alone, consistent with increased cell penetration compared to the unmethylated heterobiligand.

The structures of Inh-PEG6-wyry (SEQ ID NO:4), Inh-PEG6-wyvay (SEQ ID NO:2), Inh-PEG6-wy(N-Me-v)ay (SEQ ID NO:2), and Inh-PEG6-wyvay(N-Me) (SEQ ID NO:2) are shown below.

(SEQ ID NO: 4)

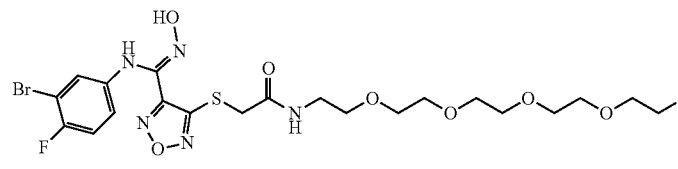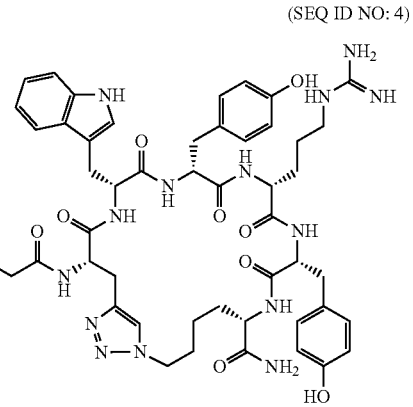

nh-PEG6-wyry (SEQ ID NO: 2)

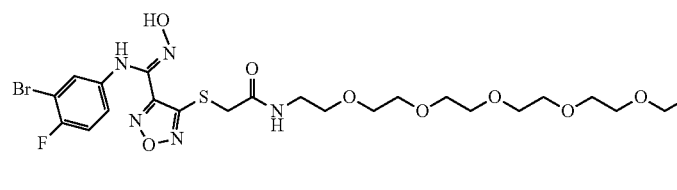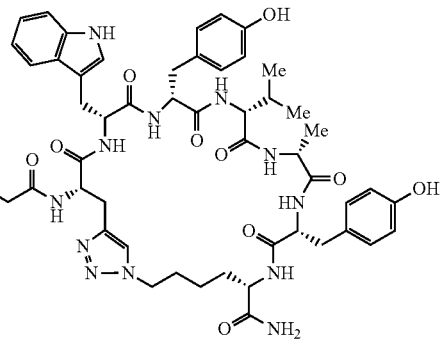

Inh-PEG6-wyry (SEQ ID NO: 2)

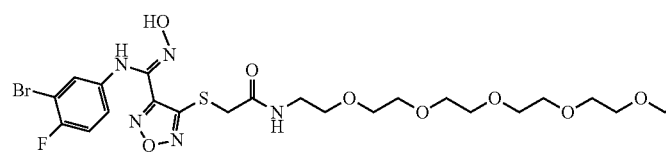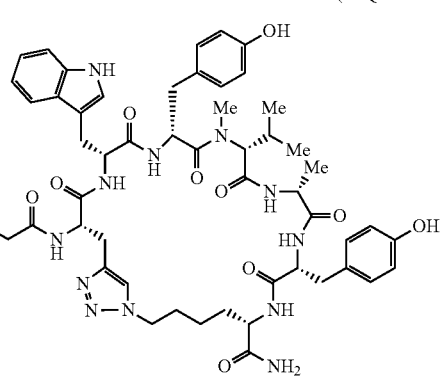

Inh-PEG6-wy(N-Me-v)ay

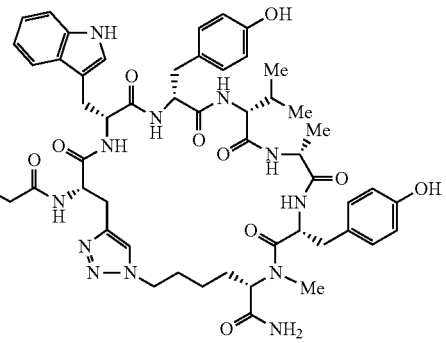

(SEQ ID NO: 2)

Inh-PEG6-wyvay(N-Me)

The calculated ClogP for these heterobiligands are:

| | | |
|---|---|---|
| Inh-PEG$_6$-wyry | ClogP: 0.98 | (SEQ ID NO: 4) |
| Inh-PEG$_6$-wyvay | ClogP: 3.65 | (SEQ ID NO: 2) |
| Inh-PEG$_6$-wy(N-Me-v)ay | ClogP: 4.30 | (SEQ ID NO: 2) |
| Inh-PEG$_6$-wyvay(N-Me) | ClogP: 4.30 | (SEQ ID NO: 2) |

Other peptide modifications can be used to alter or tune the properties of the peptide ligands and heterobiligands. For example, w(Ph-Tyr)(Me-Val)G(Me-Phe) (SEQ ID NO:70) and wyvay-Lys(Myr) (SEQ ID NO:69) can be used. Ph-Tyr is phenyl tyrosine (PhY). Me-Val is methyl valine (MeV). Me-Phe is methyl phenylalanine (MeF). Myr is myristoyl ($C_{14}$). wyvay-Lys(Myr) (SEQ ID NO:69) thus is an example of a lapidated peptide ligand. Lipidation is another way to increase the lipophilicity (e.g., ClogP) of peptide ligands and heterobiligands. w(Ph-Tyr)(Me-Val)G(Me-Phe) (SEQ ID NO:70) is a modified version of wyvay (SEQ ID NO:2) with a greatly increased ClogP. ClogP of w(Ph-Tyr)(Me-Val)G (Me-Phe) (SEQ ID NO:70) is 5.62 while ClogP of wyvay (SEQ ID NO:2) is 1.81. The binding affinity of w(Ph-Tyr)(Me-Val)G(Me-Phe) (SEQ ID NO:70) (EC$_{50}$: 18 nM) is better than that of the heterobiligand Inh-PEG8-wyvay (SEQ ID NO:2) (EC$_{50}$: 36 nM).

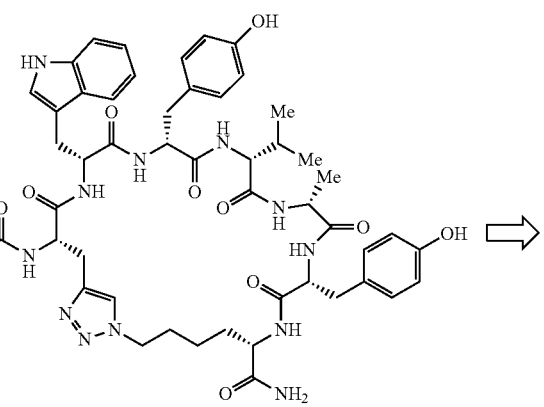

wyvay
BA: -7.9 kcal/mol
ClogP: 1.81

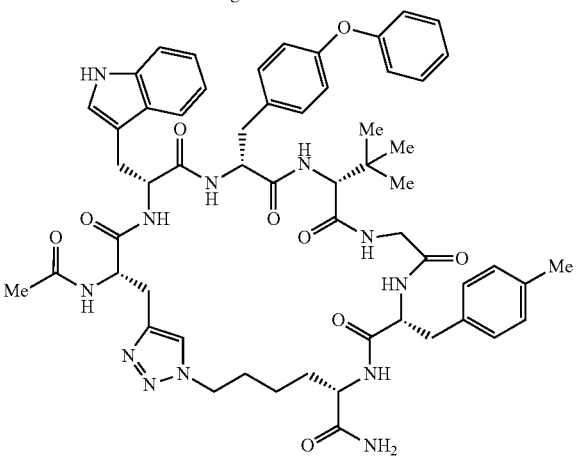

w(PhY)(MeV)G(MF)
BA: -9.9 kcal/mol
ClogP: 5.62

The cyclization method for the peptide ligand can also be varied to provide different chemical groups in the cyclized peptide ligand. For example, ring-closing metathesis (RCM), Gly-RCM, and amide can be used instead of triazole.

In addition to optimizing the length of the spacer, the chemical nature of the linker was probed. Increasing the rigidity of the spacer by incorporating a peptide-based linker decreased the activity of the heterobiligand regardless of the residue composition (Table 16).

| | |
|---|---|
| Inh | IC$_{50}$ = 693 nM |
| | (SEQ ID NO: 2) |
| Inh-BA-(Val)$_3$-wyvay | IC$_{50}$ = 1974 nM |
| | (SEQ ID NO: 2) |
| Inh-PEG$_6$-wyvay | IC$_{50}$ = 200 nM |
| | (SEQ ID NO: 2) |
| Inh-Gly$_7$-wyvay | IC$_{50}$ = 2668 nM |
| | (SEQ ID NO: 2) |
| Inh-BA-PEG$_5$-wyvay | IC$_{50}$ = 1245 nM |

Increasing the rigidity of the linker by utilizing a peptide spacer resulted in compounds with decreased IDO1 activity. Beta-alanine-PEG5, structurally the most similar to PEG6 was not optimal.

TABLE 16

Features of Different Linker Compositions

| Compound | MW | ClogP | % MeCN |
|---|---|---|---|
| Inh-BA-PEG$_5$-wyvay (SEQ ID NO: 2) | 1671 | 3.20 | 46.90% |
| Inh-Gly$_7$-wyvay (SEQ ID NO: 2) | 1722 | 0.86 | 43.72% |
| Inh-BA-(Val)$_3$-wyvay (SEQ ID NO: 2) | 1691 | 2.32 | 45.12% |

Peptide linkers can provide a wider variety of linker properties. For example, GGGGGG (SEQ ID NO:71) can be used as a flexible linker and AEAAAK (SEQ ID NO:72) can be used as a rigid linker. Mixtures of appropriate amino acids can provide linkers of intermediate flexibility. Other peptide linkers include poly-Ala and poly-AABA (SEQ ID NO:73).

Lead compounds prioritized in the recombinant IDO1 inhibition assay were advanced to a cellular IDO1 inhibition assay. IFNγ stimulated HeLa cells treated with PEG6- or PEG8-linked heterobiligands exhibited limited cellular inhibition (Table 17).

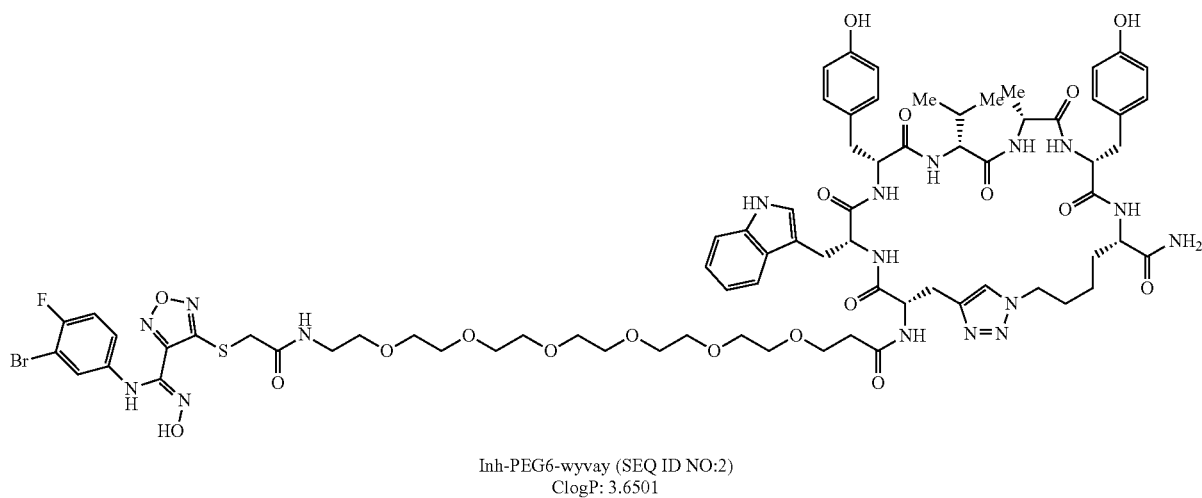 [SMILES: CC(C)[C@H]1NC(=O)[C@@H](Cc2ccc(O)cc2)NC(=O)[C@@H](Cc2c[nH]c3ccccc23)NC(=O)[C@@H](NC(=O)CCOCCOCCOCCOCCOCCOCCNC(=O)CSc2nonc2/C(=N/O)Nc2ccc(F)c(Br)c2)Cc2cn(nn2)CCCC[C@@H](C(N)=O)NC(=O)[C@@H](Cc2ccc(O)cc2)NC(=O)[C@@H](C)NC1=O]

Inh-PEG6-wyvay (SEQ ID NO:2)
ClogP: 3.6501

TABLE 17

Activities of Lead Compounds in Cells

| Heterobiligand | Inhibition Recombinant IDO1 $IC_{50}$ | Inhibition HeLa $IC_{50}$ nM |
|---|---|---|
| Inh-PEG6-wyvay (SEQ ID NO: 2) | 109 nM | 35.7 μM 36.1% inhibition at 8 μM |
| Inh-PEG8-wyvay (SEQ ID NO: 2) | 407 nM | 14.8 μM 77.3% inhibition at 8 μM |
| Inh-PEG6-wyry (SEQ IDNO: 4) | 338 nM | no curve fit 47.8% inhibition at 8 μM |
| Inh | 1089 nM | 244.5 nM 99.6% inhibition at 8 μM |

However, changing the linker by moving the inhibitor linkage away from the small molecule provided a compound with improved cellular activity (Table 18). Modification of the linker increases the lipophilicity of the heterobiligand, providing a compound with superior cell IDO1 inhibition presumably through increased cellular penetration. Additionally, the SP2 hybridized amide bond further away from the small molecule provides additional flexibility which could enable access to a preferred conformation within the active site. Increased cellular uptake or retention of the more lipophilic Inh2-PEG5-wyvay (SEQ ID NO:2) could be responsible for the improved cellular activity.

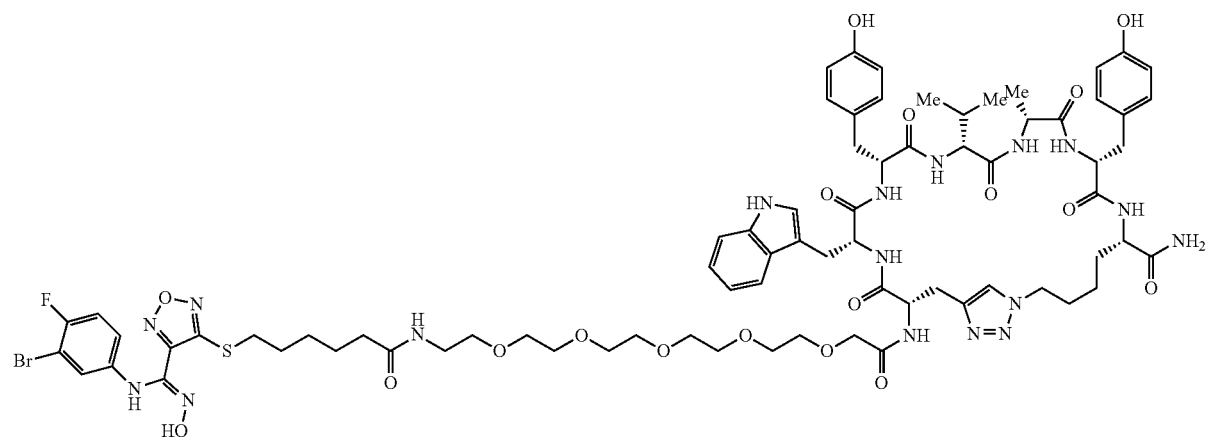

Inh2-PEG5-wyvay (SEQ ID NO:2)
ClogP: 4.829

TABLE 18

Activities Using Different Linker Composition

| Heterobiligand | Inhibition Recombinant IDO1 IC$_{50}$ nM | Inhibition HeLa IC$_{50}$ nM |
|---|---|---|
| Inh2-PEG4-wyvay (SEQ ID NO: 2) | 32410 | 15,501 |
| Inh2-PEG5-wyvay (SEQ ID NO: 2) | 539 | 221 |
| Inh2-PEG6-wyvay (SEQ ID NO: 2) | 6434 | 7383 |
| Inh2 | 343 | 997 |
| Inh | 1089 | 406 |

The structures of Inh and Inh2, as well as the structural differences between Inh-PEG6-wyvay (SEQ ID NO:2) and Inh2-PEG5-wyvay (SEQ ID NO:2) are shown below.

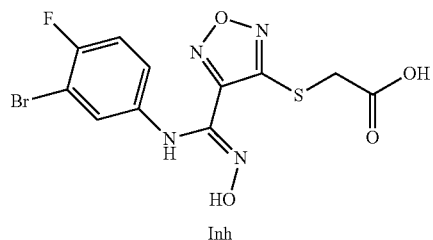

Inh

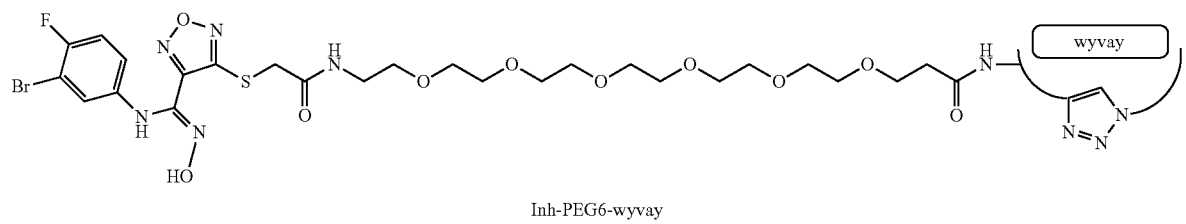

Inh-PEG6-wyvay

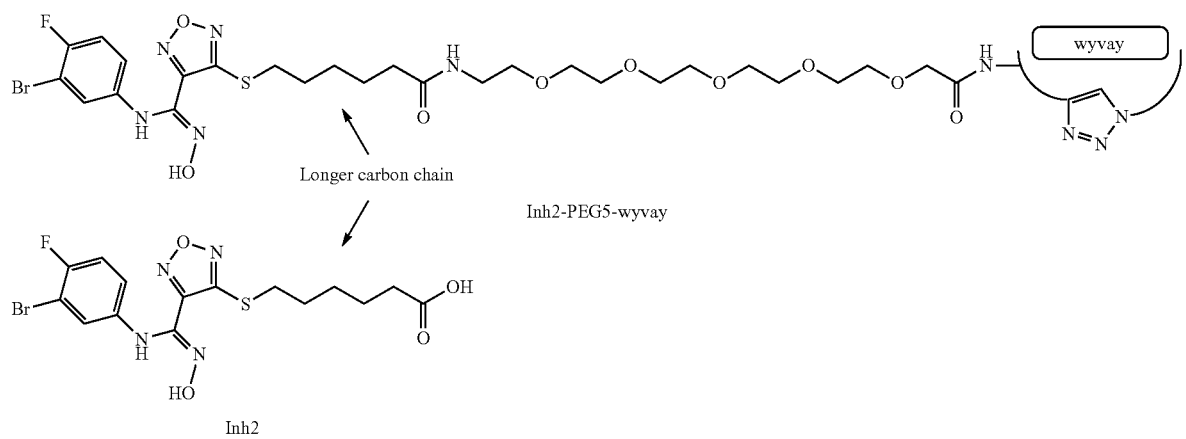

Inh2-PEG5-wyvay

Inh2

A direct comparison of the inhibition of Inh, Inh-PEG6-wyvay (SEQ ID NO:2), Inh2-PEG5-wyvay (SEQ ID NO:2), and Inh2 in HeLa cells shows that Inh2-PEG5-wyvay (SEQ ID NO:2) is more inhibitory than Inh, Inh2, and Inh-PEG6-wyvay (SEQ ID NO:2) (Table 19). Inh-PEG6-wyvay (SEQ ID NO:2) is more inhibitor in vitro but significantly less effective in inhibiting IDO1 in cells. In contrast, Inh2-PEG5-wyvay (SEQ ID NO:2) is more effective in cells than in vitro and is the best cellular inhibitor. The linker modification adds flexibility and increases the lipophilicity, providing a heterobiligand with favorable cellular IDO1 inhibition through increased cell penetration.

TABLE 19

Comparison of In vitro and Cellular Inhibition

| Heterobiligand | Inhibition Human rIDO1 $IC_{50}$ nM | Inhibition HeLa cells $IC_{50}$ nM |
|---|---|---|
| Inh | 1051 | 406 |
| Inh-PEG6-wyvay (SEQ ID NO: 2) | 265 | 35700 (36.1% inhibition at 8 µM) |
| Inh2-PEG5-wyvay (SEQ ID NO: 2) | 539 | 221 |
| Inh2 | 343 | 997 |

Heterobiligands can also be tuned by modifying linkers to increase lipophilicity. For example, d-Hex-Inh-PEG5-wyvay (SEQ ID NO:2) shows IDO1 good inhibition/cell penetration in HeLa cells. Modifications to the linker length reduced IDO1 inhibition: d-Hex-Inh-PEG4-wyvay (SEQ ID NO:2) and d-Hex-Inh-PEG6-wyvay (SEQ ID NO:2) only showed inhibition at higher concentrations. d-Hex-Inh-PEG5-wyvay (SEQ ID NO:2) IDO1 inhibition was reproducible using the same lot in two different experiments; a new lot will be synthesized to test lot to lot reproducibility (data not shown).

In assessing heterobiligands, it was observed that LCMS and fluorescence based readouts of the IDO1 cellular inhibition typically give similar results no toxicity was observed in any of the heterobiligands. SPR was generally used to assess small molecules and peptide selectivity of Heme displacers. For this, absolute RFU values for was ½ to ¼ what is typically observed in this assay format. It was observed that Heme displacers bind APO IDO1 and so oxidation state does not impact binding. Generally, a correlation between binding affinity and activity is observed for the heterobiligands.

The cell penetrant peptide ligands and heterobiligands identified and tested are especially attractive for use in and as in vivo imaging agents and theranostic agents. For example, wyvay (SEQ ID NO:2), wyry (SEQ ID NO:4), and nlf(Me-Trp)(F-Phe) (SEQ ID NO:31) are cell penetrant macrocycles and Inh-PEG6-wy(N-Me-v)ay is a cell penetrant heterobiligand. These peptides and other cell penetrant peptide ligands and heterobiligands can be evaluated for in vivo biodistribution/clearance in normal mice. This can be done by, for example, labeling the peptide/biligand with $^{18}F$ and injecting into normal (healthy) mice. The data can be assessed for delivery, pharmacokinetics/clearance, and non-specific organ uptake of the peptide/biligand, taking into account any healthy mouse baseline IDO1 activity and intracellular compartment kinetics. Compartment transit kinetics should be consistent with the radioisotope half-life in order to have sufficient imaging signal.

Figure 14:
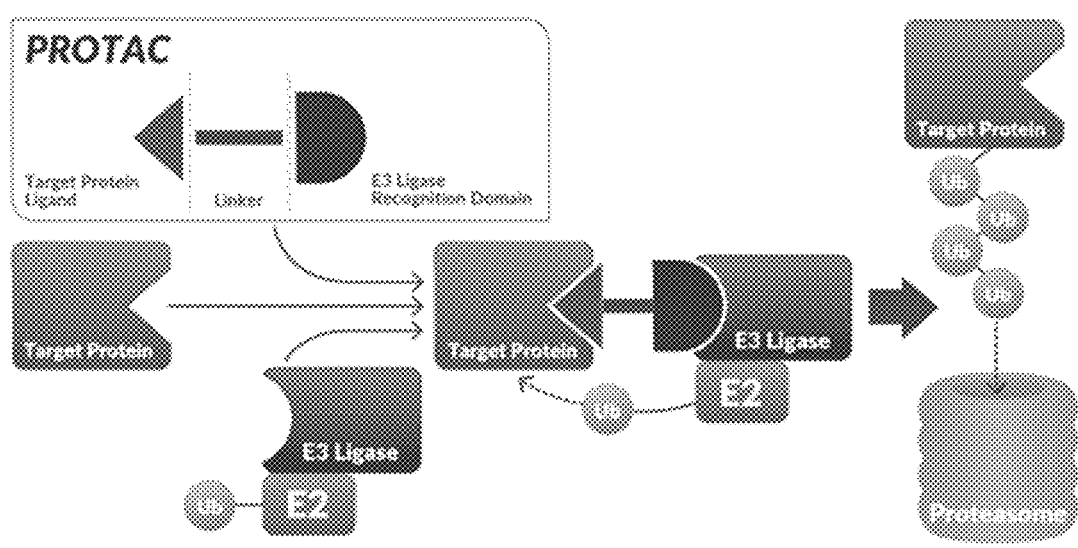
FIG. 14: Diagram of the operation of a PROTAC (Corson et al., ACS Chem Biol. 3(11):677-692 (2008)).

Docking studies estimate that Epitope 2 is too far from the active site of IDO1 to support heterobiligand development. However, Epitope 2 ligands can be used as imaging agents since they can be cell penetrant. Epitope 2 ligands can also be used as a selective targeting moiety to target therapeutic and other agents IDO1 in cells. For example, a proteolysis targeting chimera (PROTAC) can be created from IDO1-binding peptide ligands (as the IDO1 protein binding group), a chemical linker, and E3 ligase ligand (acting as a protein degradation tag). The E3 ligase ligand recruits E3 ligase to the site with the targeting peptide binds (IDO1 in this case). E3 ligase then ubiquitinates the IDO1, which marks IDO1 for degradation. IDO1 binding is maintained when the IDO1-binding peptide ligand is linked to E3 ligase ligand. Operation of a PROTAC is illustrated in FIG. 14 (Corson et al., ACS Chem Biol. 3(11):677-692 (2008)). One important design feature of PROTAC is to have the E3 ligase near to a lysine on IDO1 when the peptide ligand binds to IDO1. Several E3 ligase ligands are available that can recruit E3 ligase to IDO1 when the PROTAC is bound to IDOL. Examples are shown below.

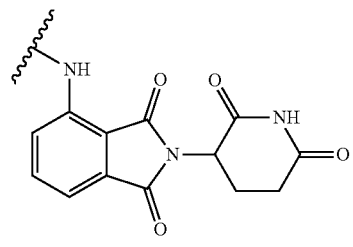

E3 Ligase ligands

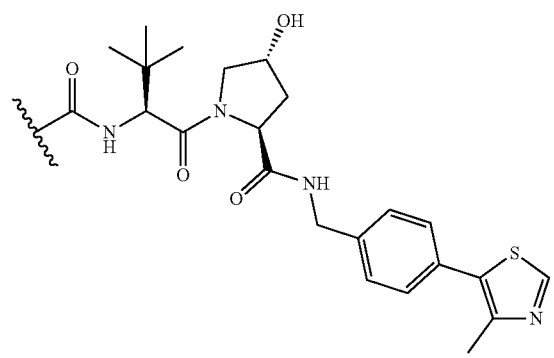

Pomalidomide
Cereblon ligand

-continued

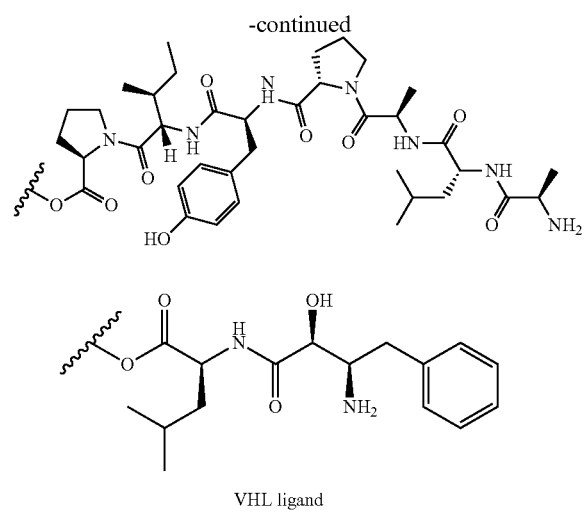
VHL ligand

An example of an Epitope 2C-targeted PROTAC is nlf(Me-Trp)(F-Phe)-PEG2-Gly-Pom (SEQ ID NO:31), the structure of which is shown below.

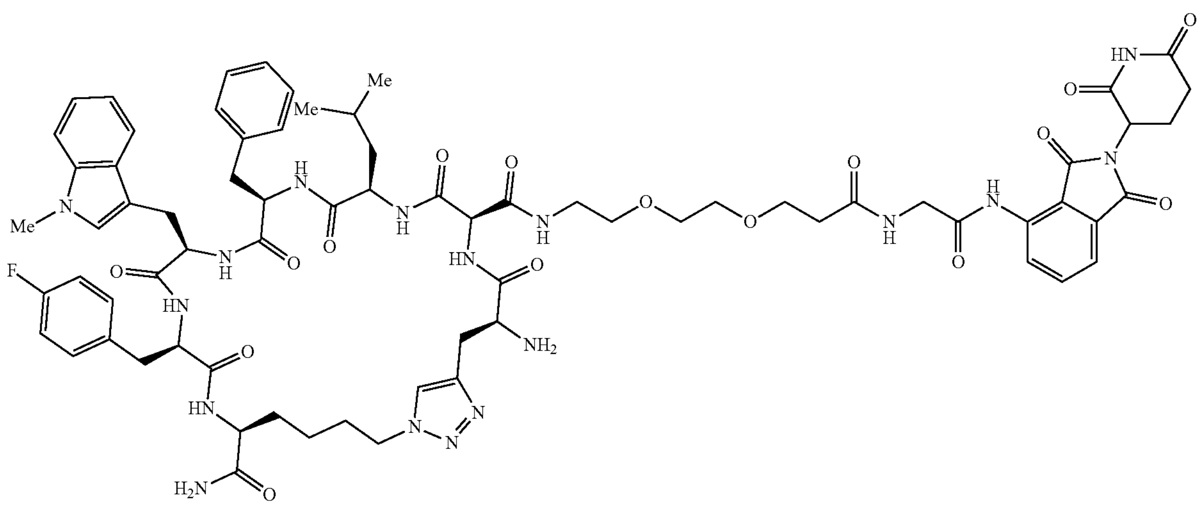 [SMILES: CC(C)C[C@H]1NC(=O)[C@@H](C(=O)NCCOCCOCCC(=O)NCC(=O)Nc2cccc3c2C(=O)N(C2CCC(=O)NC2=O)C3=O)NC(=O)[C@@H](N)Cc2cn(nn2)CCCC[C@@H](C(N)=O)NC(=O)[C@@H](Cc2ccc(F)cc2)NC(=O)[C@@H](Cc2cn(C)c3ccccc23)NC(=O)[C@@H](Cc2ccccc2)NC1=O]

Epitope 2 is positioned near eight lysines: K22, K74, K135*, K136*, K137*, K141*, K161, K179. In addition to pomalidomide, the VHL ligand-coupled peptide is another favored E3 ligase ligand for use with IDO1-binding peptide ligands to promote proteolytic degradation of IDO1. Binding analysis shows that linking VHL to the Epitope 2 peptide ligand nlf(Me-Trp)(F-Phe) (SEQ ID NO:31) does not interfere with the interaction of the peptide ligand with IDO1. The data give the following $EC_{50}$s:

| | |
|---|---|
| | (SEQ ID NO: 31) |
| nlf(Me-Trp)(F-Phe) | $EC_{50}$ = 44 nM |
| | (SEQ ID NO: 31) |
| nlf(Me-Trp)(F-Phe)-Ge-VHL | $EC_{50}$ = 30 nM |
| | (SEQ ID NO: 2) |
| wyvay | $EC_{50}$ = 45 nM |
| Inh | $EC_{50}$ > 1000 nM |

Discussion

This example demonstrates for the first time synthesis of heterobiligands with a peptide ligand linked to a small molecule inhibitor, that the heterobiligands show enhanced inhibition of IDO1 activity compared to the small molecule alone, that design of the linker length and composition of a biligand can be used to tune binding and inhibition as a function of the linker bridging the small molecule and peptide, and effective cellular penetration of peptide and heterobiligand structures.

In this example, PCC macrocycles were selected against an epitope adjacent to the active site of human IDO1 (Epitope 1). A number of lead peptide macrocycles were found that are low nanomolar binders of IDO1. Internalization of these peptide macrocycles into HeLa cells was observed by flow cytometry. Heterobiligands created by attaching a small molecule inhibitor of IDO1 related to espacadostat (INCB024360) to a lead peptide macrocyles via a chemical linker. The heterobiligands exhibited both enhanced affinity and inhibition of IDO1 activity compared to the small molecule inhibitor of IDO1. The inhibition level and effectiveness of the lead heterobiligand was tuned as a function of linker length. The best of the heterobiligands show 10× better inhibition than the small molecule inhibitor of IDO1 alone in an IDO1 enzyme assay. Various strategies were pursued to increase the cell penetration of the heterobiligands, including N-methylation and unnatural amino acid substitutions. N-methylated heterobiligands show both cellular uptake and intracellular inhibition in IDO1 cellular assay in HeLa cells stimulated with IFNγ.

Methods

Coupling of Inhibitor to Macrocycle and Subsequent Deprotection

The purified peptide was taken up in NMP (100 μL/mg). Inhibitor (2.0 equiv., 0.2 M solution in NMP) was added followed by HATU (1.8 equiv., 0.2 M solution in DMSO). DIPEA (5.0 equiv., 0.2 M solution in NMP) was added and the yellow solution stirred at ambient temperature for 2 hours. The crude reaction was diluted with THF to form a 0.02 M solution. To the diluted peptide was added LiOH (20.0 equiv., 1 M aqueous solution). The yellow-orange solution stirred for 20 minutes at ambient temperature. The deprotection reaction was quenched with an equal amount of 1 M aqueous HCl (20.0 equiv.) and the now colorless solution was purified directly using reverse phase HPLC and characterized by MALDI-MS.

IDO1 Inhibition Assay in HeLa Cells Stimulated with IFNγ

Protocol: HeLa cells were trypsinized and diluted to a density of 2×10$^5$ cells/mL in cell culture medium (DMEM+ 10% Fetal Bovine Serum (FBS)+1% Penicillin/Streptomycin). Sterile L-tryptophan was added to the cells at a final concentration of 300 μM. IFNγ at a final concentration of 100 ng/mL was added to HeLa cells to stimulate IDO1 expression. Unstimulated HeLa cells in the absence of IFNγ were used for background subtraction. HeLa cells with or without IFNγ were plated in 96-well Greiner black assay plates at a density of 22,000 cells/well. IDO1 heterobiligands to be tested or Inhibitor as a positive control were serially diluted in nine 3-fold steps in cell culture medium containing 100 ng/mL IFNγ, starting from 125 μM. 8 μL of each compound dilution were then dispensed into the Greiner black 96-well assay plate(s) containing HeLa cells in triplicate, yielding final assay compound concentrations of 8 μM serially diluted to 1.27 nM. The plates were incubated at 37° C. with 5% $CO_2$. After 48 hours, 24 μL of 0.5 M methyl isonipecotate in DMSO were added into each well and the plates were sealed and incubated at 37° C. with 5% $CO_2$ overnight. The resulting fluorescence was measured in a BioTek Synergy H1 plate reader with a 400 nm excitation filter and a 510 nm emission filter. The fluorescence intensity of each well was corrected for the background observed in wells with non-IFNγ-treated cells and was expressed as a fraction of the intensity observed in wells of IFNγ-treated cells with vehicle only.

Cellular Internalization of Fluorescent IDO1 Ligands

Protocol: HeLa cells were cultured to confluence (~500,000 cells) in 6-well plates in cell culture medium (DMEM+ 10% Fetal Bovine Serum (FBS)+1% Penicillin/Streptomycin) or in cell culture medium containing 100 ng/mL IFNγ to stimulate IDO1 expression. The cells were treated with 2 μM or 8 μM macrocyclic IDO1 ligand labeled with either Cy5 or FITC for either 1 hour, 24 hours, or 48 hours as indicated. After treatment, the ligands were aspirated and the cells were washed twice with 1× Phosphate Buffered Saline (PBS). The cells were then harvested by treatment with 0.05% Trypsin-1×EDTA for 5 min at 37° C. Trypsin was quenched by the addition of PBS+2% FBS. The cells in suspension were washed twice in PBS+2% FBS, then resuspended in 500 μL PBS+2% FBS and analyzed for Cy5 or FITC fluorescence using a BD LSR Fortessa X-20 flow cytometer or/and ImageStream X Mark II imaging flow cytometer. Flow Cytometry Standard (fcs) data files were analyzed using FlowJo Software version 10.

Docking Study Protocol and Parameters

The structure was prepared for docking by running an MM2 energy minimization calculation in Chem 3D (CHEMDRAW® suite: Perkin Elmer) and saving the resulting 3D structure as a .pdb file. The .pdb file for the ligand was converted to a .pdbqt file using Autodock Tools. Human IDO1 protein (PDB ID: 5ek3) was used for all docking studies. The small molecule (NLG919 analog) and water molecules were extracted from the structure using PyMOL. The resulting .pdb file was converted to a .pdbqt file using Autodock Tools.

The following parameters including gridbox position and size were used for all docking experiments focused on Epitope 1:

center_x=38.25
center_y=21.914
center_z=33.247
size_x=32
size_y=29
size_z=26

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, sub-group, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise. Thus, for example, reference to "a ligand" includes a plurality of such ligands, reference to "the ligand" is a reference to one or more ligands and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different ligands does not indicate that the listed ligands are obvious one to the other, nor is it an admission of equivalence or obviousness.

Every compound disclosed herein is intended to be and should be considered to be specifically disclosed herein. Further, every subgroup that can be identified within this disclosure is intended to be and should be considered to be specifically disclosed herein. As a result, it is specifically contemplated that any compound, or subgroup of compounds can be either specifically included for or excluded from use or included in or excluded from a list of compounds. For example, as one option, a group of first ligands is contemplated where each first ligand is as described herein but is not wyray (SEQ ID NO:3), wyry (SEQ ID NO:4), nsfr(Me-Trp) (SEQ ID NO:6), frf(Me-Trp)s (SEQ ID NO:7), wyrX3y, wherein X3 is D-Ala or is not present (SEQ ID NOs:3 and 4), X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, arf(Me-Trp)s (SEQ ID NO:20), rf(Me-Trp)s (SEQ ID NO:21), frf(Me-Trp)a (SEQ ID NO:22), frf(Me-Trp) (SEQ ID NO:23), or rf(Me-Trp).

Those skilled in the art will recognize, or be able to ascertain using no more than routine experimentation, many equivalents to the specific embodiments of the method and compositions described herein. Such equivalents are intended to be encompassed by the following claims.

The following references cited throughout the disclosure are hereby incorporated by reference:

Alexander et al., Magn. Reson. Med., 40: 298-310 (1998)
Altschul et al., Nucleic Acids Res. 25:3389-402 (1997)
Corson et al., ACS Chem Biol. 3(11):677-692 (2008)
Edelman et al., Radiology, 177: 45-50 (1990)
Goodrich et al., Invest. Radia, 31: 323-32 (1996)
Iwata et al., Applied radiation and isotopes, 52, 87-92 (2000)
Klemm, *Methods Mol. Biol.* (1984)
Lee et al., *J. Comb. Chem.* (2008)
Liu and Edwards, Chem. Rev., 99:2235-2268 (1999)
Meyers and Miller, Computer Applic. Biol. Sci. 4:11-17 (1988)
Poethko et al., The Journal of Nuclear Medicine, 45, 892-902 (2004)
Schottelius et al., Clinical Cancer Research, 10, 3593-3606 (2004)
Wilson et al., Journal of Labeled Compounds and Radiopharmaceuticals, XXVIII (10), 1189-1199 (1990)
Wooten and Federhen, Comput. Chem. 17:149-63 (1993)
Xnu, Claverie and States, Comput. Chem. 17:191-201 (1993)
International Application No. PCT/US98/01473
International Publication No. PCT/CA94/00395
International Publication No. PCT/CA94/00479
International Publication No. PCT/CA95/00249
International Publication No. PCT/US98/20182
International Publication No. WO 2012/106671
International Publication No. WO 2013/009869
International Publication No. WO 2013/033561
International Publication No. WO 2014/074907
International Publication No. WO 86/06605

International Publication No. WO 91/03200
International Publication No. WO 95/28179
International Publication No. WO 95/28967
International Publication No. WO 96/23526
International Publication No. WO 97/36619
International Publication No. WO 98/18496
International Publication No. WO 98/18496
International Publication No. WO 98/18496
International Publication No. WO 98/18497
International Publication No. WO 98/18497
International Publication No. WO 98/52618
U.S. Application Publication No. 2010/009896
U.S. Pat. No. 4,899,755
U.S. Pat. No. 5,021,556
U.S. Pat. No. 5,075,099
U.S. Pat. No. 5,118,797
U.S. Pat. No. 5,183,653
U.S. Pat. No. 5,364,613
U.S. Pat. No. 5,367,080
U.S. Pat. No. 5,387,409
U.S. Pat. No. 5,474,756
U.S. Pat. No. 5,608,110
U.S. Pat. No. 5,656,254
U.S. Pat. No. 5,662,885
U.S. Pat. No. 5,665,329
U.S. Pat. No. 5,688,487
U.S. Pat. No. 5,720,934
U.S. Pat. No. 5,780,006
U.S. Pat. No. 5,846,519
U.S. Pat. No. 5,849,261
U.S. Pat. No. 5,879,658
U.S. Pat. No. 5,886,142
U.S. Pat. No. 5,976,495
U.S. Pat. No. 6,093,382
U.S. Pat. No. 6,143,274
U.S. Pat. No. 6,143,274

We claim:

1. A heterobiligand comprising a first ligand having affinity for an epitope on indoleamine 2,3-dioxygenase 1 (IDO1), a linker, and a second ligand, wherein the second ligand comprises a small molecule inhibitor of IDO1, wherein the linker links the first ligand and the second ligand, wherein the heterobiligand specifically binds and inhibits IDO1, wherein IDO1 comprises an active site, and wherein the small molecule inhibitor of IDO1 binds the IDO1 active site, wherein the first ligand comprises an amino acid sequence selected from the group consisting of wyvay (SEQ ID NO:2), wyaay (SEQ ID NO: 8), (F-Phe)n(Me-Trp)(Me-Trp)w (SEQ ID NO:5), (F-Phe)rhl(Me-Trp) (SEQ ID NO: 9), (F-Phe)t(Me-Trp)y(Me-Trp) (SEQ ID NO:10), G(F-Phe)nwk (SEQ ID NO:11), (Me-Trp)ffkf (SEQ ID NO:12), ndn(Me-Trp)w (SEQ ID NO:13), npv(F-Phe)w (SEQ ID NO: 14), ntk(Me-Trp)p (SEQ ID NO:15), n(Me-Trp)p(Me-Trp)f (SEQ ID NO:16), pp(Me-Trp)s(Me-Trp) (SEQ ID NO:17), yyy(Me-Trp)t (SEQ ID NO:18), and yfn(Me-Trp)(Me-Trp) (SEQ ID NO:19); and wherein the small molecule inhibitor of IDO1 is

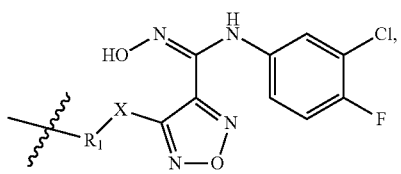

wherein X is S, O, or NH, wherein $R_1$ is —$CH_2$—$R_2$—, —$(CH_2)_n$—$R_2$—, absent, —$(CH_2$—$CH_2$—$O)_m$—$CH_2$—$CH_2$—$R_2$—, or —$CH_2$—$CH_2$—NH—$SO_2$—$R_2$—, wherein $R_2$ is —CO— or —NH—, wherein n is an integer from 2 to 10, wherein m is an integer from 1 to 6.

2. The heterobiligand of claim 1, wherein the small molecule inhibitor of IDO1 is

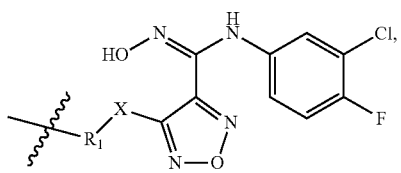

wherein X is S, wherein $R_1$ is —$CH_2$—$R_2$—, and wherein $R_2$ is —CO—.

3. The heterobiligand of claim 1, wherein the small molecule inhibitor of IDO1 is

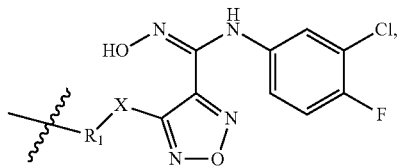

wherein X is NH, and wherein $R_1$ is absent.

4. The heterobiligand of claim 1, wherein the small molecule inhibitor of IDO1 is

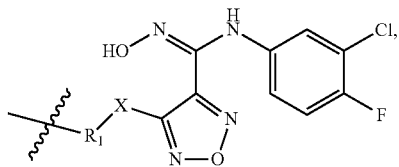

wherein X is NH, wherein $R_1$ is —$CH_2$—$CH_2$—NH—$SO_2$—$R_2$—, and wherein $R_2$ is —NH—.

5. The heterobiligand of claim 1, wherein the first ligand comprises 5 to 9 amino acids.

6. The heterobiligand of claim 1, wherein the epitope comprises the amino acid sequence GFWEDPKEF-AGGSAGQSSVFQ (SEQ ID NO:1).

7. The heterobiligand of claim 1, wherein the first ligand comprises a 1,4-substituted-1,2,3-triazole residue (Tz4) or a 1,5-substituted-1,2,3-triazole residue (Tz5).

8. The heterobiligand of claim 1, wherein the triazole residue is a 1,4-substituted-1,2,3-triazole (Tz4) residue.

9. The heterobiligand of claim 1, wherein the length of the linker is from about 11 Å to about 38 Å.

10. The heterobiligand of claim 1, wherein the heterobiligand further comprises a detectable moiety.

11. The heterobiligand of claim 10, wherein the detectable moiety is selected from the group consisting of biotin, copper-DOTA, biotin-$PEG_3$, aminooxyacetate, [19]FB, [18]FB, and FITC-$PEG_3$.

12. The heterobiligand of claim 10, wherein the detectable moiety is selected from the group consisting of $^{64}$Cu DOTA, $^{68}$Ga DOTA, $^{68}$Ga NOTA, $^{18}$F, Al[18]F NOTA, $^{64}$Cu, $^{68}$Ga, [89]Zr, [124]I, [86]Y, [94m]Tc, [110m]In, $^{11}$C and [76]Br.

13. The heterobiligand of claim 10, wherein the detectable moiety is [18]F.

14. The heterobiligand of claim 1, wherein the heterobiligand has the structure:

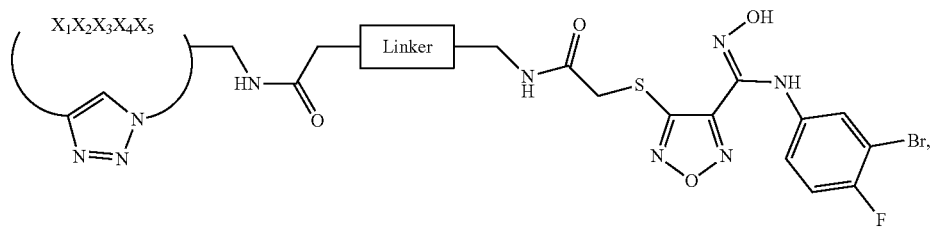

wherein the sequence X₁X₂X₃X₄X₅ is selected from the group consisting of wyvay (SEQ ID NO: 2), (F-Phe)n(Me-Trp)(Me-Trp)w (SEQ ID NO:5), (F-Phe)rhl(Me-Trp) (SEQ ID NO:9), (F-Phe)t(Me-Trp)y(Me-Trp) (SEQ ID NO:10), G(F-Phe)nwk (SEQ ID NO:11), (Me-Trp)ffkf (SEQ ID NO: 12), ndn(Me-Trp)w (SEQ ID NO:13), npv(F-Phe)w (SEQ ID NO:14), ntk(Me-Trp)p (SEQ ID NO:15), n(Me-Trp)p (Me-Trp)f (SEQ ID NO:16), pp(Me-Trp)s(Me-Trp) (SEQ ID NO: 17), yyy(Me-Trp)t (SEQ ID NO:18), and yfn(Me-Trp)(Me-Trp) (SEQ ID NO:19), and wherein the linker is PEG₄, PEG₆, PEG₇, or PEG₈.

15. The heterobiligand of claim 14, wherein the heterobiligand has the following structure:

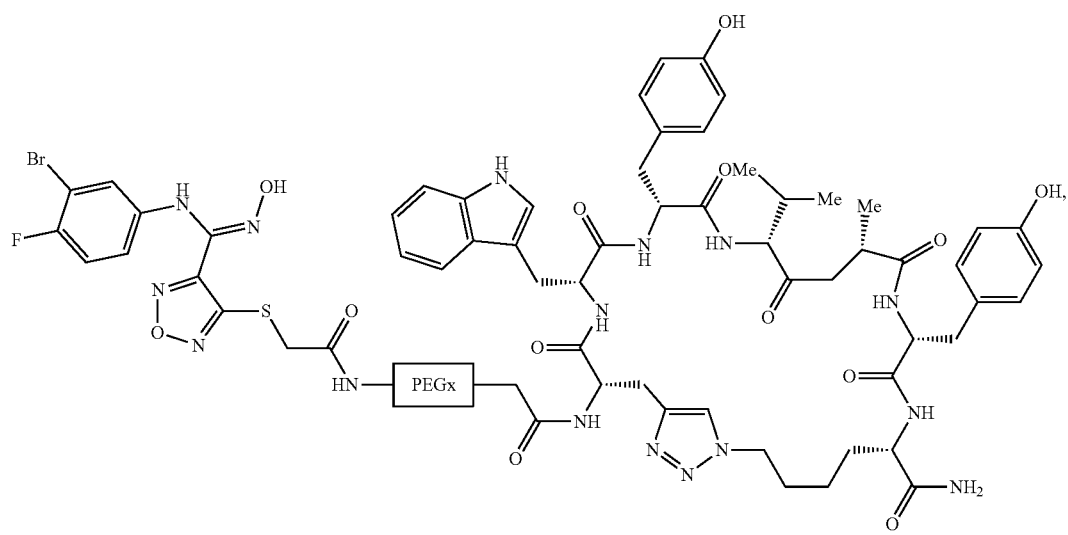

wherein PEG₆, PEG₇, or PEG₈.

16. The heterobiligand of claim 14, wherein the linker is PEG₄ or PEG₆.

17. The heterobiligand of claim 14, wherein the heterobiligand has the structure:

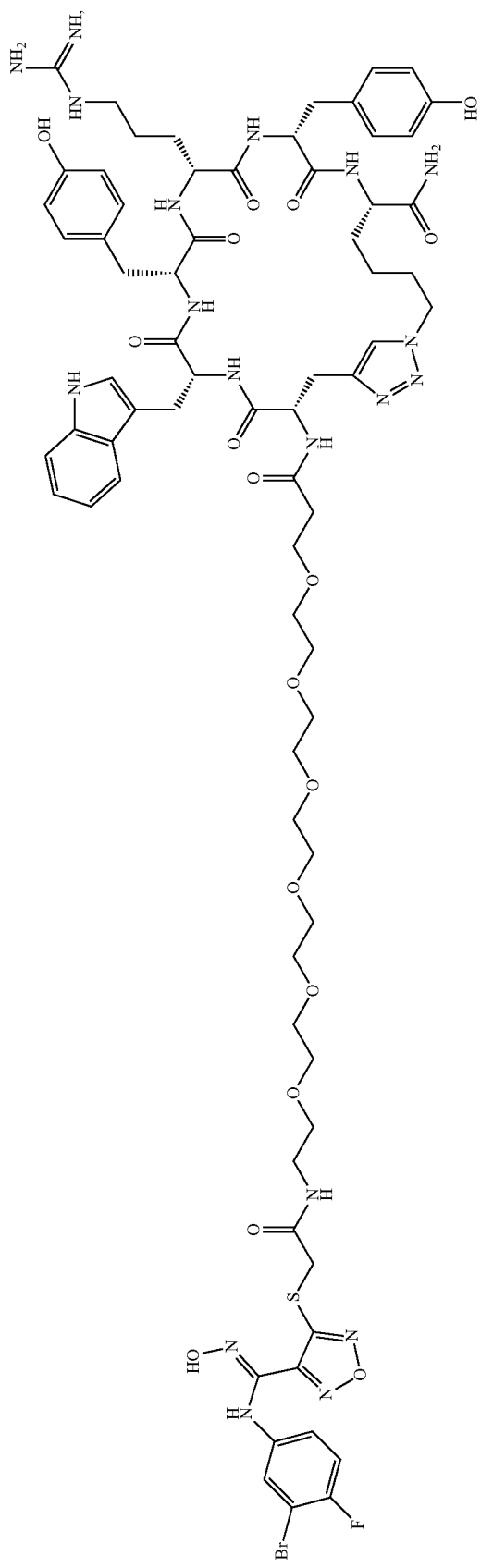
153
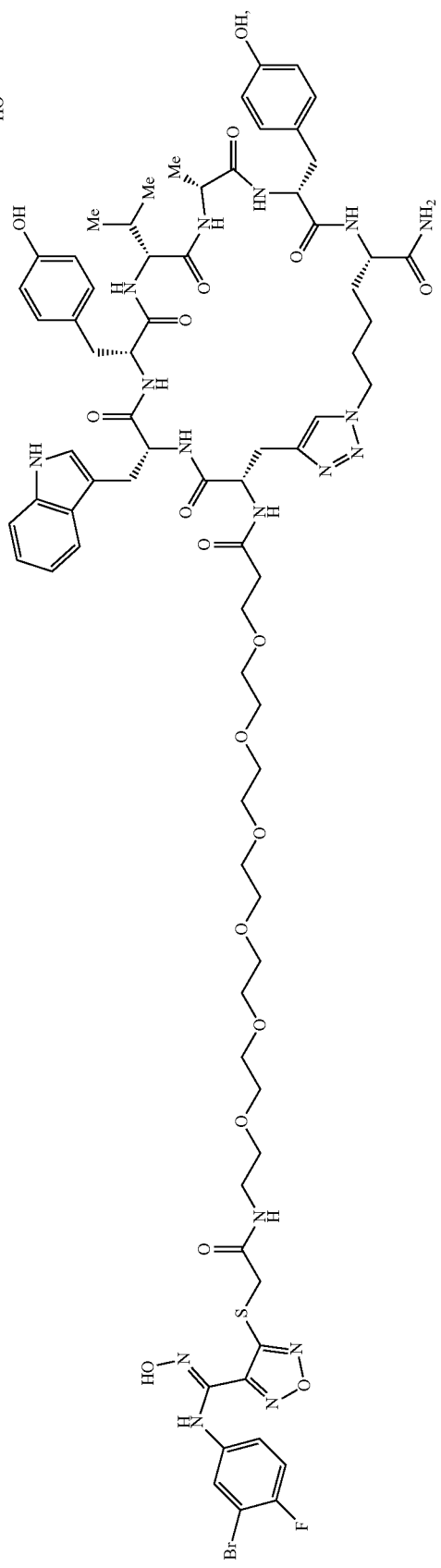
154

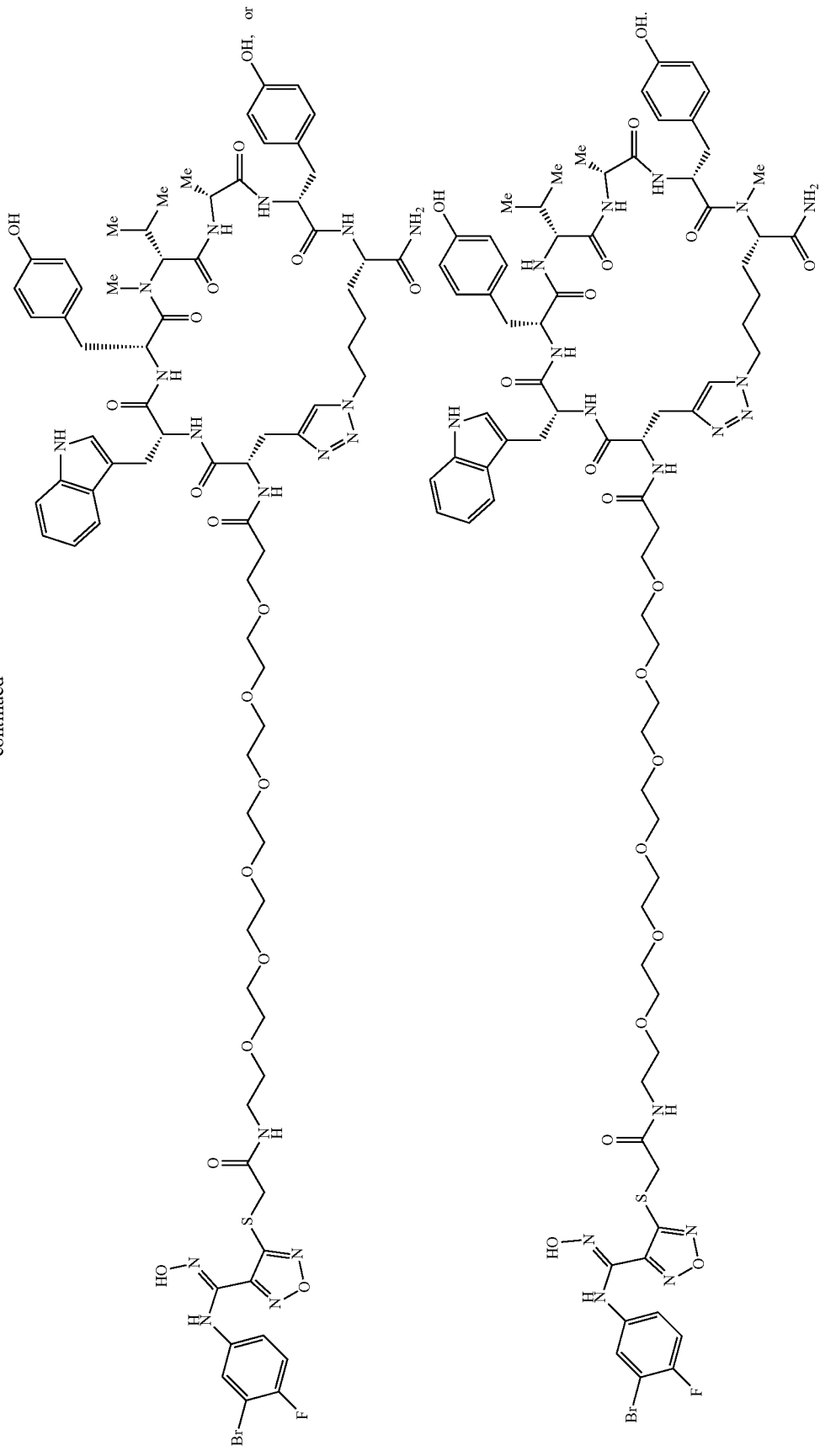

* * * * *

```
                    SEQUENCE LISTING

<160> NUMBER OF SEQ ID NOS: 77

<210> SEQ ID NO 1
   <211> LENGTH: 21
   <212> TYPE: PRT
   <213> ORGANISM: Artificial Sequence
   <220> FEATURE:
   <223> OTHER INFORMATION: Synthetic Peptide

<400> SEQUENCE: 1

Gly Phe Trp Glu Asp Pro Lys Glu Phe Ala Gly Gly Ser Ala Gly Gln
   1               5                   10                  15

Ser Ser Val Phe Gln
               20

<210> SEQ ID NO 2
   <211> LENGTH: 5
   <212> TYPE: PRT
   <213> ORGANISM: Artificial Sequence
   <220> FEATURE:
   <223> OTHER INFORMATION: Synthetic Peptide
   <220> FEATURE:
   <221> NAME/KEY: D-amino acid
   <222> LOCATION: (1)..(5)

<400> SEQUENCE: 2

Trp Tyr Val Ala Tyr
   1               5

<210> SEQ ID NO 3
   <211> LENGTH: 5
   <212> TYPE: PRT
   <213> ORGANISM: Artificial Sequence
   <220> FEATURE:
   <223> OTHER INFORMATION: Synthetic Peptide
   <220> FEATURE:
   <221> NAME/KEY: D-amino acid
   <222> LOCATION: (1)..(5)

<400> SEQUENCE: 3

Trp Tyr Arg Ala Tyr
   1               5

<210> SEQ ID NO 4
   <211> LENGTH: 4
   <212> TYPE: PRT
   <213> ORGANISM: Artificial Sequence
   <220> FEATURE:
```

```
<223> OTHER INFORMATION: Synthetic Peptide
<220> FEATURE:
<221> NAME/KEY: D-amino acid
<222> LOCATION: (1)..(4)

<400> SEQUENCE: 4

Trp Tyr Arg Tyr
1

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-fluoro-L-phenylalanine
<222> LOCATION: (1)..(1)
<220> FEATURE:
<221> NAME/KEY: D-amino acid
<222> LOCATION: (2)..(2)
<220> FEATURE:
<221> NAME/KEY: 1-methyl-Ltryptophan
<222> LOCATION: (3)..(4)
<220> FEATURE:
<221> NAME/KEY: D-amino acid
<222> LOCATION: (5)..(5)

<400> SEQUENCE: 5

Phe Asn Trp Trp Trp
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 1-methyl-Ltryptophan
<222> LOCATION: (5)..(5)

<400> SEQUENCE: 6

Asn Ser Phe Arg Trp
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 7

Phe Arg Phe Trp Ser
1               5

<210> SEQ ID NO 8
<211> LENGTH: 5
```

```
<212> TYPE: PRT
<213> ORGANISM: Artificial Sequence
<220> FEATURE:
<223> OTHER INFORMATION: Synthetic Peptide

<400> SEQUENCE: 8

Trp Tyr Ala Ala Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-fluoro-L-phenylalanine
<222> LOCATION: (1)..(1)
<220> FEATURE:
<221> NAME/KEY: D-amino acid
<222> LOCATION: (2)..(4)
<220> FEATURE:
<221> NAME/KEY: 1-methyl-Ltryptophan
<222> LOCATION: (5)..(5)

<400> SEQUENCE: 9

Phe Arg His Leu Trp
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-fluoro-L-phenylalanine
<222> LOCATION: (1)..(1)
<220> FEATURE:
<221> NAME/KEY: D-amino acid
<222> LOCATION: (2)..(2)
<220> FEATURE:
<221> NAME/KEY: 1-methyl-Ltryptophan
<222> LOCATION: (3)..(3)
<220> FEATURE:
<221> NAME/KEY: D-amino acid
<222> LOCATION: (4)..(4)
<220> FEATURE:
<221> NAME/KEY: 1-methyl-Ltryptophan
<222> LOCATION: (5)..(5)

<400> SEQUENCE: 10

Phe Thr Trp Tyr Trp
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-fluoro-L-phenylalanine
<222> LOCATION: (2)..(2)
<220> FEATURE:
<221> NAME/KEY: D-amino acid
<222> LOCATION: (3)..(5)

<400> SEQUENCE: 11

Gly Phe Asn Trp Lys
1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: 1-methyl-Ltryptophan
<222> LOCATION: (1)..(1)
<220> FEATURE:
<221> NAME/KEY: D-amino acid
<222> LOCATION: (2)..(5)

<400> SEQUENCE: 12

Trp Phe Phe Lys Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 13

Asn Asp Asn Trp Trp
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 4-fluoro-L-phenylalanine
<222> LOCATION: (4)..(4)
<220> FEATURE:
<221> NAME/KEY: D-amino acid
<222> LOCATION: (5)..(5)

<400> SEQUENCE: 14

Asn Pro Val Phe Trp
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)
```

```
<400> SEQUENCE: 15

Asn Thr Lys Trp Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: 1-methyl-Ltryptophan
<222> LOCATION: (2)..(2)
<220> FEATURE:
<221> NAME/KEY: D-amino acid
<222> LOCATION: (3)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 16

Asn Trp Pro Trp Phe
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: 1-methyl-Ltryptophan
<222> LOCATION: (3)..(3)
<220> FEATURE:
<221> NAME/KEY: D-amino acid
<222> LOCATION: (4)..(4)
<220> FEATURE:
<221> NAME/KEY: 1-methyl-Ltryptophan
<222> LOCATION: (5)..(5)

<400> SEQUENCE: 17

Pro Pro Trp Ser Trp
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 18

Tyr Tyr Tyr Trp Thr
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(5)

<400> SEQUENCE: 19

Tyr Phe Asn Trp Trp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 20

Ala Arg Phe Trp Ser
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: 1-methyl-Ltryptophan
<222> LOCATION: (3)..(3)
<220> FEATURE:
<221> NAME/KEY: D-amino acid
<222> LOCATION: (4)..(4)

<400> SEQUENCE: 21

Arg Phe Trp Ser
1

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
```

```
<221> NAME/KEY: D-amino acid
<222> LOCATION: (5)..(5)

<400> SEQUENCE: 22

Phe Arg Phe Trp Ala
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)

<400> SEQUENCE: 23

Phe Arg Phe Trp
1

<210> SEQ ID NO 24
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 24

Leu Pro Pro Ile Leu Val Tyr Ala Asp Cys Val Leu Ala Asn Trp Lys
1               5                   10                  15

Lys Lys Asp Pro Asn Lys
            20

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 25

Arg Tyr Ser Trp Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = D-Ala, D-Arg, D-Asn, D-Asp, D-Glu, Gly, D-His,
      D-Leu, D-Lys, D-Phe, D-Pro, D-Ser, D-Thr, D-Trp, D-Tyr, or D-Val
<222> LOCATION: (1)..(1)
<220> FEATURE:
<221> NAME/KEY: D-amino acid
<222> LOCATION: (2)..(3)
```

```
<220> FEATURE:
<221> NAME/KEY: 1-methyl-Ltryptophan
<222> LOCATION: (4)..(4)
<220> FEATURE:
<221> NAME/KEY: 4-fluoro-L-phenylalanine
<222> LOCATION: (5)..(5)

<400> SEQUENCE: 26

Xaa Leu Phe Trp Phe
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: 1-methyl-Ltryptophan
<222> LOCATION: (3)..(3)
<220> FEATURE:
<221> NAME/KEY: 4-fluoro-L-phenylalanine
<222> LOCATION: (4)..(4)

<400> SEQUENCE: 27

Leu Phe Trp Phe
1

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 28

Asn Leu Trp Trp Arg
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: Xaa = D-Ala, D-Arg, D-Asn, D-Asp, D-Glu, Gly, D-His,
      D-Leu, D-Lys, D-Phe, D-Pro, D-Ser, D-Thr, D-Trp, D-Tyr, or D-Val
<222> LOCATION: (2)..(2)
<220> FEATURE:
<221> NAME/KEY: D-amino acid
<222> LOCATION: (3)..(4)
<220> FEATURE:
<221> NAME/KEY: 4-fluoro-L-phenylalanine
<222> LOCATION: (5)..(5)

<400> SEQUENCE: 29
```

```
Ser Xaa Trp Trp Phe
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 4-fluoro-L-phenylalanine
<222> LOCATION: (4)..(4)

<400> SEQUENCE: 30

Ser Trp Trp Phe
1

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: 4-fluoro-L-phenylalanine
<222> LOCATION: (5)..(5)

<400> SEQUENCE: 31

Asn Leu Phe Trp Phe
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: 4-fluoro-L-phenylalanine
<222> LOCATION: (5)..(5)

<400> SEQUENCE: 32

Ala Leu Phe Trp Phe
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)
```

```
<400> SEQUENCE: 33

Ser Pro Trp Trp Phe
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)

<400> SEQUENCE: 34

Ser Ala Trp Trp Phe
1               5

<210> SEQ ID NO 35
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 4-fluoro-L-phenylalanine
<222> LOCATION: (4)..(4)

<400> SEQUENCE: 35

Ser Trp Trp Phe
1

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 36

Asn Lys Pro Leu Thr Tyr Glu Asn Met Asp Val Leu Phe Ser Phe Arg
1               5                   10                  15

<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 37

Arg Phe Phe Tyr Leu
1               5

<210> SEQ ID NO 38
<211> LENGTH: 5
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 4-fluoro-L-phenylalanine
<222> LOCATION: (4)..(4)
<220> FEATURE:
<221> NAME/KEY: D-amino acid
<222> LOCATION: (5)..(5)

<400> SEQUENCE: 38

Asn Ser His Phe Arg
1               5

<210> SEQ ID NO 39
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = L-azidolysine
<222> LOCATION: (9)..(9)

<400> SEQUENCE: 39

Gly Phe Trp Glu Asp Pro Lys Glu Xaa Ala Gly Gly Ser Ala Gly Gln
1               5                   10                  15

Ser Ser Val Phe Gln
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = L-azidolysine
<222> LOCATION: (12)..(12)

<400> SEQUENCE: 40

Leu Pro Pro Ile Leu Val Tyr Ala Asp Cys Val Xaa Ala Asn Trp Lys
1               5                   10                  15

Lys Lys Asp Pro Asn Lys
            20

<210> SEQ ID NO 41
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = L-azidolysine
<222> LOCATION: (10)..(10)

<400> SEQUENCE: 41

Asn Lys Pro Leu Thr Tyr Glu Asn Met Xaa Val Leu Phe Ser Phe Arg
1               5                   10                  15

<210> SEQ ID NO 42
<211> LENGTH: 402
<212> TYPE: PRT
<213> ORGANISM: Homo sapiens

<400> SEQUENCE: 42

Ala His Ala Met Glu Asn Ser Trp Thr Ile Ser Lys Glu Tyr His Ile
```

```
               1               5                  10                 15
            Asp Glu Glu Val Gly Phe Ala Leu Pro Asn Pro Gln Glu Asn Leu Pro
                           20                  25                 30
            Asp Phe Tyr Asn Asp Trp Met Phe Ile Ala Lys His Leu Pro Asp Leu
                           35                  40                 45
            Ile Glu Ser Gly Gln Leu Arg Glu Arg Val Glu Lys Leu Asn Met Leu
                           50                  55                 60
            Ser Ile Asp His Leu Thr Asp His Lys Ser Gln Arg Leu Ala Arg Leu
             65                 70                  75                 80
            Val Leu Gly Cys Ile Thr Met Ala Tyr Val Trp Gly Lys Gly His Gly
                              85                  90                 95
            Asp Val Arg Lys Val Leu Pro Arg Asn Ile Ala Val Pro Tyr Cys Gln
                           100                 105                110
            Leu Ser Lys Lys Leu Glu Leu Pro Pro Ile Leu Val Tyr Ala Asp Cys
                           115                 120                125
            Val Leu Ala Asn Trp Lys Lys Lys Asp Pro Asn Lys Pro Leu Thr Tyr
                           130                 135                140
            Glu Asn Met Asp Val Leu Phe Ser Phe Arg Asp Gly Asp Cys Ser Lys
            145                 150                 155                160
            Gly Phe Phe Leu Val Ser Leu Leu Val Glu Ile Ala Ala Ser Ala
                              165                 170                175
            Ile Lys Val Ile Pro Thr Val Phe Lys Ala Met Gln Met Gln Glu Arg
                           180                 185                190
            Asp Thr Leu Leu Lys Ala Leu Leu Glu Ile Ala Ser Cys Leu Glu Lys
                           195                 200                205
            Ala Leu Gln Val Phe His Gln Ile His Asp His Val Asn Pro Lys Ala
                           210                 215                220
            Phe Phe Ser Val Leu Arg Ile Tyr Leu Ser Gly Trp Lys Gly Asn Pro
            225                 230                 235                240
            Gln Leu Ser Asp Gly Leu Val Tyr Glu Gly Phe Trp Glu Asp Pro Lys
                           245                 250                255
            Glu Phe Ala Gly Gly Ser Ala Gly Gln Ser Ser Val Phe Gln Cys Phe
                           260                 265                270
            Asp Val Leu Leu Gly Ile Gln Gln Thr Ala Gly Gly His Ala Ala
                           275                 280                 285
            Gln Phe Leu Gln Asp Met Arg Arg Tyr Met Pro Pro Ala His Arg Asn
                           290                 295                300
            Phe Leu Cys Ser Leu Glu Ser Asn Pro Ser Val Arg Glu Phe Val Leu
            305                 310                 315                320
            Ser Lys Gly Asp Ala Gly Leu Arg Glu Ala Tyr Asp Ala Cys Val Lys
                           325                 330                335
            Ala Leu Val Ser Leu Arg Ser Tyr His Leu Gln Ile Val Thr Lys Tyr
                           340                 345                350
            Ile Leu Ile Pro Ala Ser Gln Gln Pro Lys Glu Asn Lys Thr Ser Glu
                           355                 360                365
            Asp Pro Ser Lys Leu Glu Ala Lys Gly Thr Gly Thr Asp Leu Met
                           370                 375                380
            Asn Phe Leu Lys Thr Val Arg Ser Thr Thr Glu Lys Ser Leu Leu Lys
            385                 390                 395                400
            Glu Gly

<210> SEQ ID NO 43
<211> LENGTH: 405
```

<212> TYPE: PRT
<213> ORGANISM: Mus musculus

<400> SEQUENCE: 43

```
Ala Leu Ser Lys Ile Ser Pro Thr Glu Gly Ser Arg Arg Ile Leu Glu
1               5                   10                  15

Asp His His Ile Asp Glu Asp Val Gly Phe Ala Leu Pro His Pro Leu
            20                  25                  30

Val Glu Leu Pro Asp Ala Tyr Ser Pro Trp Val Leu Val Ala Arg Asn
        35                  40                  45

Leu Pro Val Leu Ile Glu Asn Gly Gln Leu Arg Glu Val Glu Lys
    50                  55                  60

Leu Pro Thr Leu Ser Thr Asp Gly Leu Arg Gly His Arg Leu Gln Arg
65                  70                  75                  80

Leu Ala His Leu Ala Leu Gly Tyr Ile Thr Met Ala Tyr Val Trp Asn
                85                  90                  95

Arg Gly Asp Asp Val Arg Lys Val Leu Pro Arg Asn Ile Ala Val
            100                 105                 110

Pro Tyr Cys Glu Leu Ser Glu Lys Leu Gly Leu Pro Ile Leu Ser
        115                 120                 125

Tyr Ala Asp Cys Val Leu Ala Asn Trp Lys Lys Asp Pro Asn Gly
    130                 135                 140

Pro Met Thr Tyr Glu Asn Met Asp Ile Leu Phe Ser Phe Pro Gly Gly
145                 150                 155                 160

Asp Cys Asp Lys Gly Phe Phe Leu Val Ser Leu Val Glu Ile Ala
            165                 170                 175

Ala Ser Pro Ala Ile Lys Ala Ile Pro Thr Val Ser Ser Ala Val Glu
            180                 185                 190

Arg Gln Asp Leu Lys Ala Leu Glu Lys Ala Leu His Asp Ile Ala Thr
            195                 200                 205

Ser Leu Glu Lys Ala Lys Glu Ile Phe Lys Arg Met Arg Asp Phe Val
            210                 215                 220

Asp Pro Asp Thr Phe Phe His Val Leu Arg Ile Tyr Leu Ser Gly Trp
225                 230                 235                 240

Lys Cys Ser Ser Lys Leu Pro Glu Gly Leu Leu Tyr Glu Gly Val Trp
                245                 250                 255

Asp Thr Pro Lys Met Phe Ser Gly Gly Ser Ala Gly Gln Ser Ser Ile
            260                 265                 270

Phe Gln Ser Leu Asp Val Leu Leu Gly Ile Lys His Glu Ala Gly Lys
            275                 280                 285

Glu Ser Pro Ala Glu Phe Leu Gln Glu Met Arg Glu Tyr Met Pro Pro
            290                 295                 300

Ala His Arg Asn Phe Leu Phe Leu Glu Ser Ala Pro Val Arg
305                 310                 315                 320

Glu Phe Val Ile Ser Arg His Asn Glu Asp Leu Thr Lys Ala Tyr Asn
            325                 330                 335

Glu Cys Val Asn Gly Leu Val Ser Val Arg Lys Phe His Leu Ala Ile
            340                 345                 350

Val Asp Thr Tyr Ile Met Lys Pro Ser Lys Lys Pro Thr Asp Gly
            355                 360                 365

Asp Lys Ser Glu Glu Pro Ser Asn Val Glu Ser Arg Gly Thr Gly Gly
            370                 375                 380

Thr Asn Pro Met Thr Phe Leu Arg Ser Val Lys Asp Thr Glu Lys
385                 390                 395                 400
```

```
Ala Leu Leu Ser Trp
              405

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)

<400> SEQUENCE: 44

Ala Pro Trp Trp Phe
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)

<400> SEQUENCE: 45

Ser Pro Ala Trp Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)

<400> SEQUENCE: 46

Ser Pro Trp Ala Phe
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 47

Ser Pro Trp Trp Ala
1               5

<210> SEQ ID NO 48
```

```
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: 4-fluoro-L-phenylalanine
<222> LOCATION: (5)..(5)

<400> SEQUENCE: 48

Asn Ala Phe Trp Phe
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: 4-fluoro-L-phenylalanine
<222> LOCATION: (5)..(5)

<400> SEQUENCE: 49

Asn Leu Ala Trp Phe
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
<220> FEATURE:
<221> NAME/KEY: 4-fluoro-L-phenylalanine
<222> LOCATION: (5)..(5)

<400> SEQUENCE: 50

Asn Leu Phe Ala Phe
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 51
```

```
Asn Leu Phe Trp Ala
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 52

Phe Ala Phe Trp Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)
<220> FEATURE:
<221> NAME/KEY: D-amino acid
<222> LOCATION: (5)..(5)

<400> SEQUENCE: 53

Phe Arg Ala Trp Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 54

Phe Arg Phe Ala Ser
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 55

Ala Tyr Arg Ala Tyr
1               5
```

```
<210> SEQ ID NO 56
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 56

Trp Ala Arg Ala Tyr
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 57

Trp Tyr Arg Ala Ala
1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 4-fluoro-L-phenylalanine
<222> LOCATION: (4)..(4)

<400> SEQUENCE: 58

Pro Trp Trp Phe
1

<210> SEQ ID NO 59
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 59

Ser Pro Trp Trp
1

<210> SEQ ID NO 60
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
```

```
<221> NAME/KEY: 1-methyl-Ltryptophan
<222> LOCATION: (3)..(3)
<220> FEATURE:
<221> NAME/KEY: 4-fluoro-L-phenylalanine
<222> LOCATION: (4)..(4)

<400> SEQUENCE: 60

Asn Phe Trp Phe
1

<210> SEQ ID NO 61
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(3)
<220> FEATURE:
<221> NAME/KEY: 1-methyl-Ltryptophan
<222> LOCATION: (4)..(4)

<400> SEQUENCE: 61

Asn Leu Phe Trp
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: 1-methyl-Ltryptophan
<222> LOCATION: (3)..(3)
<220> FEATURE:
<221> NAME/KEY: D-amino acid
<222> LOCATION: (4)..(4)

<400> SEQUENCE: 62

Phe Arg Trp Ser
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 63

Tyr Arg Ala Tyr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)
```

```
<400> SEQUENCE: 64

Trp Arg Ala Tyr
1

<210> SEQ ID NO 65
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 65

Trp Tyr Ala Tyr
1

<210> SEQ ID NO 66
<211> LENGTH: 25
<212> TYPE: PRT
<213> ORGANISM: Homo sapiens

<400> SEQUENCE: 66

Tyr Glu Gly Phe Trp Glu Asp Pro Lys Glu Phe Ala Gly Gly Ser Ala
1               5                   10                  15

Gly Gln Ser Ser Val Phe Gln Cys Phe
            20                  25

<210> SEQ ID NO 67
<211> LENGTH: 25
<212> TYPE: PRT
<213> ORGANISM: Mus musculus

<400> SEQUENCE: 67

Tyr Glu Gly Val Trp Asp Thr Pro Lys Met Phe Ser Gly Gly Ser Ala
1               5                   10                  15

Gly Gln Ser Ser Ile Phe Gln Ser Leu
            20                  25

<210> SEQ ID NO 68
<211> LENGTH: 25
<212> TYPE: PRT
<213> ORGANISM: Macaca mulatta

<400> SEQUENCE: 68

Tyr Glu Gly Phe Trp Glu Gly Pro Lys Lys Phe Ala Gly Gly Ser Ala
1               5                   10                  15

Ala Gln Ser Ser Ile Phe Gln Cys Phe
            20                  25

<210> SEQ ID NO 69
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: N-methyl valine
<222> LOCATION: (3)..(3)
<220> FEATURE:
<221> NAME/KEY: D-amino acid
<222> LOCATION: (4)..(5)
```

<400> SEQUENCE: 69

Trp Tyr Val Ala Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: phenyl tyrosine
<222> LOCATION: (2)..(2)
<220> FEATURE:
<221> NAME/KEY: methyl valine
<222> LOCATION: (3)..(3)
<220> FEATURE:
<221> NAME/KEY: methyl phenylalanine
<222> LOCATION: (5)..(5)

<400> SEQUENCE: 70

Trp Tyr Val Gly Phe
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 71

Gly Gly Gly Gly Gly Gly
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 72

Ala Glu Ala Ala Ala Lys
1               5

<210> SEQ ID NO 73
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 73

Ala Ala Asx Ala
1

<210> SEQ ID NO 74
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: 6XHis-PEG N-terminal tag

```
<222> LOCATION: (1)..(1)

<400> SEQUENCE: 74

Gly Phe Trp Glu Asp Pro Lys Glu Phe Gln Ala Phe Gly Val Gly Ser
1               5                   10                  15

Ser Ala Gln Gly Ser
            20

<210> SEQ ID NO 75
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: 6XHis-PEG N-terminal tag
<222> LOCATION: (1)..(1)

<400> SEQUENCE: 75

Glu Pro Asp Phe Lys Glu Trp Gly Phe Ala Gly Gly Ser Ala Gly Gln
1               5                   10                  15

Ser Ser Val Phe Gln
            20

<210> SEQ ID NO 76
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: 6XHis-PEG N-terminal tag
<222> LOCATION: (1)..(1)

<400> SEQUENCE: 76

Leu Pro Pro Ile Leu Val Tyr Ala Asp Cys Val Leu Lys Ala Lys Asn
1               5                   10                  15

Asn Pro Trp Lys Lys Asp
            20

<210> SEQ ID NO 77
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: 6XHis-PEG N-terminal tag
<222> LOCATION: (1)..(1)

<400> SEQUENCE: 77

Leu Cys Pro Asp Pro Ala Ile Val Leu Tyr Leu Ala Asn Trp Lys Lys
1               5                   10                  15

Lys Asp Pro Asn Lys
            20
```

UNITED STATES PATENT AND TRADEMARK OFFICE
CERTIFICATE OF CORRECTION

| | | |
|---|---|---|
| PATENT NO. | : 12,216,122 B2 | Page 1 of 2 |
| APPLICATION NO. | : 16/879611 | |
| DATED | : February 4, 2025 | |
| INVENTOR(S) | : Agnew et al. | |

It is certified that error appears in the above-identified patent and that said Letters Patent is hereby corrected as shown below:

In the Claims

In Columns 151 and 152, in Claim 15, Lines 17-29, delete

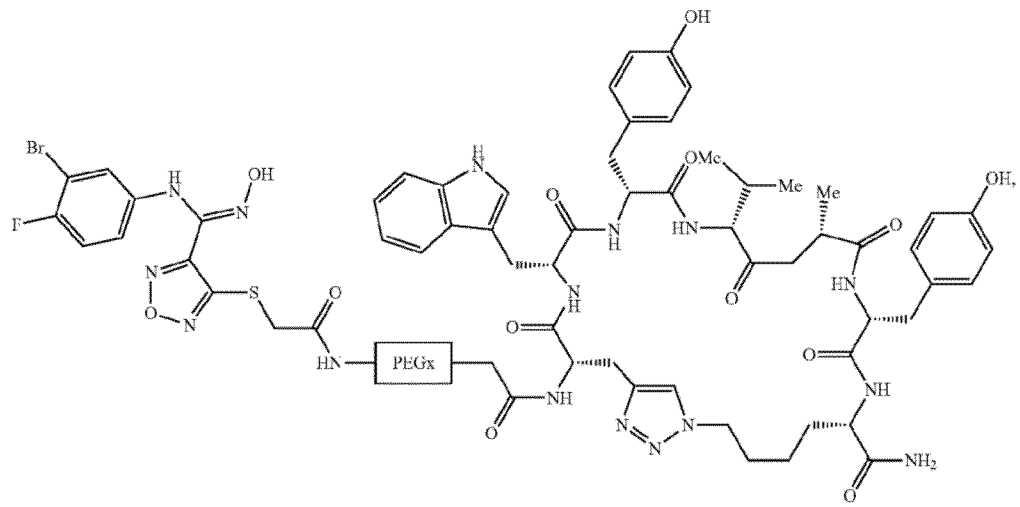

" and insert

Signed and Sealed this
Seventeenth Day of June, 2025

Coke Morgan Stewart
*Acting Director of the United States Patent and Trademark Office*

--  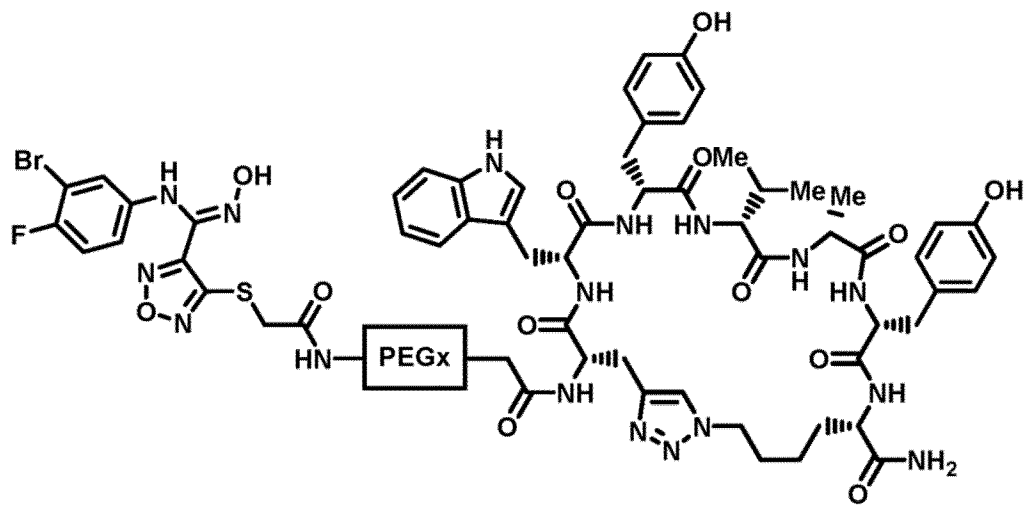  --, therefor.